US008476245B2

(12) United States Patent
Pourmotabbed et al.

(10) Patent No.: US 8,476,245 B2
(45) Date of Patent: Jul. 2, 2013

(54) INHIBITION OF TUMOR GROWTH AND INVASION BY ANTI MATRIX METALLOPROTEINASE DNAZYMES

(75) Inventors: Tayebeh Pourmotabbed, Cordova, TN (US); Hisashi Hasegawa, Niigata (JP); Chad Batson, Memphis, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 321 days.

(21) Appl. No.: 12/390,628

(22) Filed: Feb. 23, 2009

(65) Prior Publication Data

US 2009/0227663 A1    Sep. 10, 2009

Related U.S. Application Data

(62) Division of application No. 11/056,620, filed on Feb. 11, 2005, now abandoned.

(60) Provisional application No. 60/543,490, filed on Feb. 11, 2004.

(51) Int. Cl.
*A61K 48/00* (2006.01)
(52) U.S. Cl.
USPC ......... 514/44; 536/24.5; 536/24.31; 536/24.1
(58) Field of Classification Search
None
See application file for complete search history.

(56) References Cited

U.S. PATENT DOCUMENTS

| | | | |
|---|---|---|---|
| 4,554,101 A | 11/1985 | Hopp | |
| 5,334,711 A | 8/1994 | Sproat et al. | |
| 5,627,053 A | 5/1997 | Usman et al. | |
| 5,672,695 A | 9/1997 | Eckstein et al. | |
| 5,716,824 A | 2/1998 | Beigelman et al. | |
| 5,807,718 A * | 9/1998 | Joyce et al. | 435/91.5 |
| 5,854,038 A | 12/1998 | Sullenger et al. | |
| 5,858,784 A | 1/1999 | Debs et al. | |
| 5,871,982 A | 2/1999 | Wilson et al. | |
| 5,998,203 A | 12/1999 | Matulic-Adamic et al. | |
| 6,001,311 A | 12/1999 | Brennan | |
| 6,013,638 A | 1/2000 | Crystal et al. | |
| 6,022,737 A | 2/2000 | Niven et al. | |
| 6,057,156 A | 5/2000 | Akhtar et al. | |
| 6,103,890 A | 8/2000 | Jarvis et al. | |
| 6,127,173 A | 10/2000 | Eckstein et al. | |
| 6,136,295 A | 10/2000 | Edwards et al. | |
| 6,248,878 B1 | 6/2001 | Matulic-Adamic et al. | |
| 6,251,666 B1 | 6/2001 | Beigelman | |
| 6,300,074 B1 | 10/2001 | Gold et al. | |
| 6,326,174 B1 | 12/2001 | Joyce et al. | |
| 6,361,941 B1 | 3/2002 | Todd et al. | |
| 6,399,371 B1 | 6/2002 | Falduto et al. | |
| 6,566,127 B1 | 5/2003 | Pavco et al. | |
| 6,586,238 B1 | 7/2003 | Matulic-Adamic et al. | |
| 6,602,858 B2 | 8/2003 | Beigelman | |
| 6,617,438 B1 | 9/2003 | Beigelman et al. | |
| 6,623,962 B1 | 9/2003 | Akhtar et al. | |
| 6,673,611 B2 | 1/2004 | Thompson et al. | |
| 6,686,463 B2 | 2/2004 | Beigelman et al. | |
| 2002/0042062 A1 | 4/2002 | Stearns et al. | |
| 2003/0139332 A1 | 7/2003 | Noble et al. | |
| 2006/0019914 A1 | 1/2006 | Pourmotabbed | |

FOREIGN PATENT DOCUMENTS

| | | |
|---|---|---|
| CA | 2359180 | 6/2007 |
| EP | 0 439 095 | 7/1991 |
| WO | WO91/03162 | 3/1991 |
| WO | WO92/07065 | 4/1992 |
| WO | WO93/15187 | 8/1993 |
| WO | WO93/23569 | 11/1993 |
| WO | WO96/32280 | 10/1996 |
| WO | WO97/26270 | 7/1997 |
| WO | WO97/45550 | 12/1997 |
| WO | WO97/47763 | 12/1997 |
| WO | WO98/13526 | 4/1998 |
| WO | WO98/54345 | 12/1998 |
| WO | WO99/07409 | 2/1999 |
| WO | WO99/32619 | 7/1999 |
| WO | WO99/54459 | 10/1999 |
| WO | WO00/01846 | 1/2000 |
| WO | WO00/44895 | 8/2000 |
| WO | WO00/44914 | 8/2000 |
| WO | WO00/63364 | 10/2000 |
| WO | WO01/04313 | 1/2001 |
| WO | WO01/29058 | 4/2001 |
| WO | WO01/36646 | 5/2001 |
| WO | WO01/68836 | 9/2001 |
| WO | WO01/75164 | 10/2001 |
| WO | WO01/92513 | 12/2001 |
| WO | WO02/44321 | 6/2002 |
| WO | WO02/055692 | 7/2002 |
| WO | WO02/055693 | 7/2002 |

OTHER PUBLICATIONS

Fang et al. (PNAS 2000, vol. 97: 3884-3889).*
Kondraganti et al. (Cancer Research 2000, vol. 60: 6851-6855).*
Beigelman et al. (JBC 1005, vol. 270: 25702-25708).*
Santoro et al. (PNAS 1997, vol. 94: 4262-4266).*
Aalinkeel et al., "Gene expression of antigenic factors correlated with metastatic potential of prostate cancer cells," Cancer Research, vol. 64, pp. 5311-5321 (2004).
Cairns et al. Catalytic DNA: A Novel Tool for Gene Suppression. Current Drug Targets, vol. 3, pp. 269-279 (2002).

(Continued)

*Primary Examiner* — Kimberly Chong
(74) *Attorney, Agent, or Firm* — Jenkins, Wilson, Taylor & Hunt, P.A.

(57) ABSTRACT

The presently disclosed subject matter provides DNA molecules designed to down regulate the expression of MMP genes in a cell. Also provided are compositions comprising the DNA molecules. The presently disclosed subject matter further provides methods of using the DNA molecules to inhibit metastasis of a cancer cell. The presently disclosed subject matter also provides methods of using the DNA molecules to modulate tumor growth in a subject.

6 Claims, 17 Drawing Sheets

OTHER PUBLICATIONS

Dass et al., "DNAzyme technology and cancer therapy: cleave and let die," Mol. Cancer Ther., vol. 7, No. 2, pp. 233-251 (Feb. 2008).

Fidler, I., "The pathogenesis of cancer metastasis: the 'seed and soil' hypothesis revisited," Nature Reviews, vol. 3, pp. 1-6 (Jun. 2003).

Invitation to Pay Additional Fees corresponding to PCT International Patent Application No. PCT/US05/04294 dated Jan. 6, 2006.

London et al. A novel antisense inhibitor of MMP-9 attenuates angiogenesis, human prostate cancer cell invasion and tumorigenicity. Cancer Gene Therapy 2003, vol. 10. pp. 823-832.

Martin et al., "The other side of MMPs: Protective roles in tumor progression," Cancer Metastasis Rev., vol. 26, Nos. 3-4, pp. 717-724 (2007).

Notification Concerning Transmittal of International Preliminary Report on Patentability corresponding to PCT Application Serial No. PCT/US2005/004294 dated Oct. 12, 2006.

Notification of Transmittal of the International Search Report and the Written Opinion of the International Searching Authority, or the Declaration corresponding to International Patent Application No. PCT/US05/04294 dated Aug. 9, 2006.

Office Communication corresponding to U.S. Appl. No. 11/056,620 dated Dec. 26, 2008.

Office Communication corresponding to U.S. Appl. No. 11/056,620 dated Apr. 23, 2008.

Office Communication corresponding to U.S. Appl. No. 11/056,620 dated Jul. 26, 2007.

Overall et al., "Towards third generation matrix metalloproteinase inhibitors for cancer therapy," British Journal of Cancer, vol. 94, pp. 941-946 (2006).

Overall et al., "Validating matrix metalloproteinases as drug targets and anti-targets for cancer therapy," Nature Reviews, vol. 6, pp. 227-239 (Mar. 2006).

Szemraj et al., "Tissue distribution of a menthyl-conjugated oligodeoxyribonucleotide antisense to PAI-1 mRNA," Acta Biochimica Polonica, vol. 52, No. 4, pp. 849-855 (2005).

Wu et al., "Hepatic artery infusion of antisense oligodeoxynucleotide and lipiodol mixture transfect liver cancer in rats," World Journal of Gastroenterology, vol. 11, No. 16, pp. 2408-2412 (2005).

* cited by examiner

MMP-9 mRNA

```
        1                                              2367
5'— ATG ———————————————————————————————————— 3'
    AS3  27 — 45
    AS4      65 — 83
    AS5           137 — 155
    AS8                185 — 203
    AS6                         335 — 353
```

B

MMP-9 mRNA     5'-CGACCTCAAGTGGCACCAC-3'

AS6 DNAzyme     3'-GCTGGAGTT    ACCGTGGTA-5'
```
                              A      G
                              G      G
                              C      C
                              A      T
                              A      A
                              C      G
                               A T C
```

A  Successful Engraftment

B  Average Tumor Size (L x W)

Figure 10 C-F
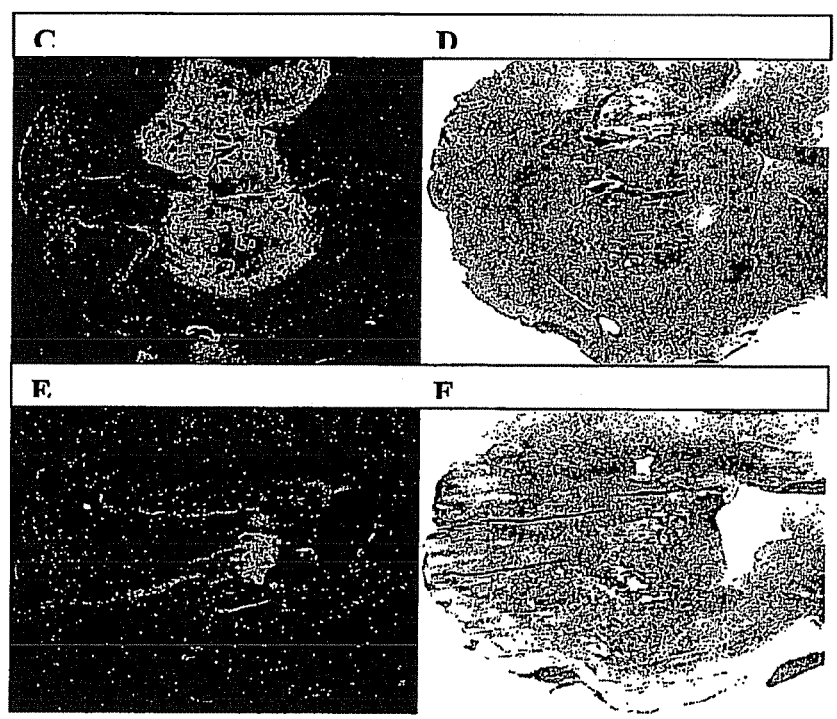

INHIBITION OF TUMOR GROWTH AND INVASION BY ANTI MATRIX METALLOPROTEINASE DNAZYMES

CROSS REFERENCE TO RELATED APPLICATIONS

This application is a divisional of U.S. patent application Ser. No. 11/056,620, filed Feb. 11, 2005, the disclosure of which is incorporated herein by reference in its entirety, which claims the benefit of and priority to U.S. Provisional Patent Application Ser. No. 60/543,490, filed Feb. 11, 2004, the disclosure of which is incorporated herein by reference in its entirety.

GOVERNMENT INTEREST

This work was supported by grant R01 AR041843 from the National Institute of Arthritis and Musculoskeletal and Skin Diseases (NIAMS), U.S. National Institutes of Health (NIH). Thus, the U.S. government has certain rights in the presently disclosed subject matter.

TECHNICAL FIELD

The presently disclosed subject matter generally relates to methods and compositions for inhibiting the expression of matrix metalloproteinase proteins. More particularly, the methods and compositions involve introducing into a cell, for example a cell in a tumor, a DNAzyme having specificity for an mRNA encoding a matrix metalloproteinase, thereby inhibiting expression of the matrix metalloproteinase.

TABLE OF ABBREVIATIONS

2'-H—2'-deoxy
2,5-A—2',5'—linked oligoadenylates
5'-O-DMT—5'—terminal dimethoxytrityl
A—adenine
ACN—acrylonitrile
Ad—adenovirus
AdsiHIF-1α—an adenovirus vector encoding an siRNA directed against HIF-1α
AdsiNT—an adenovirus vector encoding a control siRNA with no known homology to any target gene (i.e. a non-targeted siRNA)
ARNT—aryl hydrocarbon receptor nuclear translocator
ATCC—American Type Culture Collection
C—cytosine
CAT—chloramphenicol acetyltransferase
CMV—cytomegalovirus
CV—column volume
DHFR—dihydrofolate reductase
DIPA—diisopropylethylamine
DMAP—dimethylaminopurine
DMEM—Dulbecco's modified Eagle's medium
DMSO—dimethylsulfoxide
dsRNA—double stranded RNA
EDTA—ethylenediamine tetraacetic acid
FBS—fetal bovine serum
FLT-1—a receptor for VEGF
G—guanine
GFP—green fluorescent protein
HF—hydrogen fluoride
HIF-1—MMP factor 1
HIF-1α—MMP factor 1α
HIF-1β—MMP factor 1β; ARNT
HPLC—high performance liquid chromatography
HPRT—hypoxanthine phosphoribosyl transferase
HREs—hypoxia responsive elements
HRP—horseradish peroxidase
hsp—heat shock protein
IFN-α—interferon alpha
IFN-γ—interferon gamma
IgG—immunoglobulin gamma
IL2—interleukin 2
IL4—interleukin 4
IL6—interleukin 6
MMP matrix metalloproteinase
m.o.i.—multiplicity of infection
NaOAc—sodium acetate
NIH—National Institutes of Health
PAGE—polyacrylamide gel electrophoresis
PBS—phosphate-buffered saline
PBST—phosphate-buffered saline plus Tween 20
pfu—plaque-forming unit
PKR—RNA-dependent protein kinase
PSA—prostate serum antigen
PyBrOP—bromotripyrrolidinophosphoniumhexa-fluo-rorophosphate
pVHL—von Hippel-Lindau protein
RISC—RNA-induced silencing complex
RNAi—RNA interference
SDS—sodium dodecyl sulfate
SE—standard error
siRNA—small (or short) interfering RNA
SV40—simian virus 40
SSC—standard saline citrate
T—thymine
TAFs—Transcription Associated Factors
TCA—trichloroacetate
TEA—triethylamine
TEAA—triethylamine acetate
TFA—trifluoroacetic acid
THF—tetrahydrofuran
$T_m$—thermal melting point
TNF—tumor necrosis factor
U—uracil
VEGF—vascular endothelial growth factor

BACKGROUND

Despite significant advances in medical research and technology, cancer continues to be one of the leading causes of death in the United States and throughout the world. There are in excess of one million new cases of cancer reported in the United States alone, and more than half a million people die in this country every year from cancer.

Current treatments for cancer include surgical removal, chemotherapy and/or radiation treatment of tumors, yet each has its limitations. In the former case, once a tumor has metastasized by invading the surrounding tissue or by moving to a distant site, it can be virtually impossible for the surgeon to remove all cancerous cells. Any such cells left behind can continue growing, leading to a recurrence of cancer following surgery. Current radiation therapy strategies are also frequently unsuccessful at eradicating a patient's cancer. Following radiation therapy, cancer can recur because it is often not possible to deliver a sufficiently high dose of radiation to kill all the tumor cells without at the same time injuring the surrounding normal tissue. Cancer can also recur because tumors show widely varying susceptibilities to radiation-induced cell death. Thus, the inability of current treatment protocols to eliminate tumor cells is an important clinical limitation leading to unsuccessful cancer therapy (Lindegaard et al., 1996; Suit, 1996; Valter et al., 1999).

Newer treatment strategies are needed to address the challenges that result from the inability to successfully treat neoplastic disease. One of the major challenges facing the medical oncologist is selectivity: the ability to kill tumor cells without causing damage to normal cells in the surrounding area. Various current approaches take advantage of the fact that in most cases tumor cells grow more quickly than normal cells, so strategies designed to kill rapidly growing cells are somewhat selective for tumor cells (see Yazawa et al., 2002). However, these methods also kill certain cell types in the body that normally divide rapidly, most notably cells in the bone marrow, resulting in complications such as anemia and neutropenia (reviewed in Vose & Armitage, 1995). Other strategies are based upon the production of antibodies directed against tumor-specific antigens (reviewed in Sinkovics & Horvath, 2000). However, few such antigens have been identified, limiting the applicability of these approaches. As such, there is a need for new methods to enhance the selectivity of cancer treatment approaches.

Thus, there exists a long-felt and continuing need in the art for effective therapies to specifically target and kill tumor cells in a subject. The presently disclosed subject matter addresses this and other needs in the art.

SUMMARY

The presently disclosed subject matter provides an isolated enzymatic DNA molecule comprising a polynucleotide sequence having binding specificity for a target region of a mRNA encoding a matrix metalloproteinase protein. In some embodiments, the enzymatic DNA molecule is a DNAzyme. In some embodiments, the DNAzyme comprises a catalytic domain flanked on each side by substrate binding domains each having binding specificity for a distinct nucleotide sequence of the target region. In some particular embodiments, the enzymatic DNA molecule has a nucleotide sequence comprising the sequence of SEQ ID NOs:1-12, 22, and 29. In some embodiments, the DNA molecule comprises a modification that increases the stability of the DNA molecule, and in some embodiments the modification comprises an inverted deoxythymidine at the 3' end of the DNA molecule. In some embodiments, the matrix metalloproteinase protein is MMP-2 or MMP-9.

In some embodiments, a composition is provided comprising the enzymatic DNA molecule of the presently disclosed subject matter and in some embodiments, the composition further comprises a carrier. In other embodiments, the composition comprises more than one enzymatic DNA molecule, wherein each DNA molecule has binding specificity for a different target region of an mRNA encoding a matrix metalloproteinase protein. In some embodiments, the target regions are located on the same mRNA and in other embodiments, the target regions correspond to mRNAs encoding different matrix metalloproteinase proteins. In some embodiments, the composition comprises a DNA molecule having binding specificity for a target region of an mRNA encoding MMP-2 and a DNA molecule having binding specificity for a target region of an mRNA encoding MMP-9.

The presently disclosed subject matter further provides a methods for utilizing the novel DNA molecules.

The presently disclosed subject matter provides in some embodiments a method of modulating cellular expression of at least one matrix metalloproteinase protein, the method comprising introducing into a cell at least one DNA oligonucleotide having binding specificity for a target region of a mRNA encoding a matrix metalloproteinase protein. In some embodiments, modulating cellular expression of the matrix metalloproteinase protein comprises inhibiting expression of the matrix metalloproteinase protein.

The presently disclosed subject matter further provides a method of inhibiting metastasis of a cancer cell, the method comprising introducing into a cancer cell at least one DNA oligonucleotide having binding specificity for a target region of a mRNA encoding a protein which contributes to metastasis. In some embodiments, inhibiting metastasis of the cancer cell comprises inhibiting expression of the protein which contributes to metastasis.

In some embodiments, the protein is an enzyme that degrades extracellular matrix components and in some embodiments, the enzyme is a matrix metalloproteinase protein. In some particular embodiments, the matrix metalloproteinase protein is MMP-2, MMP-9, or both MMP-2 and MMP-9.

In some embodiments, the cancer cell is a cell from a cancerous tissue selected from the group consisting of glioma, melanoma, fibrosarcoma, and adenosarcoma.

The presently disclosed subject matter still further provides a method of modulating tumor growth in a subject, the method comprising administering to a subject a composition comprising at least one DNA oligonucleotide having binding specificity for a target region of a mRNA encoding a matrix metalloproteinase protein. In some embodiments, modulating tumor growth comprises inhibiting tumor growth.

Accordingly, it is an object of the presently disclosed subject matter to provide a method of modulating tumor growth by providing DNAzymes having binding specificity for target matrix metalloproteinases expressed by the tumor. This and other objects are achieved in whole or in part by the presently disclosed subject matter.

An object of the presently disclosed subject matter having been stated above, other objects and advantages of the presently disclosed subject matter will become apparent to those of ordinary skill in the art after a study of the following description and non-limiting Examples.

BRIEF DESCRIPTION OF THE DRAWINGS

FIG. 1A is a schematic depicting target sites of candidate DNAzymes in human MMP-9 mRNA.

FIG. 1B depicts the sequence of a target region of the human MMP-9 mRNA and the susbstrate binding domains of the AS6 DNAzyme (SEQ ID NO:6) binding with specificity to the target sequence.

FIG. 3A shows control brain from healthy rat. FIG. 3B is a 20× magnification image adjacent to needle insertion point. FIG. 3C is a 20× magnification image 0.75 cm anterior to needle insertion point. FIG. 3D is a 40× magnification image 1.5 cm deep to needle insertion point.

FIG. 6A shows results from Cos-7NG cells, FIG. 6B shows results from rat C6 glioma cells, and FIG. 6C shows results from human SNB19 glioma cells. All cells were sorted by FACS and re-plated at 1.5×10$^5$ cells in 0.3 ml of serum free medium on the membrane insert of the cell invasion assay. After 24 hour of incubation on the membrane, the number of cells that migrated though the ECM layer attached to the bottom of the polycarbonate membrane was quantitated by staining and destaining cells and colorimetric analysis of the OD of the dye/solute mixture at 560 nm. The ratio (%) of invaded cells treated with AS6 or S6 against that of cells treated with DOTAP alone (control) is shown. *P<0.05 compared with control. The experiment was repeated four times, and the results represent the average.

FIG. 10A shows graphic representation of the percent success of C6 glioma graft into immunocompetent rats in untreated vs. treated test groups. FIG. 10B shows graphic representation of the average size (length×width) of tumors after 14 days of glioma development in a rat intracranial glioma model in untreated vs. treated test groups.

FIG. 14A shows RT-PCR analysis of MMP-2 production in U87 NG cells transfected with (lane 1) or without 72K01 DNAzyme (lane 2). β-actin (lanes 3 and 4) was used as a control. FIG. 14B shows a gelatin zymogram of U87MG supernatant collected from equal number of cells transfected with (lane 2) or without (Lane 1) the 72K01 DNAzyme. FIG. 14C shows Western Blot analysis of U87MG supernatant transfected without (lane 1) or with 72K01 DNAzyme using antibody against MMP-2 protein.

DETAILED DESCRIPTION

Figure 2:
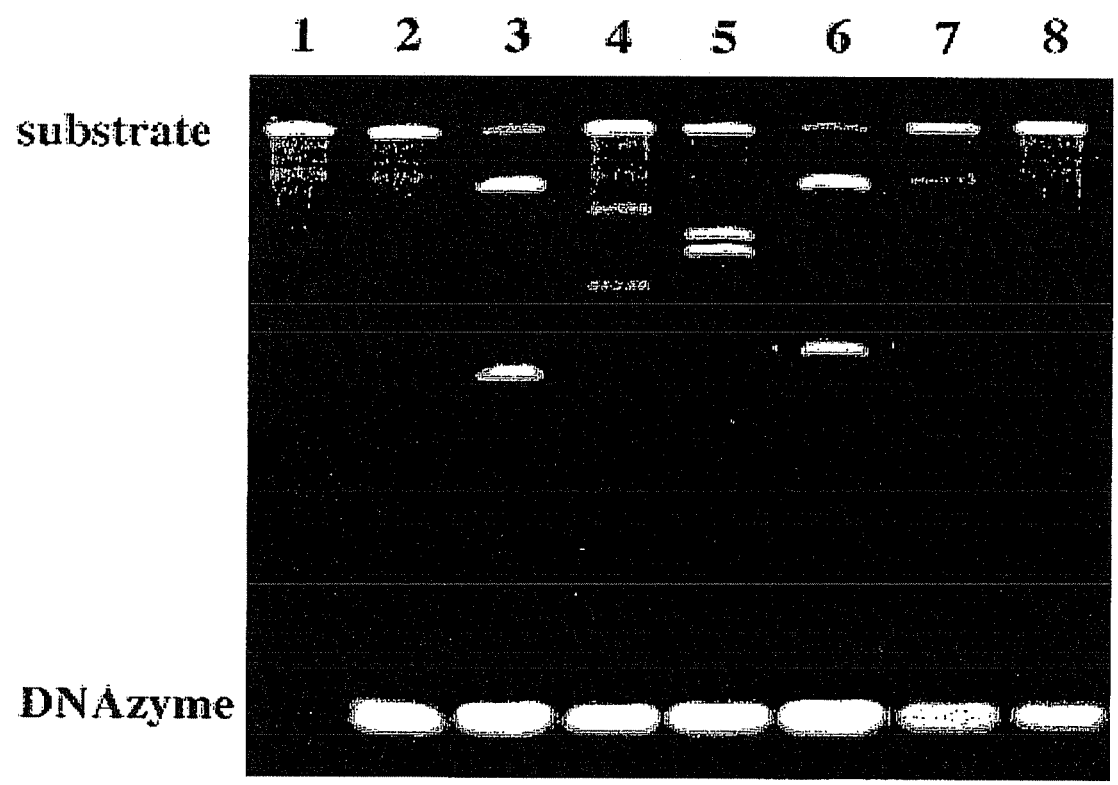
FIG. 2 is a photograph of a polyacrylamide-urea gel showing in vitro cleavage of RNA substrate by candidate DNAzymes. 12.5 µM of each DNAzyme or control oligonucleotide and 0.48 µM of RNA substrate (764 nt) was incubated in 50 mM Tris-HCl, pH 7.5, and 10 mM MgCl2 at 37° C. for 2 hours. After incubation, substrate incubated alone (lane 1) or the reaction mixture with AS3 (SEQ ID NO:3; lane 2), AS4 (SEQ ID NO:4; lane 3), AS5 (SEQ ID NO:5; lane 4), AS8 (SEQ ID NO:8; lane 5), AS6 (SEQ ID NO:6; lane 6), S6 (SEQ ID NO: 18; lane 7), and random (scrambled substrate binding domains) DNA oligonucleotide (SEQ ID NO:20; lane 8) was mixed with 90% formamide in TBE, and separate on a 4% polyacrylamide-urea gel. The RNA bands were visualized by Ethidium Bromide staining.

The presently disclosed subject matter generally relates to methods and compositions for suppressing or inhibiting the growth and/or invasion of a cell that expresses a matrix metalloproteinase gene. In some embodiments, the methods involve introducing into a cell, for example a cell in a tumor, a DNAzyme having specificity for an mRNA encoding a matrix metalloproteinase, thereby inhibiting expression of the matrix metalloproteinase and inhibiting growth and/or invasion of the cell.

I. General Considerations

Cancer continues to be one of the leading causes of death throughout the world and current therapeutics for many types of cancers, particularly metastatic cancers are insufficient. In particular, tumors of the central nervous system (CNS) are notoriously difficult to treat.

The most prevalent form of adult primary CNS tumors is collectively referred to as glioma, and the most common, devastating, and high-grade glioma is glioblastoma multiforme (GBM). Long term survival of patients with a GBM diagnosis with the best radiological, surgical, and anti-tumor drug therapy available is extremely rare. The historical median survival for GBM patients is 3 to 12 months depending on age and other prognostic factors. Metastatic tumors of the CNS such as adenocarcinomas of the lung, breast, and gastrointestinal tract are the most common type of CNS tumor overall and have an equally devastating prognosis.

CNS tumors in general are difficult to treat because of the complexities associated with removing cancerous cells from a background of normal brain tissue without introducing considerable neurological damage. Increased intracranial pressure and intraparenchymal hemorrhage significantly complicate all aspects of treatment. Conventional therapy for malignant glioma consists of complete gross resection followed by radiation, either with or without chemotherapy. Radiation is indicated because surgical resection misses micro populations of cells that have migrated from the primary tumor site. However, currently accepted therapeutic adjuvants to surgery such as radiation therapy and chemotherapy provide only a minor improvement in the disease course and life expectancy of patients diagnosed with malignant glioma. The blood brain barrier prevents use of most chemotherapeutic agents, and those that are available do not significantly impact the course of disease and often have unacceptable side effect profiles. Therefore, new approaches that target malignant glioma are needed if these tumors are going to be treated adequately in the future.

I.A. Matrix Metalloproteinases

Although the precise mechanisms by which malignant tumor cells metastasize are not fully understood, metastasis and cell invasion are thought to be mediated, at least in part, through the degradation of basement membrane by neutral matrix metalloproteinases (MMP) produced by tumor cells. MMPs are members of a unique family of zinc-binding endopeptidases that together have the ability to mount a concerted degradative attack on virtually all components of the extracellular matrix (ECM). These enzymes are secreted as catalytically latent species that are processed to their activated forms in vivo by other proteinases. Members of this important protease family have been divided into five subclasses based on structural similarity and substrate specificity. These include: collagenases (MMP-1, MMP-8 & MMP-13), gelatinases (MMP-2 and MMP-9), stromelysins (MMP-3 and MMP-10), metalloelastase, Membrane-type MMPs (MT-MMP; MMP-14, MMP 15, MMP-16, MMP-17, MMP-24, and MMP-25), and others (MMP-7, MMP-11, MMP-12, MMP-19, MMP-20 and MMP-23).

Clues to the biological functions of MMPs come from their substrate specificities. Collagenases can cleave native fibrillar collagen types I, II and III. Although less well studied, the collagenases can also cleave collagen types VII, and X as well as gelatin, aggrecan, entactin, and tenascin. Gelatinases digest elastin and aggrecan, in addition to collagen types IV, V, and XI. They also act synergistically with interstitial collagenase in the degradation of fibrillar collagens. MMP-2 (gelatinase A) has been shown to cleave native type I collagen in the same position as fibroblast collagenase, and MMP-9 (gelatinase B) has been shown to cleave α2 chains of type I collagen. The third member of the MMP family stromelysins, are enzymes that have a wide spectrum of action on extracellular matrix macromolecules and degrade proteoglycans, fibronectin, laminin, type IV and IX collagens, as well as gelatin. In addition to its direct action, stromelysin may indirectly affect the degradation of ECM by activating latent collagenase and gelatinases. Lastly the MT-MMPs that are localized on cell surfaces, are thought to play a major role in the activation of pro-MMP-2 in various tissues. In addition to its activator function, MT1-MMP digests the triple helical portions of interstitial collagen types I, II, and III as well as other ECM components including fibronectin, laminin, aggrecan, and gelatin.

The uncontrolled expression of MMPs, especially MMP-2 and -9, is associated with many pro-oncogenic events such as angiogenesis, tumor cell invasion, and tumor cell metastasis. Although few cell types express MMP-9 physiologically, the majority of human metastatic tumor cells (i.e., melanoma, fibrosarcoma, breast adenocarcinoma, glioma, etc.) that have been tested consistently show elevated MMP-9 activity compared with benign control cells. Tumor cells stably expressing the MMP-9 cDNA have been shown to widely metastasize in nude mice, whereas inhibition of the MMP-9 activity has been demonstrated to prevent metastasis in other models.

Interestingly, immunohistochemical examination of benign and malignant breast disease has shown that mRNA and protein for MMPs are expressed not only by the tumor cells but also by cells in the surrounding stroma. These data suggest that the interaction of tumor cells with the basement membrane may trigger the expression and release of MMPs by the surrounding tissues, ultimately resulting in increased degradation of the basement membrane with subsequent metastasis. One of the major components of the poor prognosis associated with high-grade gliomas is their ability to invade tissues and migrate with subsequent metastasis to distant sites in the brain. Many human glioma cell lines have been shown to express MMPS, and MMPs2 and -9 in particular have been shown to be up-regulated at the mRNA and protein levels in the SNB19 and the U87MG human glioma cell lines. In addition, it has been demonstrated that the rat C6 glioma cell line also expresses MMP2 and -9 at the mRNA and protein level.

I.B. Enzymatic Nucleotide Molecules

The association between MMP expression, cell invasion, and cancer prognosis is clear. Therefore, it would be advantageous to have specific inhibitors against MMPs as potential therapeutics. Recent attempts have been made to use chemical MMP inhibitors. However, although synthetic MMP inhibitors have been shown to have anti-metastatic effects in animal systems, these drugs have not performed as well in human clinical trials.

Therefore, therapeutic intervention in the MMP cascade might provide an alternative therapeutic avenue, particularly at the level of induction and protein production. Recently, antisense oligonucleotides, catalytic RNA (ribozymes), and catalytic DNA (DNAzymes) have emerged as novel, highly selective inhibitors or modulators of gene expression. The advantage of antisense therapy over small molecule based drugs (which typically interact not only with their target but also with all structurally related proteins) is that its substrate (targeted RNA) is well defined and unique. Moreover, they seem to be well tolerated by subjects.

DNAzymes and ribozymes are enzymatic antisense oligonucleotides that in the absence of proteins, bind to and cleave specific RNA sequences resulting in decreased expression of the encoded protein. Ribozymes and DNAzymes retain antisense properties allowing them to bind specifically a target gene. Typically, the target mRNA sites are two separate regions 6-7 nucleotides in length that are bound by two independent binding domains 6-7 nucleotides in length. The advantage of this method over traditional antisense strategies is that one enzymatic oligonucleotide molecule can catalyze the cleavage of many targeted mRNAs. Thus, lower levels of nucleotide are needed to inactivate a particular mRNA. Reports of studies demonstrating the efficacy of antisense and ribozyme based therapies are beginning to emerge. However, at present, there are no known reports of studies that investigate DNAzymes targeted to any gene associated with gliomas.

As such, the presently disclosed subject matter takes advantage of the ability of short, single stranded enzymatic DNA molecules, e.g. DNAzymes, to cause the down regulation of cellular genes through the specific binding of the DNAzyme with the mRNA transcribed from the gene and subsequent enzymatic cleavage of the mRNA to provide novel therapeutics and methods of use for treating cancers, and in particular gliomas. In some embodiments, the presently disclosed subject matter provides novel enzymatic DNA molecules having specificity for MMP RNA sequences.

II. Definitions

While the following terms are believed to be well understood by one of ordinary skill in the art, the following definitions are set forth to facilitate explanation of the presently disclosed subject matter.

Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in this application, including the claims. Thus, for example, reference to "a vector" includes a plurality of such vectors, and so forth.

As used herein, the term "about," when referring to a value or to an amount of mass, weight, time, volume, concentration or percentage is meant to encompass variations of ±20% or ±10%, in another example ±5%, in another example ±1%, and in still another example ±0.1% from the specified amount, as such variations are appropriate to perform the disclosed method.

As used herein, "significance" or "significant" relates to a statistical analysis of the probability that there is a non-random association between two or more entities. To determine whether or not a relationship is "significant" or has "significance", statistical manipulations of the data can be performed to calculate a probability, expressed as a "p-value". Those p-values that fall below a user-defined cutoff point are regarded as significant. In one example, a p-value less than or equal to 0.05, in another example less than 0.01, in another example less than 0.005, and in yet another example less than 0.001, are regarded as significant.

As used herein, the term "enzymatic DNA molecule" is used to describe a DNA-containing molecule that is capable of functioning as an enzyme. In the present disclosure, the term "enzymatic DNA molecule" includes endoribonucleases. The term "enzymatic DNA molecule" as used herein is inclusive of the terms "DNAzyme", "deoxyribozyme" and "catalytic DNA molecule", which terms should all be understood to include enzymatically active portions thereof, whether they are produced synthetically or derived from organisms or other sources.

The term "enzymatic DNA molecule" as used herein also includes DNA molecules that have complementarity in a substrate binding domain or region to a specified oligoribonucleotide target or substrate. Such molecules also have an enzymatic activity, which is active to specifically cleave the oligoribonucleotide substrate. Stated in another fashion, the enzymatic DNA molecule is capable of cleaving the oligoribonucleotide substrate intermolecularly. The complementarity functions to allow sufficient hybridization of the enzymatic DNA molecule to the substrate oligoribonucleotide at a target region to allow the intermolecular cleavage of the substrate to occur. While one-hundred percent (100%) complementarity is preferred, complementarity in the range of 75-100% is also useful and contemplated by the presently disclosed subject matter.

The term "endodeoxyribonuclease", as used herein, is an enzyme capable of cleaving a substrate comprising predominantly DNA. The term "endoribonuclease", as used herein, is an enzyme capable of cleaving a substrate comprising predominantly RNA.

As used herein, the phrase "target RNA" or "target region of an RNA" refers to an RNA molecule (for example, an mRNA molecule encoding a matrix metalloproteinase (MMP) gene product) that is a target for downregulation. Similarly, the phrase "target site" refers to a sequence within a target RNA that is "targeted" for cleavage mediated by an enzymatic DNA molecule that contains sequences within its substrate binding domains that are complementary to the target site. Also similarly, the phrase "target cell" refers to a cell that expresses a target RNA and into which an enzymatic DNA molecule is intended to be introduced. A target cell is in some embodiments a cell in a subject. For example, a target cell can comprise a cell that expresses a MMP gene.

The term "cellular expression" or "cellular gene expression" generally refers to the cellular processes by which a biologically active polypeptide is produced from a DNA sequence and exhibits a biological activity in a cell. As such, gene expression involves the processes of transcription and translation, but also involves post-transcriptional and post-translational processes that can influence a biological activity of a gene or gene product. These processes include, but are not limited to RNA syntheses, processing, and transport, as well as polypeptide synthesis, transport, and post-translational modification of polypeptides. Additionally, processes that affect protein-protein interactions within the cell can also affect gene expression as defined herein.

As used herein, the term "modulate" refers to a change in the expression level of a gene, or a level of RNA molecule or equivalent RNA molecules encoding one or more proteins or protein subunits, or activity of one or more proteins or protein subunits is up regulated or down regulated, such that expression, level, or activity is greater than or less than that observed in the absence of the modulator. For example, the term "modulate" can mean "inhibit" or "suppress", but the use of the word "modulate" is not limited to this definition.

As used herein, the terms "inhibit", "suppress", "down regulate", and grammatical variants thereof are used interchangeably and refer to an activity whereby gene expression of and/or a level of an RNA encoding one or more gene products is reduced below that observed in the absence of a nucleic acid molecule of the presently disclosed subject matter. In some embodiments, inhibition with a DNA oligonucleotide of the presently disclosed subject matter results in a decrease in the steady state level of a target RNA, such as an mRNA. In some embodiments, inhibition with a DNA oligonucleotide of the presently disclosed subject matter results in an expression level of a target gene that is below that level observed in the presence of an inactive or attenuated DNA oligonucleotide that is unable to mediate an inhibitory response. In some embodiments, inhibition of gene expression with a DNA oligonucleotide of the presently disclosed subject matter molecule is greater in the presence of the DNA oligonucleotide than in its absence. In some embodiments, inhibition of gene expression is associated with an enhanced rate of degradation of the mRNA encoded by the gene (for example, by enzymatic cleavage mediated by a DNAzyme of the presently disclosed subject matter).

As used herein, the terms "gene" and "target gene" refer to a nucleic acid that encodes an RNA, for example, nucleic acid sequences including, but not limited to, structural genes encoding a polypeptide. The target gene can be a gene derived from a cell, an endogenous gene, a transgene, or exogenous genes such as genes of a pathogen, for example a virus, which is present in the cell after infection thereof. The cell containing the target gene can be derived from or contained in any organism, for example a plant, animal, protozoan, virus, bacterium, or fungus. The term "gene" also refers broadly to any segment of DNA associated with a biological function. As such, the term "gene" encompasses sequences including but not limited to a coding sequence, a promoter region, a transcriptional regulatory sequence, a non-expressed DNA segment that is a specific recognition sequence for regulatory proteins, a non-expressed DNA segment that contributes to gene expression, a DNA segment designed to have desired parameters, or combinations thereof. A gene can be obtained by a variety of methods, including cloning from a biological sample, synthesis based on known or predicted sequence information, and recombinant derivation of an existing sequence.

In some embodiments, a gene is a MMP gene. As used herein, a "MMP gene" is a gene for which the expression level increases during metastasis of tumor cells. In some embodiments, a MMP gene is a gene that is characterized as a member of a family of zinc-binding endopeptidases that when active can degrade one or more components of the extracellular matrix. Thus, as used herein, the term MMP gene includes all members of the MMP family including collagenases (MMP-1, MMP-8 and MMP-13), gelatinases (MMP-2 and MMP-9), stromelysins (MMP-3 and MMP-10), metalloelastase, Membrane-type MMPs (MT-MMP; MMP-14, MMP 15, MMP-16, MMP-17, MMP-24, and MMP-25), and others (MMP-7, MMP-11, MMP-12, MMP-19, MMP-20 and MMP-23).

As is understood in the art, a gene comprises a coding strand and a non-coding strand. As used herein, the terms "coding strand" and "sense strand" are used interchangeably, and refer to a nucleic acid sequence that has the same sequence of nucleotides as an mRNA from which the gene product is translated. As is also understood in the art, when the coding strand and/or sense strand is used to refer to a DNA molecule, the coding/sense strand includes thymidine residues instead of the uridine residues found in the corresponding mRNA. Additionally, when used to refer to a DNA molecule, the coding/sense strand can also include additional elements not found in the mRNA including, but not limited to promoters, enhancers, and introns. Similarly, the terms "template strand" and "antisense strand" are used interchangeably and refer to a nucleic acid sequence that is complementary to the coding/sense strand.

As used herein, the terms "complementarity" and "complementary" refer to a nucleic acid that can form one or more hydrogen bonds with another nucleic acid sequence by either traditional Watson-Crick or other non-traditional types of interactions. In reference to the nucleic molecules of the presently disclosed subject matter, the binding free energy for a nucleic acid molecule with its complementary sequence is sufficient to allow the relevant function of the nucleic acid to proceed, in some embodiments, binding with specificity by substrate binding domains of a DNAzyme of the presently disclosed subject matter such that the catalytic domain of the DNAzyme is brought in to close enough proximity with a target sequence to permit catalytic cleavage of the target sequence. The degree of complementarity between the substrate binding domains of the presently disclosed novel DNA oligonucleotides and the target region of an mRNA can vary somewhat, but no more than by what is required in order to permit the DNAzyme to cleave the target region. Determination of binding free energies for nucleic acid molecules to determine percent compelemtarity is well known in the art. See e.g., Freier et al., 1986; Turner et al., 1987.

As used herein, the phrase "percent complementarity" refers to the percentage of contiguous residues in a nucleic acid molecule that can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary, respectively). The terms "100% complementary", "fully complementary", and "perfectly complementary" indicate that all of the contiguous residues of a nucleic acid sequence can hydrogen bond with the same number of contiguous residues in a second nucleic acid sequence.

As used herein, the term "cell" is used in its usual biological sense. In some embodiments, the cell is present in an organism, for example, mammals such as humans, cows, sheep, apes, monkeys, swine, dogs, and cats. The cell can be eukaryotic (e.g., a mammalian cell, such as a human cell) or prokaryotic (e.g. a bacterium). The cell can be of somatic or germ line origin, totipotent or pluripotent, dividing or non-dividing. The cell can also be derived from or can comprise a gamete or embryo, a stem cell, or a fully differentiated cell. The cell can also be aberrant, such as a cancer cell.

The DNA oligonucleotides of the presently disclosed subject matter can be added directly to the cell, or can be complexed with cationic lipids, packaged within liposomes, or otherwise delivered to target cells or tissues. The nucleic acid or nucleic acid complexes can be locally administered to relevant tissues ex vivo, or in vivo through injection, infusion pump (e.g. an osmotic infusion pump) or stent, with or without their incorporation into biopolymers. Alternatively, the DNA oligonucleotides of the presently disclosed subject matter can be encoded by a recombinant vector (for example, a viral vector).

As used herein, the term "DNA" refers to a molecule comprising at least one deoxyribonucleotide residue. By "deoxyribonucleotide" is meant a nucleotide without a hydroxyl group and instead a hydrogen at the 2' position of a β-D-deoxyribofuranose moiety. The term encompasses double stranded DNA, single stranded DNA, DNAs with both double stranded and single stranded regions, isolated DNA such as partially purified DNA, essentially pure DNA, synthetic DNA, recombinantly produced DNA, as well as altered DNA, or analog DNA, that differs from naturally occurring DNA by the addition, deletion, substitution, and/or modification of one or more nucleotides. Such modifications can include addition of non-nucleotide material, such as to the end(s) of the DNA or internally, for example at one or more nucleotides of the DNA. The modifications can be for the purpose of increasing stability of the DNA molecule. Nucleotides in the DNA molecules of the presently disclosed subject matter can also comprise non-standard nucleotides, such as non-naturally occurring nucleotides or chemically synthesized nucleotides or deoxynucleotides. These modified DNAs can be referred to as analogs or analogs of a naturally occurring DNA.

By "DNA molecule" is meant a polymeric chain of single- or double-stranded nucleotides and also referred to herein as "oligonucleotide" and "polynucleotide. Thus, the terms DNA molecule, oligonucleotide and polynucleotide are used herein interchangeably and the use of one term or another is not intended to limit the described molecule, e.g. to a particular number of nucleotides polymerized.

As used herein, the term "RNA" refers to a molecule comprising at least one ribonucleotide residue. By "ribonucleotide" is meant a nucleotide with a hydroxyl group at the 2' position of a β-D-ribofuranose moiety. The terms encompass double stranded RNA, single stranded RNA, RNAs with both double stranded and single stranded regions, isolated RNA such as partially purified RNA, essentially pure RNA, synthetic RNA, recombinantly produced RNA, as well as altered RNA, or analog RNA, that differs from naturally occurring RNA by the addition, deletion, substitution, and/or modification of one or more nucleotides. Such modifications can include addition of non-nucleotide material, such as to the end(s) of an RNA or internally, for example at one or more nucleotides of the RNA. Nucleotides in the RNA molecules of the presently disclosed subject matter can also comprise non-standard nucleotides, such as non-naturally occurring nucleotides or chemically synthesized nucleotides or deoxynucleotides. These modified RNAs can be referred to as analogs or analogs of a naturally occurring RNA.

As used herein, the phrase "double stranded region" refers to any region of a nucleic acid molecule that is in a double stranded conformation via hydrogen bonding between the nucleotides including, but not limited to hydrogen bonding between cytosine and guanosine, adenosine and thymidine, adenosine and uracil, and any other nucleic acid duplex as would be understood by one of ordinary skill in the art. The length of the double stranded region can vary from about four consecutive basepairs to several thousand basepairs. In some embodiments, the double stranded region is at least five basepairs, in some embodiments between 5 and 30 basepairs, and in some embodiments between 5 and 15 basepairs. In some embodiments, the length of the double stranded region is selected from the group consisting of 4, 5, 6, 7, 8, 9, 10, 11, 12, 13, 14, and 15 basepairs. In some embodiments, the double stranded region comprises a first strand comprising a ribonucleotide sequence that corresponds to a coding strand of a MMP gene and a second strand comprising a deoxyribonucleotide sequence as presently disclosed herein that is complementary to the first strand, and wherein the first strand and the second strand hybridize to each other to form the double-stranded molecule.

In a representative embodiment, the length of the double stranded region is nine basepairs. As describe hereinabove, the formation of the double stranded region results from the hybridization of complementary polynucleotide strands (for example, a sense strand and an antisense strand), either via an intermolecular hybridization (i.e. involving 2 or more distinct polynucleotide molecules) or via an intramolecular hybridization, the latter of which can occur when a single polynucleotide molecule contains self-complementary regions that are capable of hybridizing to each other on the same molecule. These self-complementary regions are typically separated by a short stretch of nucleotides (for example, about 5-10 nucleotides) such that the intramolecular hybridization event forms what is referred to in the art as a "hairpin".

The enzymatic DNA oligonucleotides of the presently disclosed subject matter individually, or in combination or in conjunction with other drugs, can be used to treat diseases or conditions discussed herein. For example, to treat a particular disease or condition, the novel DNA oligonucleotides, e.g. DNAzymes, can be administered to a subject or can be introduced into other appropriate cells evident to those skilled in the art, such as for example cancer cells, individually or in combination with one or more drugs under conditions suitable for the treatment.

III. Nucleic Acids

The nucleic acid molecules, e.g. enzymatic DNA molecules, employed in accordance with the presently disclosed subject matter include any nucleic acid molecule having binding specificity for a target region of a nucleic acid (such as a mRNA) encoding a a target gene product, such as but not limited to a MMP gene product, such that binding of the DNA oligonucleotide can result in modulation of expression of the target gene produce, such but not limited to a MMP gene product. Thus, the nucleic acid molecules employed in accordance with the presently disclosed subject matter include, but are not limited to, the DNAzymes shown in SEQ ID NOs: 1-12, 22, and 29; sequences substantially identical to SEQ ID NOs: 1-12, 22, and 29; and subsequences and elongated sequences thereof. The presently disclosed subject matter also encompasses genes, cDNAs, chimeric genes, and vectors comprising disclosed nucleic acid sequences.

The term "nucleic acid molecule" refers to deoxyribonucleotides or ribonucleotides and polymers thereof in either single- or double-stranded form. Unless specifically limited, the term encompasses nucleic acids containing known analogues of natural nucleotides that have similar properties as the reference natural nucleic acid. Unless otherwise indicated, a particular nucleotide sequence also implicitly encompasses complementary sequences, subsequences, elongated sequences, as well as the sequence explicitly indicated. The terms "nucleic acid molecule" or "nucleotide sequence" can also be used in place of "gene", "DNA", "cDNA", "RNA", or "mRNA". Nucleic acids can be derived from any source, including any organism.

The term "isolated", as used in the context of a nucleic acid molecule, indicates that the nucleic acid molecule exists apart from its native environment and is not a product of nature. An isolated DNA molecule can exist in a purified form or can exist in a non-native environment such as a transgenic host cell.

The terms "identical" or percent "identity" in the context of two or more nucleotide or polypeptide sequences, refer to two or more sequences or subsequences that are the same or have a specified percentage of amino acid residues or nucleotides that are the same, when compared and aligned for maximum correspondence, as measured using one of the sequence comparison algorithms disclosed herein or by visual inspection.

The term "substantially identical", in the context of two nucleotide sequences, refers to two or more sequences or subsequences that in one example have at least about 75%, in another example about 80%, in another example about 90-95%, and in yet another example about 96%, 97%, 98%, 99%, or 100% nucleotide identity, when compared and aligned for maximum correspondence, as measured using one of the following sequence comparison algorithms (described herein below) or by visual inspection. In one example, the substantial identity exists in nucleotide sequences of at least 4 residues, in another example in nucleotide sequence of at least about 10 residues, in another example in nucleotide sequences of at least about 15 residues, in another example in nucleotide sequences of at least about 30 residues and in yet another example in nucleotide sequences comprising complete coding sequences.

In one aspect, polymorphic sequences can be substantially identical sequences. The terms "polymorphic", "polymorphism", and "polymorphic variants" refer to the occurrence of two or more genetically determined alternative sequences or alleles in a population. An allelic difference can be as small as one base pair. As used herein in regards to a nucleotide or polypeptide sequence, the term "substantially identical" also refers to a particular sequence that varies from another sequence by one or more deletions, substitutions, or additions, the net effect of which is to retain biological activity of a gene, gene product, or sequence of interest.

For sequence comparison, typically one sequence acts as a reference sequence to which test sequences are compared. When using a sequence comparison algorithm, test and reference sequences are entered into a computer program, subsequence coordinates are designated if necessary, and sequence algorithm program parameters are selected. The sequence comparison algorithm then calculates the percent sequence identity for the designated test sequence(s) relative to the reference sequence, based on the selected program parameters.

Optimal alignment of sequences for comparison can be conducted, e.g., by the local homology algorithm of Smith & Waterman, 1981, by the homology alignment algorithm of Needleman & Wunsch, 1970, by the search for similarity method of Pearson & Lipman, 1988, by computerized implementations of these algorithms (GAP, BESTFIT, FASTA, and TFASTA, in the Wisconsin Genetics Software Package, available from Accelrys Inc., San Diego, Calif., United States of America), or by visual inspection. See generally, Ausubel, 1995.

In some embodiments, an algorithm for determining percent sequence identity and sequence similarity is the BLAST algorithm, which is described by Altschul et al., 1990. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLAST N program (for nucleotide sequences) uses as defaults a wordlength W=11, an expectation E=10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See Henikoff & Henikoff, 1992.

In addition to calculating percent sequence identity, the BLAST algorithm also performs a statistical analysis of the similarity between two sequences. See e.g., Karlin & Altschul, 1993. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is in some embodiments less than about 0.1, in some embodiments less than about 0.01, and in some embodiments less than about 0.001.

Another indication that two nucleotide sequences are substantially identical is that the two molecules specifically or substantially hybridize to each other under stringent conditions. In the context of nucleic acid hybridization, two nucleic acid sequences being compared can be designated a "probe" and a "target". A "probe" is a reference nucleic acid molecule, and a "target" is a test nucleic acid molecule, often found within a heterogeneous population of nucleic acid molecules. A "target sequence" is synonymous with a "test sequence".

An exemplary nucleotide sequence employed in the methods disclosed herein comprises sequences, e.g. a substrate binding domain, that are complementary to a target region of a target nucleic acid encoding a target polypeptide, such as but not limited to an mRNA encoding a MMP, the complementary regions being capable of forming a duplex of in some embodiments at least about 4 to 30 basepairs. In some embodiments one strand of the duplex comprises a nucleic acid sequence of at least 4 contiguous bases having a nucleic acid sequence of a nucleic acid molecule of the presently disclosed subject matter (for example, SEQ ID NOs:1-12, 22, and 29). In one example, one strand of the duplex comprises a nucleic acid sequence comprising 4 to 10 nucleotides, or even longer where desired, such as 11, 12, 13, 14, 15, 16, 17, 18, 19, or 20 nucleotides or up to the full length of any of those set forth as SEQ ID NOs:1-12, 22, and 29. Such fragments can be readily prepared by, for example, directly synthesizing the fragment by chemical synthesis, by application of nucleic acid amplification technology, or by introducing selected sequences into recombinant vectors for recombinant production. The phrase "hybridizing specifically to" or "binding specificity" can refer to the binding, duplexing, or hybridizing of a molecule only to a particular nucleotide sequence under stringent conditions when that sequence is present in a complex nucleic acid mixture (e.g., total cellular DNA or RNA)

The phrase "hybridizing substantially to" refers to complementary hybridization between a probe nucleic acid molecule and a target nucleic acid molecule and embraces minor mismatches that can be accommodated by reducing the stringency of the hybridization media to achieve the desired hybridization.

"Stringent hybridization conditions" and "stringent hybridization wash conditions" in the context of nucleic acid hybridization experiments such as Southern and Northern blot analysis are both sequence- and environment-dependent. Longer sequences hybridize specifically at higher temperatures. An extensive guide to the hybridization of nucleic acids is found in Tijssen, 1993. Generally, highly stringent hybridization and wash conditions are selected to be about 5° C. lower than the thermal melting point ($T_m$) for the specific sequence at a defined ionic strength and pH. Typically, under "stringent conditions" a probe will hybridize specifically to its target subsequence, but to no other sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of highly stringent hybridization conditions for Southern or Northern Blot analysis of complementary nucleic acids having more than about 100 complementary residues is overnight hybridization in 50% formamide with 1 mg of heparin at 42° C. An example of highly stringent wash conditions is 15 minutes in 0.1× standard saline citrate (SSC), 0.1% (w/v) SDS at 65° C. Another example of highly stringent wash conditions is 15 minutes in 0.2×SSC buffer at 65° C. (see Sambrook and Russell, 2001 for a description of SSC buffer and other stringency conditions). Often, a high stringency wash is preceded by a lower stringency wash to remove background probe signal. An example of medium stringency wash conditions for a duplex of more than about 100 nucleotides is 15 minutes in 1×SSC at 45° C. Another example of medium stringency wash for a duplex of more than about 100 nucleotides is 15 minutes in 4-6×SSC at 40° C. For short probes (e.g., about 10 to 50 nucleotides), stringent conditions typically involve salt concentrations of less than about 1 M $Na^+$ ion, typically about 0.01 to 1 M $Na^+$ ion concentration (or other salts) at pH 7.0-8.3, and the temperature is typically at least about 30° C. Stringent conditions can also be achieved with the addition of destabilizing agents such as formamide. In general, a signal to noise ratio of 2-fold or higher than that observed for an unrelated probe in the particular hybridization assay indicates detection of a specific hybridization.

The following are examples of hybridization and wash conditions that can be used to clone homologous nucleotide sequences that are substantially identical to reference nucleotide sequences of the presently disclosed subject matter: a probe nucleotide sequence hybridizes in one example to a target nucleotide sequence in 7% sodium dodecyl sulfate (SDS), 0.5M $NaPO_4$, 1 mm EDTA at 50° C. followed by washing in 2×SSC, 0.1% SDS at 50° C.; in another example, a probe and target sequence hybridize in 7% sodium dodecyl sulfate (SDS), 0.5M $NaPO_4$, 1 mm EDTA at 50° C. followed by washing in 1×SSC, 0.1% SDS at 50° C.; in another example, a probe and target sequence hybridize in 7% sodium dodecyl sulfate (SDS), 0.5M $NaPO_4$, 1 mm EDTA at 50° C. followed by washing in 0.5×SSC, 0.1% SDS at 50° C.; in another example, a probe and target sequence hybridize in 7% sodium dodecyl sulfate (SDS), 0.5M $NaPO_4$, 1 mm EDTA at 50° C. followed by washing in 0.1×SSC, 0.1% SDS at 50° C.; in yet another example, a probe and target sequence hybridize in 7% sodium dodecyl sulfate (SDS), 0.5M $NaPO_4$, 1 mm EDTA at 50° C. followed by washing in 0.1×SSC, 0.1% SDS at 65° C.

The term "subsequence" refers to a sequence of nucleic acids that comprises a part of a longer nucleic acid sequence. An exemplary subsequence is a sequence that comprises part of a region of an enzymatic DNA molecule (e.g. a substrate binding domain), which is complementary to at least a portion of (e.g. a target region) the sequence of a target nucleic acid, such as a mRNA.

The term "elongated sequence" refers to an addition of nucleotides (or other analogous molecules) incorporated into the nucleic acid. For example, a polymerase (e.g., a DNA polymerase) can add sequences at the 3' terminus of the nucleic acid molecule. In addition, the nucleotide sequence can be combined with other DNA sequences, such as promoters, promoter regions, enhancers, polyadenylation signals, intronic sequences, additional restriction enzyme sites, multiple cloning sites, and other coding segments.

The terms "operatively linked" and "operably linked", as used herein, refer to a promoter region that is connected to a nucleotide sequence in such a way that the transcription of that nucleotide sequence is controlled and regulated by that promoter region. Similarly, a nucleotide sequence is said to be under the "transcriptional control" of a promoter to which it is operably linked. Techniques for operatively linking a promoter region to a nucleotide sequence are known in the art.

The terms "heterologous gene", "heterologous DNA sequence", "heterologous nucleotide sequence", "exogenous nucleic acid molecule", or "exogenous DNA segment", as used herein, each refer to a sequence that originates from a source foreign to an intended host cell or, if from the same source, is modified from its original form. Thus, a heterologous gene in a host cell includes a gene that is endogenous to the particular host cell but has been modified, for example by mutagenesis or by isolation from native transcriptional regulatory sequences. The terms also include non-naturally occurring multiple copies of a naturally occurring nucleotide sequence. Thus, the terms refer to a DNA segment that is foreign or heterologous to the cell, or homologous to the cell but in a position within the host cell nucleic acid wherein the element is not ordinarily found.

The term "expression vector" as used herein refers to a DNA sequence capable of directing expression of a particular nucleotide sequence in an appropriate host cell, comprising a promoter operatively linked to the nucleotide sequence of interest which is operatively linked to termination signals. It also typically comprises sequences required for proper translation of the nucleotide sequence. The construct comprising the nucleotide sequence of interest can be chimeric. The construct can also be one that is naturally occurring but has been obtained in a recombinant form useful for heterologous expression.

The term "promoter" or "promoter region" each refers to a nucleotide sequence within a gene that is positioned 5' to a coding sequence of a same gene and functions to direct transcription of the coding sequence. The promoter region comprises a transcriptional start site, and can additionally include one or more transcriptional regulatory elements. In some embodiments, a method of the presently disclosed subject matter employs a hypoxia inducible promoter.

A "minimal promoter" is a nucleotide sequence that has the minimal elements required to enable basal level transcription to occur. As such, minimal promoters are not complete promoters but rather are subsequences of promoters that are capable of directing a basal level of transcription of a reporter construct in an experimental system. Minimal promoters include but are not limited to the CMV minimal promoter, the HSV-tk minimal promoter, the simian virus 40 (SV40) minimal promoter, the human β-actin minimal promoter, the human EF2 minimal promoter, the adenovirus E1B minimal promoter, and the heat shock protein (hsp) 70 minimal promoter. Minimal promoters are often augmented with one or more transcriptional regulatory elements to influence the transcription of an operably linked gene. For example, cell-type-specific or tissue-specific transcriptional regulatory elements can be added to minimal promoters to create recombinant promoters that direct transcription of an operably linked nucleotide sequence in a cell-type-specific or tissue-specific manner Different promoters have different combinations of transcriptional regulatory elements. Whether or not a gene is expressed in a cell is dependent on a combination of the particular transcriptional regulatory elements that make up the gene's promoter and the different transcription factors that are present within the nucleus of the cell. As such, promoters are often classified as "constitutive", "tissue-specific", "cell-type-specific", or "inducible", depending on their functional activities in vivo or in vitro. For example, a constitutive promoter is one that is capable of directing transcription of a gene in a variety of cell types. Exemplary constitutive promoters include the promoters for the following genes which encode certain constitutive or "housekeeping" functions: hypoxanthine phosphoribosyl transferase (HPRT), dihydrofolate reductase (DHFR; (Scharfmann et al., 1991), adenosine deaminase, phosphoglycerate kinase (PGK), pyruvate kinase, phosphoglycerate mutase, the β-actin promoter (see, e.g. Williams et al., 1993), and other constitutive promoters known to those of skill in the art. "Tissue-specific" or "cell-type-specific" promoters, on the other hand, direct transcription in some tissues and cell types but are inactive in others. Exemplary tissue-specific promoters include the PSA promoter (Yu et al., 1999; Lee et al., 2000), the probasin promoter (Greenberg et al., 1994; Yu et al., 1999), and the MUC1 promoter (Kurihara et al., 2000) as discussed above, as well as other tissue-specific and cell-type specific promoters known to those of skill in the art.

When used in the context of a promoter, the term "linked" as used herein refers to a physical proximity of promoter elements such that they function together to direct transcription of an operably linked nucleotide sequence The term "transcriptional regulatory sequence" or "transcriptional regulatory element", as used herein, each refers to a nucleotide sequence within the promoter region that enables responsiveness to a regulatory transcription factor. Responsiveness can encompass a decrease or an increase in transcriptional output and is mediated by binding of the transcription factor to the DNA molecule comprising the transcriptional regulatory element.

The term "transcription factor" generally refers to a protein that modulates gene expression by interaction with the transcriptional regulatory element and cellular components for transcription, including RNA Polymerase, Transcription Associated Factors (TAFs), chromatin-remodeling proteins, and any other relevant protein that impacts gene transcription.

The terms "reporter gene" or "marker gene" or "selectable marker" each refer to a heterologous gene encoding a product that is readily observed and/or quantitated. A reporter gene is heterologous in that it originates from a source foreign to an intended host cell or, if from the same source, is modified from its original form. Non-limiting examples of detectable reporter genes that can be operatively linked to a transcriptional regulatory region can be found in Alam & Cook, 1990 and PCT International Publication No. WO 97/47763. Exemplary reporter genes for transcriptional analyses include the lacZ gene (see e.g., Rose & Botstein, 1983), Green Fluorescent Protein (GFP; Cubitt et al., 1995), luciferase, and chloramphenicol acetyl transferase (CAT). Reporter genes for methods to produce transgenic animals include but are not limited to antibiotic resistance genes, for example the antibiotic resistance gene confers neomycin resistance. Any suitable reporter and detection method can be used, and it will be appreciated by one of skill in the art that no particular choice is essential to or a limitation of the presently disclosed subject matter.

An amount of reporter gene can be assayed by any method for qualitatively or quantitatively determining presence or activity of the reporter gene product. The amount of reporter gene expression directed by each test promoter region fragment is compared to an amount of reporter gene expression to a control construct comprising the reporter gene in the absence of a promoter region fragment. A promoter region fragment is identified as having promoter activity when there is significant increase in an amount of reporter gene expression in a test construct as compared to a control construct. The term "significant increase", as used herein, refers to an quantified change in a measurable quality that is larger than the margin of error inherent in the measurement technique, in one example an increase by about 2-fold or greater relative to a control measurement, in another example an increase by about 5-fold or greater, and in yet another example an increase by about 10-fold or greater.

The presently disclosed subject matter includes in some embodiments viral vectors, including but not limited to adenovirus vectors, comprising the disclosed nucleotide sequences. The term "vector", as used herein refers to a DNA molecule having sequences that enable the transfer of those sequences to a compatible host cell. A vector also includes nucleotide sequences to permit ligation of nucleotide sequences within the vector, wherein such nucleotide sequences are also replicated in a compatible host cell. A vector can also mediate recombinant production of a therapeutic polypeptide, as described further herein below.

Nucleic acids of the presently disclosed subject matter can be cloned, synthesized, recombinantly altered, mutagenized, or combinations thereof. Standard recombinant DNA and molecular cloning techniques used to isolate nucleic acids are known in the art. Exemplary, non-limiting methods are described by Silhavy et al., 1984; Ausubel et al., 1992; Glover & Hames, 1995; and Sambrook & Russell, 2001). Site-specific mutagenesis to create base pair changes, deletions, or small insertions is also known in the art as exemplified by publications (see e.g., Adelman et al., 1983; Sambrook & Russell, 2001).

III.A. Enzymatic Nucleic Acids

Because of their sequence-specificity, enzymatic nucleic acid molecules show promise as therapeutic agents for human disease (Usman & McSwiggen, 1995; Christoffersen and Marr, 1995 J). Enzymatic nucleic acid molecules can be designed to cleave specific RNA targets within the background of cellular RNA. Such a cleavage event renders the RNA non-functional and abrogates protein expression from that RNA. In this manner, synthesis of a protein associated with a disease state can be selectively inhibited.

In general, enzymatic nucleic acids act by first binding to a target nucleic acid, such as a target RNA. Such binding occurs through the substrate binding domain of an enzymatic nucleic acid which is held in close proximity to a catalytic domain of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA destroys its ability to direct synthesis of an encoded protein. After an enzymatic nucleic acid has bound and cleaved its RNA target, it is released from that RNA to search for another target and can repeatedly bind and cleave new targets.

The presently disclosed subject matter provides in some embodiments an isolated enzymatic DNA molecule comprising a polynucleotide sequence having binding specificity for a target region of a mRNA encoding a MMP. In some embodiments, the MMP is MMP-2 or MMP-9.

In some embodiments, the enzymatic DNA molecule is a DNAzyme. Further, in some embodiments, the enzymatic DNA molecule comprises a catalytic domain flanked on each side by substrate binding domains each having binding specificity for a distinct nucleotide sequence of the target region.

In particular embodiments, the enzymatic DNA molecule of the presently disclosed subject matter has a nucleotide sequence comprising the sequence of SEQ ID NOs:1-12, 22, and 29.

The substrate binding domain of an enzymatic DNA molecule of the presently disclosed subject matter typically comprises two nucleotide sequences flanking a catalytic domain, and typically each substrate binding domain contains a sequence of at least about 4 to about 30 bases, preferably about 6 to about 15 bases, which are capable of hybridizing to a complementary sequence of bases within the substrate nucleic acid giving the enzymatic DNA molecule its high sequence specificity. Modification or mutation of the recognition site as discussed herein and via well-known methods (see, e.g., Joyce et al., 1989) allows one to alter the sequence specificity of an enzymatic nucleic acid molecule.

In one disclosed embodiment, a DNA oligonucleotide, i.e. an enzymatic DNA molecule, of the presently disclosed subject matter comprises a conserved core catalytic domain flanked on each side by a substrate binding domain that each interact with the substrate RNA at a target region through base-pairing interactions. In various embodiments, the conserved core comprises one or more conserved sequences as disclosed herein. In some embodiments the conserved core can comprise a substitution in a conserved sequence as disclosed herein, but wherein intramolecular interactions are preserved by the substitution. In some embodiments, the enzymatic DNA molecule further comprises a "spacer" region (or sequence) between the regions (or sequences) involved in base pairing. In still another variation, the conserved core is "interrupted" at various intervals by one or more less-conserved variable or "spacer" nucleotides.

By "catalytic domain" is meant that portion/region of the enzymatic nucleic acid molecule essential for cleavage of a nucleic acid substrate.

By "substrate binding domain" is meant that portion/region of an enzymatic DNA molecule that exhibits binding specificity for a target nucleic acid, also referred to as a substrate. In some embodiments, "binding specificity", "corresponds to", "corresponding to", and grammatical variations thereof refer to the substrate binding domain being identical to or complementary to (i.e., able to base-pair with) a portion of its substrate. Such identity or complementarity can be 100%, but can be less if desired. For example, as few as 75% of the bases can be identical or base-paired in some embodiments over a given stretch of sequences in the substrate binding domain, and as few as 90% of the bases can be identical or base-paired in other embodiments. In some embodiments, 95%, 96%, 97%, 98%, or 99% of the bases can be identical or base-paired. That is, in some embodiments these domains contain sequences within an enzymatic nucleic acid molecule that are intended to bring enzymatic DNA molecule and target together through complementary base-pairing interactions.

As used herein, then, the term "having binding specificity to" and grammatical variants thereof can refer to a nucleotide sequence that is 100% identical or complementary to at least four contiguous nucleotides of a nucleic acid sequence of a target gene, such as but not limited to a MMP gene. Thus, in some embodiments, a first nucleic acid sequence, e.g. a substrate binding domain of a novel DNAzyme disclosed herein, that has binding specificity for a coding strand of a MMP gene or an mRNA transcribed from the coding strand is a nucleic acid sequence that is 100% identical or complementary to at least four contiguous nucleotides of a MMP gene or its transcribed mRNA, including, but not limited to 5' untranslated sequences, exon sequences, intron sequences, and 3' untranslated sequences.

The enzymatic nucleic acid molecules of the presently disclosed subject matter can have substrate binding domains that are contiguous or non-contiguous and can be varying lengths. The length of each substrate binding domain is preferably greater than or equal to four nucleotides; specifically 5-30 nucleotides; more specifically 5-15 nucleotides long. If two substrate binding domains are chosen, the design can optionally be such that the length of the binding domains are symmetrical (i.e., each of the binding domains is of the same length; e.g., seven and seven nucleotides, eight and eight nucleotides, or nine and nine nucleotides long) or asymmetrical (i.e., the binding domains are of different length; e.g., six and three nucleotides; three and six nucleotides long; four and five nucleotides long; four and six nucleotides long; four and seven nucleotides long; and the like).

Enzymatic DNA molecules of the presently disclosed subject matter also include those with altered substrate binding domains. In various embodiments, these altered binding domains confer unique sequence specificities on the enzymatic DNA molecule including such binding domains. The exact bases present in the substrate binding domain determine the base sequence at which cleavage will take place. Cleavage of the substrate nucleic acid occurs within the target region determined by the specificity of the substrate binding domain. This cleavage leaves a 2', 3', or 2',3'-cyclic phosphate group on the substrate cleavage sequence and a 5' hydroxyl on the nucleotide that was originally immediately 3' of the substrate cleavage sequence in the original substrate. Cleavage can be redirected to a site of choice by changing the bases present in the substrate binding domain. See Murphy et al., 1989.

The enzymatic nature of an enzymatic DNA molecule has significant advantages, such as the concentration of enzymatic DNA molecules necessary to affect a therapeutic treatment is lower. This advantage reflects the ability of the enzymatic DNA molecules to act enzymatically. Thus, a single enzymatic DNA molecule is able to cleave many molecules of target RNA. In addition, the enzymatic DNA molecule is a highly specific inhibitor, with the specificity of inhibition depending not only on the base-pairing mechanism of binding to the target RNA, but also on the mechanism of target RNA cleavage. Single mismatches, or base-substitutions, near the site of cleavage can be chosen to completely eliminate catalytic activity of enzymatic nucleic acid molecules.

III.B. Synthesis of Nucleic Acid Molecules

In one aspect, the presently disclosed subject matter provides an enzymatic DNA molecule that has been synthesized outside of a target cell prior to introduction of the DNA molecule into the target cell. In this embodiment, the synthesis can be performed either mechanically (i.e., using a DNA synthesis machine) or using recombinant techniques.

Mechanical synthesis of nucleic acids greater than 100 nucleotides in length is difficult using automated methods, and the cost of such molecules tends to be prohibitive. As used herein, small nucleic acid motifs ("small" referring to nucleic acid motifs in some embodiments no more than 100 nucleotides in length, in some embodiments no more than 80 nucleotides in length, and in some embodiments no more than 50 nucleotides in length; e.g., individual DNA oligonucleotide sequences or DNA sequences synthesized in tandem) can be used for exogenous delivery. The simple structure of these molecules increases the ability of the nucleic acid to invade targeted regions of protein and/or RNA structure.

Exemplary molecules of the presently disclosed subject matter are chemically synthesized, and others can similarly be synthesized.

Oligonucleotides (e.g., certain modified oligonucleotides or portions of oligonucleotides lacking deoxyribonucleotides) are synthesized using protocols known in the art. See e.g., Caruthers et al, 1992; PCT International Publication No. WO 99/54459; Wincott et al., 1995; Wincott & Usman, 1997; Brennan et al., 1998; and U.S. Pat. No. 6,001,311, each of which is incorporated herein by reference. The synthesis of oligonucleotides makes use of common nucleic acid protecting and coupling groups, such as dimethoxytrityl at the 5'-end, and phosphoramidites at the 3'-end. In a non-limiting example, small-scale syntheses can be conducted on a Applied Biosystems 3400 DNA Synthesizer (Applied Biosystems Inc., Foster City, Calif., United States of America) using a 0.2 lμmol scale protocol with a 2.5 minute coupling step for 2'-O-methylated nucleotides and a 45 second coupling step for 2'-deoxy nucleotides or 2'-deoxy-2'-fluoro nucleotides. Alternatively, syntheses at the 0.2 μmol scale can be performed on a 96-well plate synthesizer. A 33-fold excess (60 μL of 0.11 M; 6.6 μmol) of 2'-O-methyl phosphoramidite and a 105-fold excess of S-ethyl tetrazole (60 μL of 0.25 M; 15 μmol) can be used in each coupling cycle of 2'-O-methyl residues relative to polymer-bound 5'-hydroxyl. A 22-fold excess (40 μL of 0.11 M; 4.4 μmol) of deoxy phosphoramidite and a 70-fold excess of S-ethyl tetrazole (40 μL of 0.25 M; 10 μmol) can be used in each coupling cycle of deoxy residues relative to polymer-bound 5'-hydroxyl. Average coupling yields on the Applied Biosystems 3400 DNA Synthesizer, determined by calorimetric quantitation of the trityl fractions, are typically 97.5-99%. Other oligonucleotide synthesis reagents for the Applied Biosystems 3400 DNA Synthesizer include the following: detritylation solution is 3% TCA in methylene chloride (Applied Biosystems, Inc.); capping is performed with 16% N-methyl imidazole in THF (Applied Biosystems, Inc.) and 10% acetic anhydride/10% 2,6-lutidine in THF (Applied Biosystems, Inc.); and oxidation solution is 16.9 mM $I_2$, 49 mM pyridine, 9% water in THF (PERSEPTIVE™). Burdick & Jackson Synthesis Grade acetonitrile is used directly from the reagent bottle. S-Ethyltetrazole solution (0.25 M in acetonitrile) is made up from the solid obtained from American International Chemical, Inc. Alternately, for the introduction of phosphorothioate internucleotide linkages, Beaucage reagent ($^3$H-1,2-benzodithiol-3-one 1,1-dioxide, 0.05 M in acetonitrile) is used.

Deprotection of the DNA-based oligonucleotides is performed as follows: the polymer-bound trityl-on oligoribonucleotide is transferred to a 4 mL glass screw top vial and suspended in a solution of 40% aqueous methylamine (1 mL) at 65° C. for 10 minutes. After cooling to −20° C., the supernatant is removed from the polymer support. The support is washed three times with 1.0 mL of EtOH:MeCN:H₂O (3:1:1), vortexed, and the supernatant is added to the first supernatant. The combined supernatants, containing the oligoribonucleotide, are dried to a white powder.

In some embodiments, the method of synthesis used for DNA including certain DNA molecules of the presently disclosed subject matter follows the procedure as described in Usman et al., 1987; Scaringe et al., 1990; Wincott et al., 1995; Wincott & Usman, 1997; and makes use of common nucleic acid protecting and coupling groups, such as dimethoxytrityl at the 5'-end, and phosphoramidites at the 3'-end. In a non-limiting example, small-scale syntheses are conducted on an Applied Biosystems 3400 DNA Synthesizer using a 0.2 μmol scale protocol with a 7.5 minute coupling step for alkylsilyl protected nucleotides and a 2.5 minute coupling step for 2'-O-methylated nucleotides. Alternatively, syntheses at the 0.2 μmol scale can be done on a 96-well plate synthesizer. A 33-fold excess (60 μL of 0.11 M; 6.6 μmol) of 2'-O-methyl phosphoramidite and a 75-fold excess of S-ethyl tetrazole (60 μL of 0.25 M; 15 μmol) can be used in each coupling cycle of 2'-O-methyl residues relative to polymer-bound 5'-hydroxyl. A 66-fold excess (120 μL of 0.11 M; I 13.2 μmol) of alkylsilyl (ribo) protected phosphoramidite and a 150-fold excess of S-ethyl tetrazole (120 μL of 0.25 M; 30 μmol) can be used in each coupling cycle of residues relative to polymer-bound 5'-hydroxyl. Average coupling yields on the Applied Biosystems 3400 DNA Synthesizer, determined by calorimetric quantitation of the trityl fractions, are typically 97.5-99%. Other oligonucleotide synthesis reagents for the Applied Biosystems 3400 DNA Synthesizer include the following: detritylation solution is 3% TCA in methylene chloride (Applied Biosystems, Inc.); capping is performed with 16% N-methyl imidazole in THF (Applied Biosystems, Inc.) and 10% acetic anhydride/10% 2,6-lutidine in THF (Applied Biosystems, Inc.); oxidation solution is 16.9 mM $I_2$, 49 mM pyridine, 9% water in THF (PERSEPTIVE™). Burdick & Jackson Synthesis Grade acetonitrile is used directly from the reagent bottle. S-Ethyltetrazole solution (0.25 M in acetonitrile) is made up from the solid obtained from American International Chemical, Inc. (Natick, Mass., United States of America). Alternately, for the introduction of phosphorothioate linkages, Beaucage reagent ($^3$H-1,2-Benzodithiol-3-one 1,1-dioxide 0.05 M in acetonitrile) is used.

Deprotection of the RNA can be performed, for example, using either a two-pot or one-pot protocol. For the two-pot protocol, the polymer-bound trityl-on oligoribonucleotide is transferred to a 4 mL glass screw top vial and suspended in a solution of 40% aqueous methylamine (1 mL) at 65° C. for 10 minutes. After cooling to −20° C., the supernatant is removed from the polymer support. The support is washed three times with 1.0 mL of EtOH:MeCN:H₂O (3:1:1), vortexed, and the supernatant is then added to the first supernatant. The combined supernatants, containing the oligonucleotide, are dried to a white powder. The base deprotected oligonucleotide is resuspended in anhydrous TEA/HF/NMP solution (300 μL of a solution of 1.5 mL N-methylpyrrolidinone, 750 μL TEA and 1 mL TEA·3HF to provide a 1.4 M HF concentration) and heated to 65° C. After 1.5 hours, the oligomer is quenched with 1.5 M $NH_4HCO_3$.

Alternatively, for the one-pot protocol, the polymer-bound trityl-on oligonucleotide is transferred to a 4 mL glass screw top vial and suspended in a solution of 33% ethanolic methylamine:DMSO (1:1; 0.8 mL) at 65° C. for 15 minutes. The vial is brought to room temperature, TEA·3HF (0.1 mL) is added, and the vial is heated at 65° C. for 15 minutes. The sample is cooled at −20° C., and then quenched with 1.5 M $NH_4HCO_3$.

For purification of the trityl-on oligomers, the quenched $NH_4HCO_3$ solution is loaded onto a C-18 containing cartridge that had been prewashed with acetonitrile followed by 50 mM TEAA. After washing the loaded cartridge with water, the RNA is detritylated with 0.5% trifluoroacetic acid (TFA) for 13 min. The cartridge is then washed again with water, salt exchanged with 1 M NaCl, and washed with water again. The oligonucleotide is then eluted with 30% acetonitrile.

The average stepwise coupling yields are typically greater than 98% (Wincott et al., 1995). Those of ordinary skill in the art will recognize that the scale of synthesis can be adapted to be larger or smaller than the example described above including but not limited to 96-well format: all that is important is the ratio of chemicals used in the reaction.

Alternatively, the nucleic acid molecules of the presently disclosed subject matter can be synthesized separately and joined together post-synthetically, for example, by ligation (PCT International Publication No. WO 93/23569; Shabarova et al., 1991; Bellon et al., 1997), or by hybridization following synthesis and/or deprotection.

The nucleic acid molecules of the presently disclosed subject matter can be modified extensively to enhance stability by modification with nuclease resistant groups including, but not limited to 2'-amino, 2'-C-allyl, 2'-fluoro, 2'-O-methyl, 2'-H (for a review see Usman & Cedergren, 1992; Usman et al., 1994). siRNA constructs can be purified by gel electrophoresis using general methods or can be purified by high pressure liquid chromatography (HPLC; see Wincott et al., 1995, the totality of which is hereby incorporated herein by reference) and re-suspended in water.

In some embodiments, recombinant techniques can be used to synthesize an enzymatic DNA molecule, which can thereafter be purified from the source and transferred to a target cell. There are many techniques that are known in the art for the synthesis of DNA molecules in recombinant cells, and any such technique can be used in the practice of the presently disclosed subject matter. One such general strategy for synthesizing a DNA molecule includes cloning a DNA sequence downstream of a bacterial or yeast origin of replication and introducing the recombinant molecule into a cell in which the origin of replication is competent to direct replication of the cloned sequence. This can be accomplished using a plasmid constructed for this purpose.

III.C. Optimizing Activity of Nucleic Acid Molecules

In various embodiments, an enzymatic DNA molecule of the presently disclosed subject matter can combine one or more modifications or mutations including additions, deletions, and substitutions. In alternative embodiments, such mutations or modifications can be generated using methods that produce random or specific mutations or modifications. These mutations or modifications can, for example, change the length of, or alter the nucleotide sequence of, a loop, a spacer region or the substrate binding domain or add one or more non-nucleotide moieties to the molecule to increase stability, for example. In some embodiments, one or more mutations within one catalytically active enzymatic DNA molecule can be combined with the mutation(s) within a second catalytically active enzymatic DNA molecule to produce a new enzymatic DNA molecule containing the mutations of both molecules.

It is also to be understood that an enzymatic DNA molecule of the presently disclosed subject matter can comprise enzymatically active portions (e.g. catalytic domains) of a DNAzyme or can comprise a DNAzyme with one or more mutations, e.g., with one or more substrate binding domain sequences or spacers absent or modified, as long as such deletions, additions or modifications do not adversely impact the molecule's ability to perform as an enzyme.

Alternatively, in some embodiments mutations can be introduced in the enzymatic DNA molecule by altering the length of the substrate binding domains of the enzymatic DNA molecule. The substrate binding domains of the enzymatic DNA molecule have binding specificity for and associate with a complementary sequence of bases within a target region of a substrate nucleic acid sequence. Methods of altering the length of the recognition domains are known in the art and include direct synthesis and PCR, for example.

Alteration of the length of the recognition domains of an enzymatic DNA molecule can have a desirable effect on the binding specificity of the enzymatic DNA molecule. For example, an increase in the length of the substrate binding domains can increase binding specificity between the enzymatic DNA molecule and the complementary base sequences of a target region in a substrate polynucleotide, or can enhance recognition of a particular sequence in a hybrid substrate. In addition, an increase in the length of the substrate binding domains can also increase the affinity with which the DNA molecule binds to the polynucleotide substrate. In various embodiments, these altered substrate binding domains in the enzymatic DNA molecule confer increased binding specificity and affinity between the enzymatic DNA molecule and its substrate, however, it may decrease catalytic efficiency of the DNAzyme. Therefore, one of skill in the art will appreciate that alteration of the length of the recognition domains is a balance of optimal binding and catalytic activity.

Therapeutic nucleic acid molecules of the presently disclosed subject matter (e.g., enzymatic DNA molecules including DNAzymes) delivered exogenously are optimally stable within cells until translation of the target RNA has been inhibited long enough to reduce the levels of the undesirable protein. This period of time varies between hours to days depending upon the disease state. Although DNAzymes as described herein are considered advantageous over RNA based molecules in that DNAzymes are less sensitive to degradation, in some embodiments it is desirable to further increase stability of the DNAzymes of the presently disclosed subject matter. Improvements in the chemical synthesis of nucleic acid molecules described in the presently disclosed subject matter and in the art (Wincott et al., 1995; Caruthers et al., 1992) have expanded the ability to modify nucleic acid molecules by introducing nucleotide modifications to enhance their nuclease stability.

Therefore, enzymatic DNA molecules having chemical modifications that maintain or enhance enzymatic activity are provided. Such nucleic acid molecules are generally more resistant to nucleases than unmodified nucleic acid molecules. Thus, in a cell and/or in vivo the activity may not be significantly lowered. As exemplified herein, such enzymatic nucleic acid molecules are useful in a cell and/or in vivo even if activity over all is reduced 10-fold. Such enzymatic nucleic acid molecules herein are said to "maintain" the enzymatic activity.

As described briefly above, chemically synthesizing nucleic acid molecules incorporating various modifications (e.g. to base, sugar, and/or phosphate moieties) can reduce the degradation of the nucleic acid molecules by nucleases present in biological fluids, and can thus can increase the potency of therapeutic nucleic acid molecules (see e.g., PCT International Publication Nos. WO 92/07065, WO 93/15187, and WO 91/03162; U.S. Pat. Nos. 5,334,711 and 6,300,074; Perrault et al., 1990; Pieken et al., 1991; Usman & Cedergren, 1992; and Burgin et al., 1996; all of which are incorporated by reference herein). Each of the above references describe various chemical modifications that can be made to the base, phosphate, and/or sugar moieties of the nucleic acid molecules described herein. Modifications can be employed to enhance the efficacy of the disclosed nucleic acid molecules in cells and/or in vivo.

There are several examples in the art describing sugar, base, and phosphate modifications that can be introduced into nucleic acid molecules with significant enhancement in their nuclease stability and efficacy. For example, oligonucleotides can be modified to enhance their stability and/or enhance biological activity by modification with nuclease resistant groups, for example, 2'-amino, 2'-C-allyl, 2'-fluoro, 2'-O-methyl, 2'-O-allyl, 2'-H, nucleotide base modifications (reviewed in Usman & Cedergren, 1992; Usman et al., 1994; Burgin et al., 1996). Sugar modification of nucleic acid molecules have been extensively described in the art (see PCT International Publication Nos. WO 92/07065, WO 93/15187, WO 98/13526, and WO 97/26270; U.S. Pat. Nos. 5,334,711; 5,716,824; and 5,627,053; Perrault et al., 1990; Pieken et al., 1991; Usman & Cedergren, 1992; Beigelman et al., 1995; Karpeisky et al., 1998; Earnshaw & Gait, 1998; Verma & Eckstein, 1998; Burlina et al., 1997; all of which are incorporated by reference herein). Such publications describe general methods and strategies to determine the location of incorporation of sugar, base, and/or phosphate modifications and the like into nucleic acid molecules without modulating catalysis. In view of such teachings, similar modifications can be used as described herein to modify the enzymatic DNA molecules of the presently disclosed subject matter so long as the ability of the DNA molecules to maintain binding specificity to the substrate and catalytic activity is not significantly inhibited.

While chemical modification of oligonucleotide by internucleotide linkages with phosphorothioate and/or 5'-methylphosphonate linkages improves stability, excessive modifications can cause toxicity or decreased activity. Therefore, when designing nucleic acid molecules, the number of these internucleotide linkages should be minimized. Reducing the concentration of these linkages should lower toxicity, resulting in increased efficacy and higher specificity of these molecules.

Universal bases can also be employed in the nucleic acids of the presently disclosed subject matter. The term "universal base" as used herein refers to nucleotide base analogs that form base pairs with each of the natural DNA/RNA bases with little discrimination between them. Non-limiting examples of universal bases include C-phenyl, C-naphthyl and other aromatic derivatives, inosine, azole carboxamides, and nitroazole derivatives such as 3-nitropyrrole, 4-nitroindole, 5-nitroindole, and 6-nitroindole as known in the art (see, for example, Loakes, 2001).

In some embodiments, the presently disclosed subject matter features conjugates and/or complexes of enzymatic DNA molecules. Such conjugates and/or complexes can be used to facilitate delivery of the DNA molecules into a biological system, such as a cell. The conjugates and complexes provided by the presently disclosed subject matter can impart therapeutic activity by transferring therapeutic compounds across cellular membranes, altering the pharmacokinetics of, and/or modulating the localization of nucleic acid molecules of the presently disclosed subject matter. The presently disclosed subject matter encompasses the design and synthesis of novel conjugates and complexes for the delivery of molecules, including, but not limited to, small molecules, lipids, phospholipids, nucleosides, nucleotides, nucleic acids, antibodies, toxins, negatively charged polymers, and other polymers, for example proteins, peptides, hormones, carbohydrates, polyethylene glycols, or polyamines, across cellular membranes. In general, the transporters described are designed to be used either individually or as part of a multi-component system, with or without degradable linkers. These compounds are expected to improve delivery and/or localization of nucleic acid molecules of the presently disclosed subject matter into a number of cell types originating from different tissues, in the presence or absence of serum (see U.S. Pat. No. 5,854,038). Conjugates of the molecules described herein can be attached to biologically active molecules via linkers that are biodegradable, such as biodegradable nucleic acid linker molecules.

The term "biodegradable linker" as used herein, refers to a nucleic acid or non-nucleic acid linker molecule that is designed as a biodegradable linker to connect one molecule to another molecule, for example, a biologically active molecule to a enzymatic DNA molecules of the presently disclosed subject matter. The biodegradable linker is designed such that its stability can be modulated for a particular purpose, such as delivery to a particular tissue or cell type. The stability of a nucleic acid-based biodegradable linker molecule can be modulated by using various chemistries, for example combinations of ribonucleotides, deoxyribonucleotides, and chemically modified nucleotides, such as 2'-O-methyl, 2'-fluoro, 2'-amino, 2'-O-amino, 2'-C-allyl, 2'-O-allyl, and other 2'-modified or base modified nucleotides. The biodegradable nucleic acid linker molecule can be a dimer, trimer, tetramer or longer nucleic acid molecule, for example, an oligonucleotide of about 2, 3, 4, 5, 6, 7, 8, 9, 10, 11, 12, 13, 14, 15, 16, 17, 18, 19, or 20 nucleotides in length, or can comprise a single nucleotide with a phosphorus-based linkage, for example, a phosphoramidate or phosphodiester linkage. The biodegradable nucleic acid linker molecule can also comprise nucleic acid backbone, nucleic acid sugar, or nucleic acid base modifications.

The term "biodegradable" as used herein, refers to degradation in a biological system, for example enzymatic degradation or chemical degradation.

The term "biologically active molecule" as used herein, refers to compounds or molecules that are capable of eliciting or modifying a biological response in a system. Non-limiting examples of biologically active molecules provided by the presently disclosed subject matter include therapeutically active molecules such as antibodies, hormones, antivirals, peptides, proteins, chemotherapeutics, small molecules, vitamins, co-factors, nucleosides, nucleotides, oligonucleotides, enzymatic nucleic acids, antisense nucleic acids, triplex forming oligonucleotides, 2,5-A chimeras, DNAzymes, siRNA, dsRNA, allozymes, aptamers, decoys, and analogs thereof. Biologically active molecules of the presently disclosed subject matter also include molecules capable of modulating the pharmacokinetics and/or pharmacodynamics of other biologically active molecules, for example, lipids and polymers such as polyamines, polyamides, polyethylene glycol, and other polyethers.

The term "phospholipid" as used herein, refers to a hydrophobic molecule comprising at least one phosphorus group. For example, a phospholipid can comprise a phosphorus-containing group and saturated or unsaturated alkyl group, optionally substituted with OH, COOH, oxo, amine, or substituted or unsubstituted aryl groups.

Nucleic acid molecules (e.g., enzymatic DNA molecules such as DNAzymes) delivered exogenously are intended to be stable within cells until the level of the target RNA has been reduced sufficiently. The nucleic acid molecules are resistant to nucleases in order to function as effective intracellular therapeutic agents. Improvements in the chemical synthesis of nucleic acid molecules described in the presently disclosed subject matter and in the art have expanded the ability to modify nucleic acid molecules by introducing nucleotide modifications to enhance their nuclease stability as described above.

Use of the enzymatic nucleic acid-based molecules of the presently disclosed subject matter will lead to better treatment of the disease progression by affording the possibility of combination therapies (e.g., multiple enzymatic DNA molecules targeted to different genes; nucleic acid molecules coupled with known small molecule modulators; or intermittent treatment with combinations of molecules, including different motifs and/or other chemical or biological molecules). The treatment of subjects with enzymatic DNA molecules can also include combinations of different types of nucleic acid molecules, such as ribozymes, allozymes, antisense, 2,5-A oligoadenylate, decoys, aptamers etc.

In another aspect, an enzymatic DNA molecule of the presently disclosed subject matter is modified to comprise one or more 5' and/or 3'-cap structures.

As used herein, the phrase "cap structure" is meant to refer to chemical modifications that have been incorporated at either terminus of the oligonucleotide (see e.g., U.S. Pat. No. 5,998,203, incorporated by reference herein). These terminal modifications protect the nucleic acid molecule from exonuclease degradation, and can help in delivery and/or localization within a cell. The cap modification can be present at the 5'-terminus (5'-cap) or at the 3'-terminal (3'-cap), or can be present on both termini. In non-limiting examples: the 5'-cap is selected from the group comprising inverted abasic residue (moiety); 4',5'-methylene nucleotide; 1-(beta-D-erythrofuranosyl) nucleotide, 4'-thio nucleotide; carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety.

In some embodiments, the 3'-cap is selected from a group comprising inverted deoxynucleotide, such as for example inverted deoxythymidine, 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate; 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (see generally Beaucage & Iyer, 1993; incorporated by reference herein).

As used herein, the term "non-nucleotide" refers to any group or compound which can be incorporated into a nucleic acid chain in the place of one or more nucleotide units, including either sugar and/or phosphate substitutions, and allows the remaining bases to exhibit their enzymatic activity. The group or compound is typically abasic, in that it does not typically contain a commonly recognized nucleotide base, such as adenine (A), guanine (G), cytosine (C), thymine (T), or uracil (U), and therefore lacks a base at the 1'-position.

As used herein, the term "alkyl" group refers to a saturated aliphatic hydrocarbon, including straight-chain, branched-chain, and cyclic alkyl groups. In some embodiments, the alkyl group has 1 to 12 carbons. In some embodiments, it is a lower alkyl of from 1 to 7 carbons, and in some embodiments it is a lower alkyl of from 1 to 4 carbons. The alkyl group can be substituted or unsubstituted. When substituted the substituted group(s) is in alternative embodiments, hydroxyl, cyano, alkoxy, $=O$, $=S$, $NO_2$ or $N(CH_3)_2$, amino, or SH.

The term "alkyl" also includes alkenyl groups that are unsaturated hydrocarbon groups containing at least one carbon-carbon double bond, including straight-chain, branched-chain, and cyclic groups. In some embodiments, the alkenyl group has 1 to 12 carbons. In some embodiments, it is a lower alkenyl of from 1 to 7 carbons, and in some embodiments it is a lower alkenyl of from 1 to 4 carbons. The alkenyl group can be substituted or unsubstituted. When substituted the substituted group(s) is in alternative embodiments, hydroxyl, cyano, alkoxy, $=O$, $=S$, $NO_2$, halogen, $N(CH_3)_2$, amino, or SH.

The term "alkyl" also includes alkynyl groups that have an unsaturated hydrocarbon group containing at least one carbon-carbon triple bond, including straight-chain, branched-chain, and cyclic groups. In some embodiments, the alkynyl group has 1 to 12 carbons. In some embodiments, it is a lower alkynyl of from 1 to 7 carbons, and in some embodiments it is a lower alkynyl of from 1 to 4 carbons. The alkynyl group can be substituted or unsubstituted. When substituted the substituted group(s) is in alternative embodiments, hydroxyl, cyano, alkoxy, $=O$, $=S$, $NO_2$ or $N(CH_3)_2$, amino or SH.

Such alkyl groups can also include aryl, alkylaryl, carbocyclic aryl, heterocyclic aryl, amide, and ester groups. An "aryl" group refers to an aromatic group that has at least one ring having a conjugated pi electron system and includes carbocyclic aryl, heterocyclic aryl, and biaryl groups, all of which can be optionally substituted. Exemplary substituent(s) of aryl groups are halogen, trihalomethyl, hydroxyl, SH, OH, cyano, alkoxy, alkyl, alkenyl, alkynyl, and amino groups. An "alkylaryl" group refers to an alkyl group (as described above) covalently joined to an aryl group (as described above). Carbocyclic aryl groups are groups wherein the ring atoms on the aromatic ring are all carbon atoms. The carbon atoms are optionally substituted. Heterocyclic aryl groups are groups having from 1 to 3 heteroatoms as ring atoms in the aromatic ring and the remainder of the ring atoms are carbon atoms. Suitable heteroatoms include oxygen, sulfur, and nitrogen, and include furanyl, thienyl, pyridyl, pyrrolyl, N-lower alkyl pyrrolo, pyrimidyl, pyrazinyl, imidazolyl and the like, all optionally substituted. An "amide" refers to an —C(O)—NH—R, where R is either alkyl, aryl, alkylaryl, or hydrogen. An "ester" refers to an C(O)—OR', where R is either alkyl, aryl, alkylaryl, or hydrogen.

The term "nucleotide" is used herein as recognized in the art to include natural bases (standard), and modified bases well known in the art. Such bases are generally located at the 1' position of a nucleotide sugar moiety. Nucleotides generally comprise a base, sugar, and a phosphate group. The nucleotides can be unmodified or modified at the sugar, phosphate, and/or base moiety, (also referred to interchangeably as nucleotide analogs, modified nucleotides, non-natural nucleotides, non-standard nucleotides, and other; see e.g., Usman et al., 1996; PCT International Publication Nos. WO 92/07065 and WO 93/15187, all incorporated by reference herein). There are several examples of modified nucleic acid bases known in the art as summarized by Limbach et al., 1994. Some of the non-limiting examples of base modifications that can be introduced into nucleic acid molecules include, inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine), 6-azapyrimidines and 6-alkylpyrimidines (e.g. 6-methyluridine), propyne, and others (Burgin et al., 1996; Uhlman & Peyman, 1990). By "modified bases" in this aspect is meant nucleotide bases other than adenine, guanine, cytosine, and uracil at 1' position or their equivalents.

In some embodiments, the presently disclosed subject matter features modified enzymatic DNA molecules with phosphate backbone modifications comprising one or more phosphorothioate, phosphorodithioate, methylphosphonate, phosphotriester, morpholino, amidate carbamate, carboxymethyl, acetamidate, polyamide, sulfonate, sulfonamide, sulfamate, formacetal, thioformacetal, and/or alkylsilyl, substitutions. For a review of oligonucleotide backbone modifications, see Hunziker & Leumann, 1995 and De Mesmaeker et al., 1994.

As used herein, the phrase "unmodified nucleoside" refers to one of the bases adenine, cytosine, guanine, thymine, or uracil joined to the 1' carbon of β-D-ribo-furanose.

By "modified nucleoside" is meant any nucleotide base that contains a modification in the chemical structure of an unmodified nucleotide base, sugar and/or phosphate.

In connection with 2'-modified nucleotides as described for the presently disclosed subject matter, by "amino" is meant 2'—NH$_2$ or 2'-O—NH$_2$, which can be modified or unmodified. Such modified groups are described, for example, in U.S. Pat. Nos. 5,672,695 and 6,248,878, which are both incorporated by reference in their entireties.

Various modifications to enzymatic DNA molecule nucleic acid structure can be made to enhance the utility of these molecules. Such modifications will enhance shelf-life, half-life in vitro, stability, and/or ease of introduction of such oligonucleotides to the target site (for example, to enhance penetration of cellular membranes, and confer the ability to recognize and bind to targeted cells).

IV. Applications

The presently disclosed subject matter provides a method of modulating cellular expression of at least one matrix metalloproteinase protein, the method comprising introducing into a cell at least one DNA oligonucleotide having binding specificity for a target region of a mRNA encoding a matrix metalloproteinase protein. In some embodiments, modulating cellular expression of the matrix metalloproteinase protein comprises inhibiting expression of the matrix metalloproteinase protein.

The presently disclosed subject matter further provides a method of inhibiting metastasis of a cancer cell, the method comprising introducing into a cancer cell at least one DNA oligonucleotide having binding specificity for a target region of a mRNA encoding a protein which contributes to metastasis. In some embodiments, inhibiting metastasis of the cancer cell comprises inhibiting expression of the protein that contributes to metastasis.

In some embodiments, the protein is an enzyme that degrades extracellular matrix components and in some embodiments, the enzyme is a matrix metalloproteinase protein. In some particular embodiments, the matrix metalloproteinase protein is MMP-2, MMP-9, or both MMP-2 and MMP-9.

In some embodiments, the cancer cell is a cell from a cancerous tissue selected from the group consisting of glioma, melanoma, fibrosarcoma, and adenosarcoma. In other embodiments, the cancer cell is from a cancerous tissue selected from the group consisting, but not limited to, human sarcomas and carcinomas, including but not limited to myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, astrocytoma, medulloblastoma, craniopharyngioma, ependymoma, pinealoma, hemangioblastoma, acoustic neuroma, oligodendroglioma, meningioma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrböom's macroglobulinemia, and heavy chain disease.

The presently disclosed subject matter still further provides a method of modulating tumor growth in a subject, the method comprising administering to a subject a composition comprising at least one DNA oligonucleotide having binding specificity for a target region of a mRNA encoding a matrix metalloproteinase protein. In some embodiments, modulating tumor growth comprises inhibiting tumor growth.

In some embodiments of the methods provided above, the DNA oligonucleotide can be an enzymatic DNA oligonucleotide, and in some embodiments, the DNA oligonucleotide is a DNAzyme. In some embodiments, the DNAzyme comprises a catalytic domain flanked on each side by substrate binding domains each having binding specificity for a distinct nucleotide sequence of the target region. In some particular embodiments, the DNA oligonucleotide has a nucleotide sequence comprising the sequence of SEQ ID NOs:1-12, 22, and 29.

In some embodiments of the methods provided above, the methods comprise modulating cellular expression of more than one MMP by introducing into a cell more than one DNA oligonucleotide, each having binding specificity for a target region of a distinct mRNA encoding a matrix metalloproteinase protein. In some embodiments, DNA oligonucleotides are introduced into a cell, wherein one DNA oligonucleotide has binding specificity for a target region of a mRNA encoding MMP-2 and another DNA oligonucleotide has binding specificity for a target region of a mRNA encoding MMP-9.

IV.A. Subjects

The subjects treated in the presently disclosed subject matter in its many embodiments are desirably a human subjects, although it is to be understood that the principles of the presently disclosed subject matter indicate that the presently disclosed subject matter is effective with respect to invertebrate and to all vertebrate species, including mammals, which are intended to be included in the term "subject". Moreover, a mammal is understood to include any mammalian species in which treatment or prevention of cancer is desirable, particularly agricultural and domestic mammalian species.

The methods of the presently disclosed subject matter are particularly useful in the treatment of warm-blooded vertebrates. Thus, the presently disclosed subject matter concerns mammals and birds.

More particularly provided is the treatment of mammals such as humans, as well as those mammals of importance due to being endangered (such as Siberian tigers), of economic importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also provided is the treatment of birds, including the treatment of those kinds of birds that are endangered, kept in zoos, as well as fowl, and more particularly domesticated fowl, i.e., poultry, such as turkeys, chickens, ducks, geese, guinea fowl, and the like, as they are also of economic importance to humans. Thus, contemplated is the treatment of livestock, including, but not limited to, domesticated swine (pigs and hogs), ruminants, horses, poultry, and the like.

IV.B. Formulation

The presently disclosed subject matter comprises in some embodiments a composition that includes at least one DNA oligonucleotide as disclosed herein having binding specificity for a target region of a target nucleic acid, such as but not limited to a mRNA encoding a MMP peptide. In some embodiments, the DNA oligonucleotide can be an enzymatic DNA oligonucleotide, and in some embodiments, the DNA oligonucleotide is a DNAzyme. In some embodiments, the DNAzyme comprises a catalytic domain flanked on each side by substrate binding domains each having binding specificity for a distinct nucleotide sequence of the target region. In some particular embodiments, DNA oligonucleotide has a nucleotide sequence comprising the sequence of SEQ ID NOs:1-12, 22, and 29.

In some embodiments, the composition comprises more than one DNA oligonucleotide, each having binding specificity for a target region of a distinct mRNA encoding a matrix metalloproteinase protein. In some embodiments, one DNA oligonucleotide within the composition has binding specificity for a target region of a mRNA encoding MMP-2 and another DNA oligonucleotide within the composition has binding specificity for a target region of a mRNA encoding MMP-9.

In some embodiments, the composition also comprises a carrier, which can be a pharmaceutically acceptable carrier thereby providing a composition suitable for administration to a subject. Any suitable pharmaceutical formulation can be used to prepare the composition for administration to a subject.

For example, suitable formulations can include aqueous and non-aqueous sterile injection solutions which can contain anti-oxidants, buffers, bacteriostats, bactericidal antibiotics and solutes which render the formulation isotonic with the bodily fluids of the intended recipient; and aqueous and non-aqueous sterile suspensions which can include suspending agents and thickening agents. The formulations can be presented in unit-dose or multi-dose containers, for example sealed ampoules and vials, and can be stored in a frozen or freeze-dried (lyophilized) condition requiring only the addition of sterile liquid carrier, for example water for injections, immediately prior to use. Some exemplary ingredients are SDS, in one example in the range of 0.1 to 10 mg/ml, in another example about 2.0 mg/ml; and/or mannitol or another sugar, for example in the range of 10 to 100 mg/ml, in another example about 30 mg/ml; and/or phosphate-buffered saline (PBS).

It should be understood that in addition to the ingredients particularly mentioned above the formulations of this presently disclosed subject matter can include other agents conventional in the art having regard to the type of formulation in question. For example, sterile pyrogen-free aqueous and non-aqueous solutions can be used.

The therapeutic regimens and compositions of the presently disclosed subject matter can be used with additional adjuvants or biological response modifiers including, but not limited to, the cytokines IFN-α, IFN-γ, IL2, IL4, IL6, TNF, or other cytokine affecting immune cells. In accordance with this aspect of the presently disclosed subject matter, the disclosed nucleic acid molecules can be administered in combination therapy with one or more of these cytokines.

IV.C. Administration

Administration of the compositions of the presently disclosed subject matter can be by any method known to one of ordinary skill in the art, including, but not limited to intravenous administration, intrasynovial administration, transdermal administration, intramuscular administration, subcutaneous administration, topical administration, rectal administration, intravaginal administration, intratumoral administration, oral administration, buccal administration, nasal administration, parenteral administration, inhalation, and insufflation. In some embodiments, suitable methods for administration of a DNA molecule of the presently disclosed subject matter include but are not limited to direct injection, pump infusion (e.g. by osmotic pump), intravenous, or intratumoral injection. Alternatively, a nucleic acid molecule can be deposited at a site in need of treatment in any other manner, for example by spraying a composition comprising a nucleic acid molecule within the pulmonary pathways. The particular mode of administering a composition of the presently disclosed subject matter depends on various factors, including the distribution and abundance of cells to be treated, the vector employed, additional tissue- or cell-targeting features of the vector, and mechanisms for metabolism or removal of the vector from its site of administration. For example, relatively superficial tumors can be injected intratumorally. By contrast, internal tumors can be treated by intravenous injection.

In some embodiments, the method of administration encompasses features for steady-state regionalized delivery or accumulation at the site in need of treatment. In one example, a DNA molecule disclosed herein is delivered to a tumor using a mini-osmotic pump (e.g. an ALZET® mini-osmotic pump (DURECT Corporation, Cupertino, Calif., U.S.A.)). These pumps can be filled with oligonucleotides in solution, and will deliver the oligonucleotides by an osmotic displacement mechanism. Mini-osmotic pumps have a distinct advantage over direct injection for delivery of therapeutic agents such as DNAzymes because they maintain a well-defined and consistent pattern of delivery and tissue exposure over a significant period of time. Molecular weight, physical conformation, and chemical properties do not affect the delivery rate of a given compound. This mechanism of delivery is discussed in detail in Example 7.

IV.D. Dose

An effective dose of a composition of the presently disclosed subject matter is administered to a subject in need thereof. A "therapeutically effective amount" is an amount of the composition sufficient to produce a measurable response (e.g., modulation of a cellular expression of at least one matrix metalloproteinase protein, an inhibition in tumor growth or metastasis in a subject being treated). In some embodiments, an activity that inhibits tumor growth is measured. Actual dosage levels of active ingredients in the compositions of the presently disclosed subject matter can be varied so as to administer an amount of the active compound(s) that is effective to achieve the desired therapeutic response for a particular subject. The selected dosage level will depend upon the activity of the therapeutic composition, the route of administration, combination with other drugs or treatments, the severity of the condition being treated, and the condition and prior medical history of the subject being treated. However, it is within the skill of the art to start doses of the compound at levels lower than required to achieve the desired therapeutic effect and to gradually increase the dosage until the desired effect is achieved. The potency of a composition can vary, and therefore a "therapeutically effective" amount can vary. However, using the assay methods described herein below, one skilled in the art can readily assess the potency and efficacy of a candidate modulator of this presently disclosed subject matter and adjust the therapeutic regimen accordingly.

After review of the disclosure of the presently disclosed subject matter presented herein, one of ordinary skill in the art can tailor the dosages to an individual patient, taking into account the particular formulation, method of administration to be used with the composition, and tumor size. Further calculations of dose can consider patient height and weight, severity and stage of symptoms, and the presence of additional deleterious physical conditions. Such adjustments or variations, as well as evaluation of when and how to make such adjustments or variations, are well known to those of ordinary skill in the art of medicine.

EXAMPLES

The following Examples have been included to illustrate modes of the presently disclosed subject matter. In light of the present disclosure and the general level of skill in the art, those of skill will appreciate that the following Examples are intended to be exemplary only and that numerous changes, modifications, and alterations can be employed without departing from the scope of the presently disclosed subject matter.

Material and Methods Utilized in Examples

Cells and Cell Culture

The COS-7 cell line (American Type Culture Collection (ATCC), Manassas, Va., U.S.A.) was maintained as a monolayer culture at 37° C., 10% $CO_2$ in Dulbecco's modified Eagles medium (DMEM) supplemented with 10% heat-inactivated fetal bovine serum, 100 i.u./ml penicillin, and 100 μg/ml streptomycin. Human MMP-9 was cloned into the pcDNA3 human expression vector (pcDNA3-MMP-9), and pcDNA3-MMP-9 was transfected into the COS-7 cell line using electroporation. G418 (400 μg/ml) selection was used to establish a cell line that stably expressed the pcDNA3-MMP-9 construct (COS-7-NG). The C6 glioma cell line (ATCC) was maintained as a monolayer culture at 37° C., 5% $CO_2$ in Hams/F12 supplemented with 15% heat-inactivated horse serum, 2.5% heat-inactivated fetal bovine serum, 100 i.u./ml penicillin, and 100 μg/ml streptomycin. The rat C6 and human U87 and SNB19 glioma cell lines were stably transduced with the pFB retrovirus (pFB-GFP) (Stratagene, La Jolla, Calif., U.S.A.) expressing green fluorescent protein (GFP) to enhance visual analysis. Cells stably transduced with GFP were sorted by a fluorescence activated cell sorter (FACS) to generate a cell population homogeneously expressing high levels of GFP (C6-GFP, U87-GFP, SNB19-GFP). For generating C6 intracranial glioma, C6-GFP cells in exponential growth were harvested by EDTA/Trypsin for 5 min at 37° C. Trypsinization was stopped with the complete media described above, and the cells were centrifuged for 5 min at 1,000 RPM. The pellets were resuspended in sterile phosphate buffered saline (PBS) and counted using Trypan blue staining methods. The pellets were then resuspended in PBS at a concentration of $1 \times 10^4$/μl and placed on ice.

Design of Catalytic DNAzymes

All DNA oligonucleotides used in these Examples were synthesised by Integrated DNA Technology (Coralville, Iowa, U.S.A.). Eleven Anti-MMP-9 and four anti MMP-2 DNAzymes with nine nucleotides on both substrate binding arms (domains) flanking the nucleotide 10-23 catalytic core domain and targeting various sites of mRNA of either human MMP-9 or MMP-2 were designed and synthesized. A random DNA oligonucleotide where both arms are composed of random sequence and the 10-23 catalytic core domain is preserved was designed as a negative control (CTAGTCAGCG-GCTAGCTACAACGATAAGCTGCT; SEQ ID NO:20). Modified versions of the DNAzyme AS6 (SEQ ID NO:6) referred to herein as Mod-AS6 and Mod-S6 with an inverted T modification at the 3' end were also generated and tested. An anti-rat-MMP-9 DNAzyme molecule (ATGGTGCCAG-GCTAGCTACAACGATTGAGGTCG; SEQ ID NO:22) was designed by modelling the human AS6 DNAzyme and used for all animal studies. A complete list of specific oligonucleotides disclosed in the present application is provided in Table 1 below.

TABLE 1

| Name | SEQ ID NO: | Sequence |
|---|---|---|
| HUMAN MMP-9 DNAzyme SEQUENCES | | |
| AS1: | 1 | 5'-AACAAACTGGGCTAGCTACAACGAATCCTTGGT |
| AS2: | 2 | 5'-TTCTTGTCGGGCTAGCTACAACGATGTCAAAGT |
| AS3: | 3 | 5'-AGCCCAGCAGGCTAGCTACAACGACAGGAGCAC |
| AS4: | 4 | 5'-AAGGGTGGAGGCTAGCTACAACGATGGCGCTGT |
| AS5: | 5 | 5'-ATAGCGGTAGGCTAGCTACAACGAAGGTATTCC |
| AS6: | 6 | 5'-GTGGTGCCAGGCTAGCTACAACGATTGAGGTCG |
| AS7: | 7 | 5'-GTGGCCGAAGGCTAGCTACAACGATCATGCGCC |
| AS8: | 8 | 5'-CCCCAGAGAGGCTAGCTACAACGATTCGACTCT |
| AS9: | 9 | 5'-GCAGCCCAGGGCTAGCTACAACGAACCAGGAGC |
| AS10: | 10 | 5'-AGATTTCGAGGCTAGCTACAACGATCTCCACGC |
| AS11: | 11 | 5'-AGAGGCTCAGGCTAGCTACAACGAGGTGAGGGC |
| HUMAN MMP-2 DNAzyme SEQUENCE | | |
| 72K01 | 12 | 5'-CCTTCAGCAGGCTAGCTACAACGAAAACAGGTT |

| SEQ ID NO: | Sequence |
|---|---|
| CONTROL DNAZYMES | |
| 13 | 5'-ACCAAGGATGGCTAGCTACAACGACAGTTTGTT |
| 14 | 5'-ACTTTGACAGGCTAGCTACAACGACGACAAGAA |
| 15 | 5'-GTGCTCCTGGGCTAGCTACAACGATGCTGGGCT |
| 16 | 5'-ACAGCGCCAGGCTAGCTACAACGATCCACCCTT |
| 17 | 5'-GGAATACCTGGCTAGCTACAACGATACCGCTAT |
| 18 | 5'-CGACCTCAAGGCTAGCTACAACGATGGCACCAC |
| 19 | 5'-GCCCTCACCGGCTAGCTACAACGATGAGCCTCT |
| SCRAMBLED ARM CONTROL | |
| 20 | 5'-CTAGTCAGCGGCTAGCTACAACGATAAGCTGCT |
| SCRAMBLED CATALYTIC DOMAIN CONTROL | |
| 21 | 5'-AGCCCAGCAAGCAATGCACGATCGCAGGAGCAC |
| RAT MMP-9 DNAzyme | |
| 22 | 5'-ATGGTGCCAGGCTAGCTACAACGATTGAGGTCG |
| RAT MMP-9 DNAzyme CONTROL | |
| 23 | 5'-CGACCTCAAGGCTAGCTACAACGATGGCACCAT |

| SEQ ID | Name | Sequence |
|---|---|---|
| PRIMERS | | |
| 24 | MMP-9 fwd | 5'-GCAGGAATGCGGCTCTGG |
| 25 | MMP-9 rev | 5'-CCCGTCGAAGGGATACC |

TABLE 1-continued

| 26 | Actin fwd | 5'-CAAGAGATGGCCACGGCGGCT |
| 27 | Actin rev | 5'-TCCTTCTGCATCCTGTCAGCA |

| SEQ ID NO: | Sequence |
|---|---|
| | RAT MMP-2 DNAzyme CONTROL |
| 28 | 5'-CTAGTCAGCGGCTAGCTACAACGATAAGCTGCT |
| | RAT MMP-2 DNAzyme |
| 29 | 5'-CTTTCACGAGGCTAGCTACAACGAAAAGACGTT |

*Bolded nucleotides represent substrate binding domains, whereas unbolded nucleotides represent catalytic domains.

In Vitro Transcription and Cleavage Analysis of MMPs2 and -9 Substrate RNA

The pBLUESCRIPT® plasmid (Stratagene, La Jolla, Calif., U.S.A.) with either the human MMP-2 or -9 cDNA insert was digested with a restriction enzyme to linearize the template for in vitro transcription. The RNA substrate (764 nucleotides (nt)) that corresponds to the region of either MMP-2 or MMP-9 used to design the 11 DNAzymes tested in these Examples was transcribed using T3 RNA polymerase. 12.5 µM of each DNAzyme was incubated with 0.48 µM of RNA substrate in 50 mM Tris-HCl, pH 7.5, and 10 mM $MgCl_2$ at 37° C. for various times. After incubation, the reaction mixture was mixed with 90% formamide in TBE, and loaded onto a 4% polyacrylamide-urea gel. The RNA bands were visualized after Ethidium Bromide staining and the scanning density of RNA bands separated on a gel was determined using an ALPHAIMAGER® 2000 documentation and analysis system (Alpha Innotech Corp., San Leandro, Calif., U.S.A.).

Labeling of DNAzymes

DNAzymes and control oligonucleotides were fluorescently labeled at the 5' end with OREGON GREEN™ 488 maleimide (Molecular Probes, Eugene, Oreg., U.S.A.). The labeling step involves the transfer of a phosphorothioate group the 5' end in a reaction catalyzed by T4 polynucleotide kinase using adenosine-5'-O-3-thiotriphosphate as a substrate. The oligonucleotides are then reacted with OREGON GREEN™ 488 maleimide to the sulphur atom of the phosphorothioate. The labeled oligonucleotides were purified with the MERMAID® Kit (BIO 101, La Jolla, Calif., U.S.A.).

Transfection of Cells with DNAzymes, Sorting the Transfected Cells, and Fluorescent Microscopy $2.2 \times 10^6$ of either COS-7-NG, C-6, U87, or SNB19 cells were plated on a 10 cm dish in 10 ml of fresh supplemented media containing the day before transfection. Cells were rinsed with serum free medium and then incubated in 10 ml of serum free medium. 24 µg of fluorescently-labeled oligonucleotides (for example AS6 or S6) were resuspended with the DOTAP transfection reagent (Roche, Mannheim, Germany) and added to the tissue culture plates according to the manufacturer's protocol and incubated at 37° C. for 24 h. Cells were collected at different time points and analyzed or sorted to isolate transfected cells with fluorescently labeled oligonucleotides using an EPICS ELITE ESP™ flow cytometer (Beckman Coulter, Fullerton, Calif., U.S.A.) by the Flow Cytometry Laboratory in the Molecular Resource Center, University of Tennessee Health Science Center. COS-7-NG cells transfected with fluorescent oligonucleotides were also plated on culture dishes mounted on a glass slide. After 24 hours incubation, the cells were fixed with 4% paraformaldehyde, coverslipped, and observed by fluorescent microscopy.

Reverse Transcription-Polymerase Chain Reaction (RT-PCR)

Total RNA was isolated using the guanidine isothiocyanate method previously described by Day et al. (Day et al., 1992) or with TRIZOL reagent (Invitrogen, Carlsbad, Calif., U.S.A.). 2 µg of the RNA was reverse transcribed with a random hexamer (Promega, Madison, Wis., U.S.A.) by MMLV-RT (Invitrogen, Carlsbad, Calif., U.S.A.). 2 µl of the first-strand cDNA was used for PCR amplification. The human MMP-9 cDNA in pcDNA3 was amplified with primers designed to amplify the pcDNA-MMP-9: 5'-GCAG-GAATGCGGCTCTGG-3' (forward; SEQ ID NO:24) and 5'-CCCGTCGAAGGGATACC-3' (reverse; SEQ ID NO:25). As an internal control, β-actin mRNA was amplified in parallel with 5'-CAAGAGATGGCCACGGCGGCT-3' (forward; SEQ ID NO:26) and 5'-TCCTTCTGCATCCTGT-CAGCA-3' (reverse; SEQ ID NO:27) primers. The PCR products were loaded on a 2% agarose gel and visualized by Ethidium Bromide staining.

Gelatin Zymography

Gelatin at 1.0 mg/ml was dissolved in 10% SDS-polyacrylamide and enzyme samples were loaded onto the gel without being boiled. After electrophoresis, the gels were washed twice with 50 mM Tris-HCl, 5 mM $CaCl_2$, 1 mM $ZnCl_2$, 1% Triton X-100, and 0.02% NaN3 at 25° C. and incubated in the same buffer for 16 h at 37° C. The gels were stained with Coomassie Blue and destained in methanol/acetic acid mixture prior to visualization.

Cell Analysis Using a Basement Membrane Model

The CELL INVASION ASSAY KIT™ (CHEMICON, Temecula, Calif., U.S.A.) was used as a model for the evaluation of the invasion of cells through a basement membrane model consisting of a thin layer of ECMatrix™ poured over a polycarbonate membrane with an 8 µm pore size. At 18 hours post transfection, fluorescently labelled AS6, S6, scrambled oligonucleotide, or 72K01 cells were FACS sorted and added to the membrane insert. After 24 hours incubation, the number of cells that migrated though the ECM layer and attached to the bottom of the polycarbonate membrane was quantitated by staining and destaining cells followed by calorimetric reading of optical density of the dye/solute mixture at 560 nm using a biochromatic plate reader according to the manufacturer's protocol. The assays were repeated four times, and the differences of the values between groups were evaluated by a paired t-test ($P<0.05$ was considered significant).

Collection of Tumor Samples for Microarray Analysis, Gene Expression Studies, and Statistical Analysis All tumors studied were from patients presenting for the first time with a diagnosis of high-grade glioma, and the diagnosis of GBM was based on pathological specimens taken from patients at the time of surgery in parallel with specimens used for microarray. Gene expression studies of these samples were compared to RNA from normal brain specimens commercially available from Stratagene (La Jolla, Calif., U.S.A.) and Clonetech (Palo Alto, Calif., U.S.A.). All protocols and consent forms were approved by the Methodist University Hospital Institutional Review Board, Memphis, Tenn., U.S.A., and informed consent was obtained from patients prior to surgery. Samples were stored in RNALATER® (Ambion, Austin, Tex., U.S.A.), transported to the laboratory for processing and storage, and total RNA was extracted from each sample using the RNA STAT-60™ reagent (Tel-Test, Friendswood, Tex., U.S.A.). RNA integrity was assayed prior to microarray analysis using an Agilent 2100 bioanalyzer (Agilent, Palo Alto, Calif., U.S.A.). cDNA was synthesized using a T-7 linked oligo-dT primer, and cRNA was then synthesized with biotinylated UTP and CTP.

The labeled RNA was then fragmented and hybridized to HG-U133 A & B oligonucleotide arrays (Affymetrix Incorporated, Santa Clara, Calif., U.S.A.) according to Affymetrix protocols. Arrays were scanned using a laser confocal scanner (Agilent) to measure probe hybridization, and gene expression was then estimated using robust multichip analysis (Irizary et al., 2003) as implemented in the statistical language R (Ihaka and Gentleman, 1996). Differences in expression between glioblastomas and normal brain were then assessed with a t-test for each gene.

Animal Experiments

Male Sprague-Dawley rats (Harlan, Inc, Indianapolis, Ind., U.S.A.) 250-300 g in weight were used for all studies. Animals were anesthetized with intraperitoneal injection of ketamine/xylazine solution at a dosage of 8.7/1.3 mg/100 g body weight. Animal preparation and surgery were performed under sterile conditions. After mounting the animal on a stereotaxic frame (Kopf Instruments, Tujunga, Calif., U.S.A.), a small burr hole was made with a handheld drill 3 mm lateral from midline along the bregma suture over the right hemisphere. A 30 G needle was inserted to a depth of 5 mm from the cortical surface. To follow the fate of fluorescently labeled oligos in vivo, 10 μl of fluorescently labeled oligos resuspended in PBS were injected into the brain over a period of 30 seconds using a 25 iii Hamilton syringe (Hamilton, Reno, Nev., U.S.A.). To inoculate glioma into the brain, PBS alone (sham-inoculated) or C6-GFP cells resuspended in PBS at a concentration of $1.0 \times 10^7$/ml were injected into the brain over a period of 30 seconds using a 25 μl Hamilton syringe (Hamilton). To test the effect of anti-rat-MMP-2 or -9 DNAzyme on developing intracranial glioma, anti-rat MMP-2 or -9 DNAzyme oligos (SEQ ID NOs: 29 and 22, respectively) or control sense oligos (SEQ ID NOs: 20, 23, or 28) resuspended in a volume of 10 μl of PBS were injected into the brain over a period of 30 seconds using a 25 μl Hamilton syringe (Hamilton). Once the needle was removed, a plug of bone wax was used to seal the burr hole, the area was thoroughly irrigated with sterile saline, and the wound was closed with sutures. Control oligonucleotides (SEQ ID NOs: 20, 23, or 28) or therapeutic MMP-2 or -9 DNAzyme oligos (SEQ ID NOs:29 or 22, respectively) were given on days 0, 3, 6, 9, and 12 post-inoculation of glioma cells. Animals were observed daily for signs of infection, alertness, feeding habits, and neurological deficits from tumor growth. Animals were sacrificed at day 14 post-inoculation by transcardiac perfusion with 4% paraformaldehyde under deep anesthesia. All surgical specimens were given additional fixation with 4% paraformaldehyde at 4° C. for 2 hours and cryoprotected in 30% sucrose prior to sectioning.

Hematoxylin-Eosin Staining

Rat brains were cut on a cryostat at 20 μm and collected on clean slides. The sections were stored at 4° C. before processing. Hematoxylin-eosin (H&E) staining was performed using the following procedures. The sections were immersed in 95% ethanol and rehydrated before being stained with 2% hematoxylin (245-655, Fisher Diagnostics, Middletown, Va., U.S.A.) for 1 min. After three rinses in water, the sections were treated with Scott's tap water substitute blueing solution (CS410-4, Fisher Scientific, Pittsburgh, Pa., U.S.A.). After a brief rinse in water, the sections were dehydrated in 95% ethanol for 1 min and stained with eosin (LC14030-2, LabChem, Inc., Pittsburgh, Pa., U.S.A.) for 3 min. The sections were subsequently coverslipped after dehydration in graded ethanol and xylene.

Immunohistochemistry

The primary anti-RAT MMP-9 antibody was obtained from Santa Cruz (sc-10737; Santa Cruz, Calif., U.S.A.). The immunohistochemistry was performed using the following procedures. The frozen brain sections were (1) briefly rinsed with phosphate buffered saline (PBS); (2) quenched with 3% hydrogen peroxide and 10% methanol for 20 min with 3 subsequent rinses with PBS; (3) incubated in 2% non-fat milk and 0.3% Triton-X in PBS for 1 hr; (4) incubated with primary antibody at a dilution of 1:250 with 3% donkey serum and 0.1% Triton-X overnight at room temperature; (5) washed with PBS for 3 times; (6) incubated in appropriate Cy™3 or 5-conjugated AffiniPure donkey anti-mouse, rabbit, or goat IgG (1:250; Jackson ImmunoResearch Laboratories, Inc., West Grove, Pa., U.S.A.) with 2% donkey serum and 0.1% Triton-X for 4 hr in dark at room temperature; (7) washed with PBS for 3 times; and (8) dehydrated through graded ethanol, cleared with xylene, and coverslipped with DPX mounting medium (44581; Fluka Biochemika, Switzerland). The immunoreactivity was visualized with a Bio-Rad confocal microscope and images collected on a computer for later analysis.

Example 1

Selection of DNAZyme

Eleven DNAzymes were designed and constructed according to their target sites in the mRNA of human MMP-9. Each DNAzyme bears the 10-23 motif as a catalytic core (catalytic domain) and 9 nucleotides in each arm (substrate binding domain) whose sequence is complimentary to its respective target sequence region. FIGS. 1A and 1B shows the targets sites of five selected DNAzymes (AS3 (SEQ ID NO:3), AS4 (SEQ ID NO:4), AS5 (SEQ ID NO:5), AS6 (SEQ ID NO:6), and AS8 (SEQ ID NO:8)) and FIG. 2 demonstrates the results of an in-vitro RNA substrate cleavage assay using those five DNAzymes to select the most effective anti-MMP-9 DNAzyme. As shown in FIG. 2, the AS3 DNAzyme did not generate any visible products, and the AS5 and AS8 cleaved less than 25% of RNA substrate in 2 h as demonstrated by the scanning density of RNA bands separated on a 2% gel. However, the AS4 and AS6 DNAzymes cleaved over 85% of the RNA substrate in 2 hours (FIG. 2). To determine whether AS4 or AS6 was superior, these DNAzymes were transiently transfected into Cos7 cells, and their effect on MMP-9 expression was measured by RT-PCR analysis. In these experiments, it was found that the AS6 to be consistently superior to the AS4 DNAzyme, and thus the AS6 DNAzyme was used for all Examples described below.

Example 2

Inhibition of COS-7-NG Expression of Human MMP-9 mRNA and Protein by the AS6 DNAzyme To enhance further analysis of AS6 enzymatic activity (SEQ ID NO:6), the AS6 DNAzyme was fluorescently labelled and transiently transfected into COS-7-NG cells using DOTAP. At 24 hours post-transfection, the cells were collected and analyzed for fluorescently labelled cells using flow cytometry and found to be roughly 70% positive for fluorescence on average. To increase the percentage of COS-7-NG cells exposed to the DNAzymes in further studies, cells successfully transfected with the AS6 DNAzyme were FACS-sorted using fluorescence as a marker. Sorted cells were analyzed using fluorescent microscopy, and the oligonucleotides were found to be distributed evenly throughout the cytoplasm up to 48 hours post-transfection.

Figure 4:
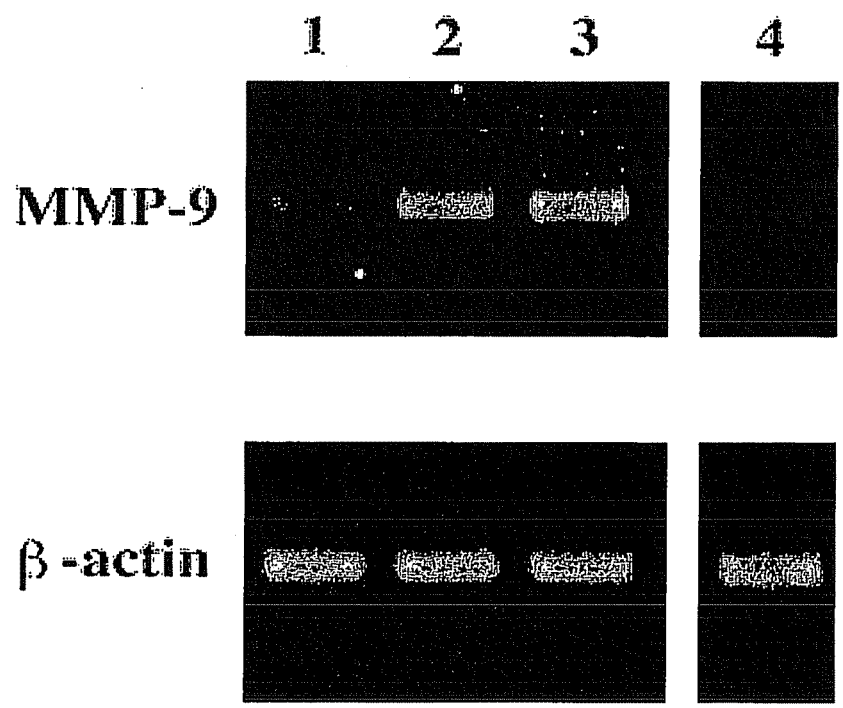
FIG. 4 is a photograph of an agarose gel showing the effect of a DNAzyme on MMP-9 mRNA expression. After transfection of the COS-7-NG cells with the AS6 DNAzyme or S6 followed by 24 hours incubation, total RNA was isolated from fluorescent positive cells sorted by FACS. RT-PCR was done to amplify human MMP-9 mRNA and β-actin mRNA with 23 cycles. The PCR product from COS-7-NG cells treated with AS6 (lane 1), S6 (lane 2), and DOTAP alone (lane 3), and the PCR product from COS-7-NG cells (lane 4) were subjected to 2% agarose gel and visualized by Ethidium Bromide staining.
Figure 5:
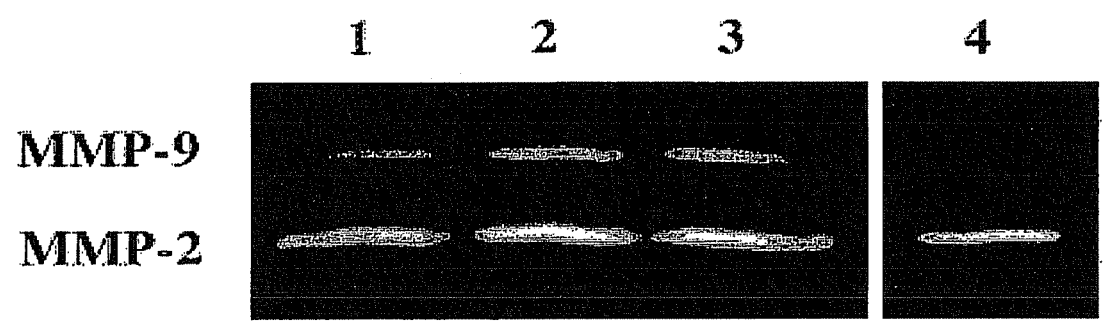
FIG. 5 is a photograph of a gelatin zymogram gel showing the effect of a DNAzyme on MMP-9 production. After incubation of COS-7-NG cells with AS6 DNAzyme or S6 for 18 hours, fluorescent positive cells sorted by FACS were re-plated at 1×10$^5$ cells in 0.1 ml of serum free medium in a 96 well microplate. Culture media from cells treated with AS6 (lane 1), S6 (lane 2), and DOTAP alone (lane 3), and culture medium from COS-7-NG cells were separated on a 10% polyacrylamide gel containing 1 mg/ml gelatin.

To study the effect of AS6 DNAzyme on MMP-9 RNA and protein expression, fluorescently labeled AS6 or S6 was transfected into COS-7-NG cells and subsequently FACS-sorted as described above. Total RNA was isolated from sorted cells, and RT-PCR was used to measure the effect of the AS6 DNAzyme on expression of human MMP-9 in those cells. As shown in FIG. 4, MMP-9 mRNA levels were significantly reduced in the AS6 treated-cells (lane 1) compared to the S6 treated cells (lane 2) and cells treated with DOTAP alone (lane 3). To verify the results of mRNA expression studies, a similar set of experiments were done to measure the effects of DNAzyme on MMP-9 production. COS-7-NG cells transfected with fluorescently labeled S6 or AS6 and FACS-sorted were plated at $1\times10^5$ cells in 0.1 ml of serum free medium on a 96 well microplate. Culture media was taken 3 hours after seeding cells, and the presence of MMP-9 was measured using gelatin zymography. As shown in FIG. 5, MMP-9 was greatly reduced in the AS6 group (lane 1) when compared to those with S6 (lane 2) or DOTAP alone (lane 3).

Example 3

Inhibition of COS-7-NG Cell Invasion of Cells Treated with the AS6 DNAzyme

Figure 6:
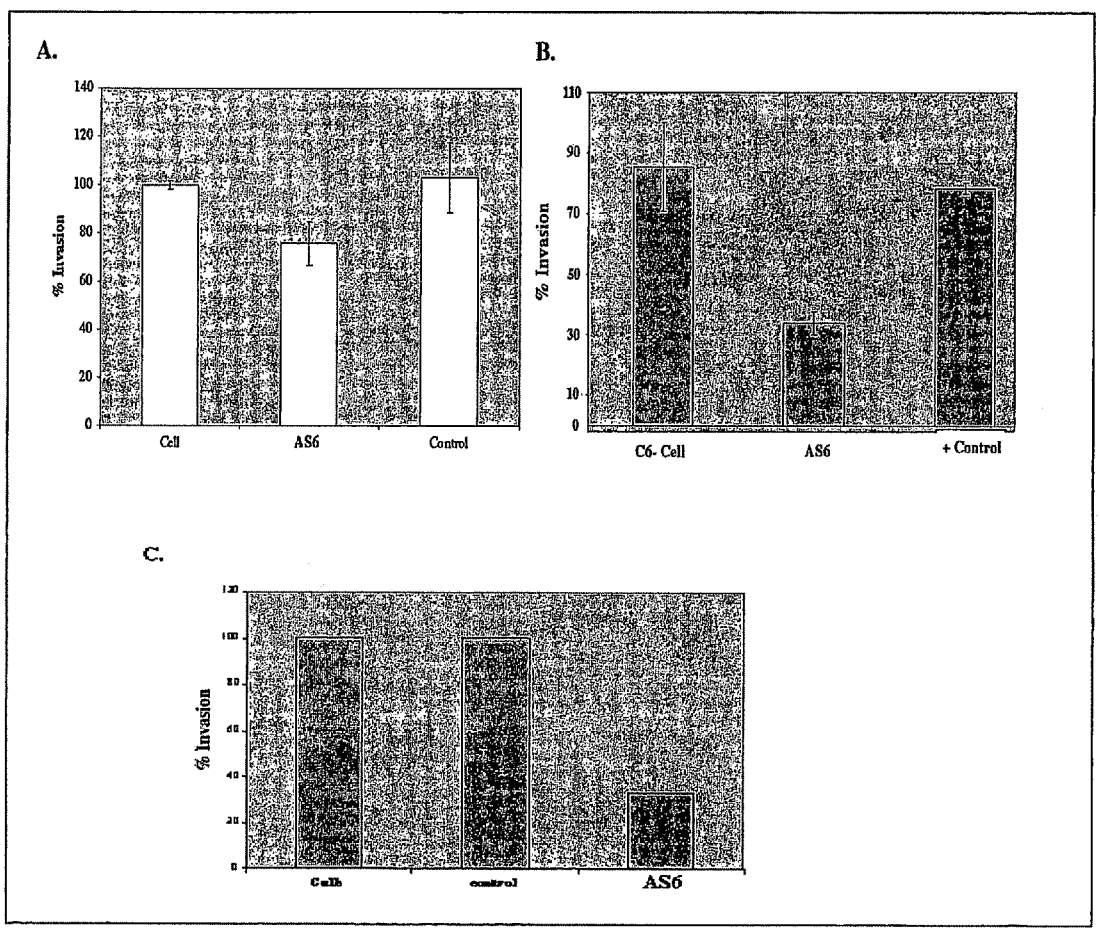
FIG. 6 is a graph depicting the results of a cell invasion assay. 18 h after transfection with labeled AS6 or S6 oligos, fluorescent positive cells.

After demonstrating a reduction in MMP-9 expression at the mRNA and protein level, studies were done to measure the impact of AS6 DNAzyme (SEQ ID NO:6) on MMP-9 function by invasive properties of treated cells. COS-7-NG, rate C6, and human SNB19 cells were transfected with fluorescently labeled AS6 (SEQ ID NO:6) and control oligonucleotides (S6 or scrambled catalytic domain oligonucleotides (SEQ ID NOs:18 or 20, respectively)), and at 18 hours post-transfection, fluorescent positive cells were sorted by FACS, collected, and added to the Boydan Invasion Chamber. After 24 hours incubation, the number of cells that migrated though the extracellular membrane (ECM) was quantitated by colorimetric assay according to the manufacturer's protocol. As shown in FIG. 6, the COS-7 NC (FIG. 6A), C6 glioma (FIG. 6B), and SNB19 glioma (FIG. 6C) cells treated with AS6 were 25%, 70%, and 67% less invasive than the cells treated with the control S6 oligonucleotide or DOTAP alone, respectively ($P<0.05$).

Example 4

Figure 7:
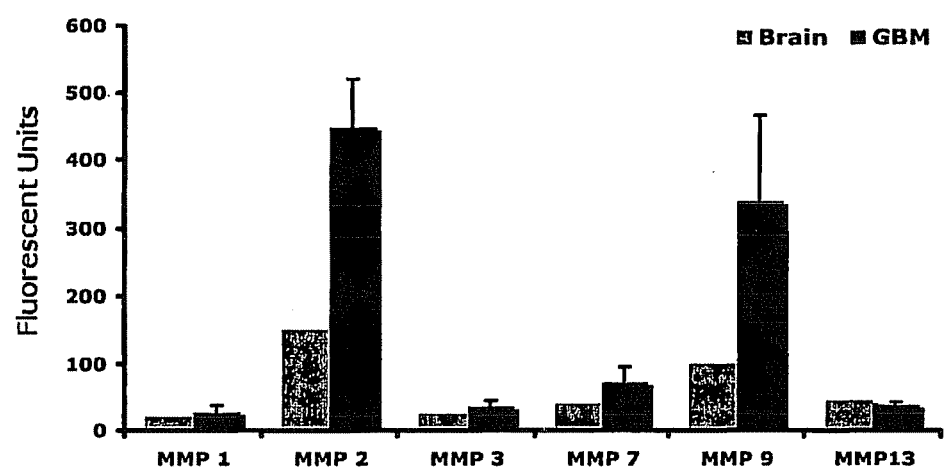
FIG. 7 is a graph depicting gene expression analysis of MMPs in human GBMs vs. normal adult brain samples. Bar graph values represent the average of fluorescent results from individual samples. This data demonstrates that expression of MMP-2 and MMP-9 at the mRNA level are up-regulated in GBMs relative to normal adult brain.

Expression of MMP-9 in Human Glioblastoma Patients and Rat Intracranial Glioma Models To confirm previous observations that MMP-9 expression is up-regulated in glioma, MMP-9 gene expression in 11 gliomas from human patients presenting with a first diagnosis of glioblastoma multiforme (GBM) were analyzed and compared to that of normal brain pooled from three human specimens. As shown in FIG. 7, microarray analysis demonstrated that MMP-9 mRNA levels are significantly up-regulated in GBMs from these patients compared to normal adult brain.

A rat allograft intracranial glioma model was then used to further investigate the expression of MMP-9 in vivo and identify cell lines that could be used for in vivo therapeutic testing. The C6 glioma cell lines, which was originally cloned from rat tumors induced by N-nitrosomethylurea, was used for these studies because it is well characterized and acceptable for generating a rat model of high-grade intracranial glioma, as is generally known in the art. To enhance visual analysis of glioma developing in the brain, the C6 glioma cell line that stably expresses GFP was used.

Figure 8:
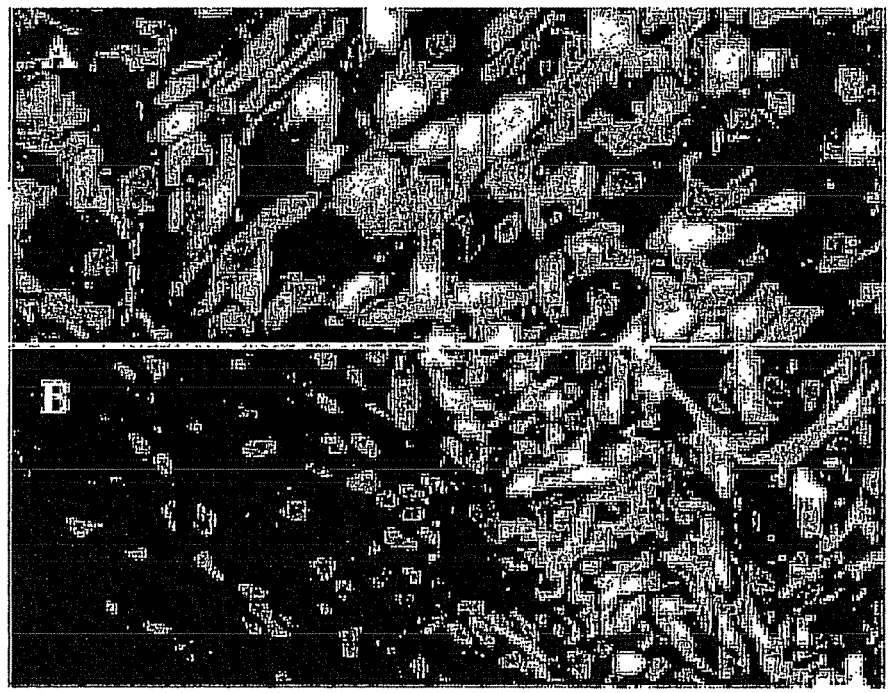
FIGS. 8A-8B are photomicrographs showing MMP-9 immunoreactivity in C6 intracranial glioma. MMP-9 was found to up-regulated in both the tumor center (FIG. 8A) and edge (FIG. 8B) in C6 intracranial glioma.

Immunohistochemical analysis of C6 intracranial glioma and surrounding brain tissue demonstrated the presence of MMP-9 in intracranial glioma and brain tissue at the tumor-tissue interface with brain parenchyma (FIGS. 8A and 8B). This was in direct contrast to the level of MMP-9 in the brain in healthy adult rats, or rats mock inoculated with PBS where MMP-9 was low to undetectable (not shown). Thus, in addition to the expression of MMP-9 by glioma cells, the data suggests that glioma induces brain tissues to up-regulate MMP-9 expression as well.

Example 5

Figure 3:
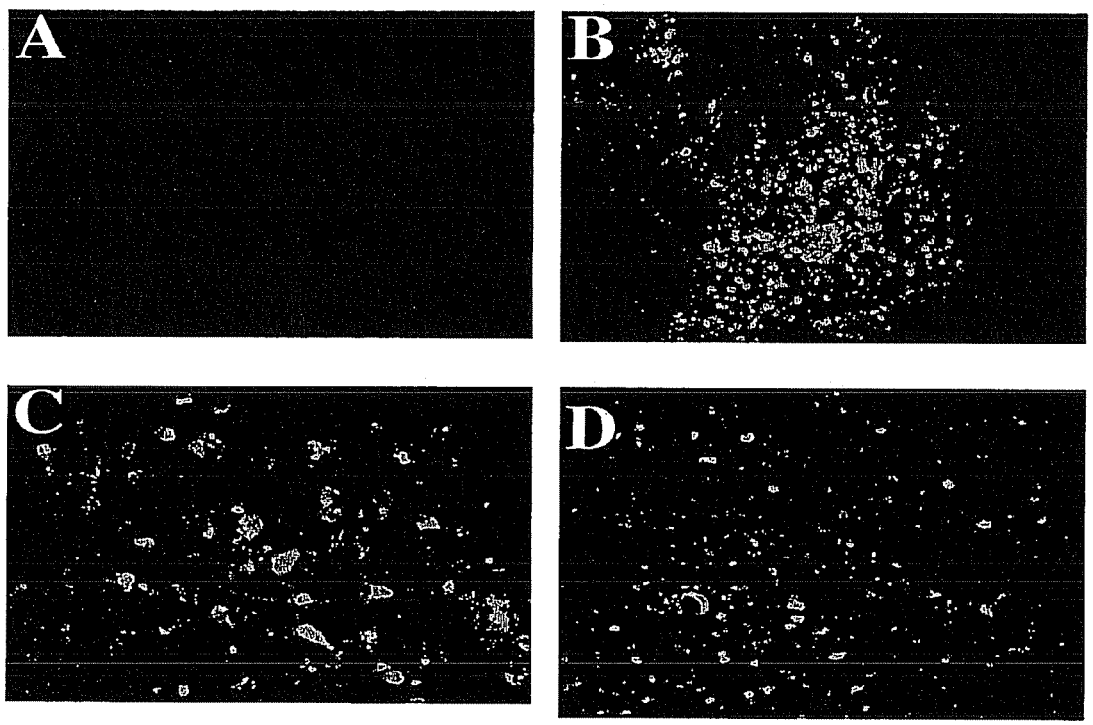
FIGS. 3A-3D are photomicrographs showing distribution and cellular uptake of fluorescently labeled DNAzyme. Labeled DNAzyme was delivered intracranially via miniosmotic pump over a period of 7 days to healthy Sprague-Dawley Rats. Brains were then prepared, sectioned, and viewed under fluorescent microscope.

In Vivo Therapeutic Testing of Anti-MMP-9 DNAzymes in a Rat Intracranial Glioma Model The in vitro studies, microarray data, and in vivo intracranial rat glioma immunohistochemical studies prompted development of a pilot therapeutic study of the treatment of the rat intracranial glioma model with anti-rat-MMP-9 DNAzyme oligos (SEQ ID NO:22). To test the ability of DNAzyme oligos to be taken up by cells in vivo, oligos were fluorescently labeled as described above, injected into the brain of adult rats, and the animals sacrificed at 3 and 24 hours after injection. As shown in FIG. 9A, the cells around the injection site took up the fluorescent oligos 3 hr after injection of 20 μg of DNAzyme in a volume of 10 μl of PBS. A higher magnification view demonstrates individual cells that have taken up the fluorescent oligo (FIG. 9B). Interestingly, the higher power view revealed that the fluorescent oligos clustered in some of the cells analyzed. When the oligos were allowed to incubate for up to 24 hours, the results were similar but the diffusion field was slightly larger (data not shown). To determine whether DNAzyme oligonucleotides would have adequate stability and distribution when delivered to the tumor bed a similar set of experiments were undertaken using the ALZET® mini-osmotic pump system. The pump was assembled, filled with fluorescently labeled AS6 in PBS, and inserted into the back of animals. Labeled DNAzyme (20 μg/day) was delivered intracranially at a rate of 1 μl/h over a period of 7 days to healthy Sprague-Dawley Rats. This does is based on the results obtained from direct injection of DNAzyme into the brain of animals with intracranial glioma described above. The animals were then sacrificed, their brains were prepared, sectioned, and viewed under a fluorescent microscope. As shown in FIG. 3, fluorescently labeled oligonucleotides could be easily detected in a dense distribution in and around the brain, emanating from the canula tip (FIGS. 3B and 3C) as well as in remote distances from the canula tip at up to 7 days (FIG. 3D). This demonstrated that the DNAzymes are stable and can distribute both into and distant from the tumor bed, indicating a wide distribution and relative access to both primary tumor and micro-foci of the invading tumor.

Figure 10:
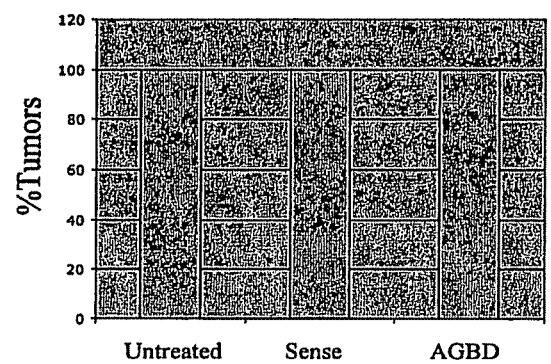
FIGS. 10A and 10B are graphs showing the effect of AS6 (AGBD) on graft success and tumor size.
FIGS. 10C-10F are H&E and fluorescent photomicrographs demonstrating the average size of glioma in rats treated with control oligo (S6) and AS6 DNAyme oligo. A significant reduction in tumor size was noted in rats treated with the AS6 oligos.
Figure 10:
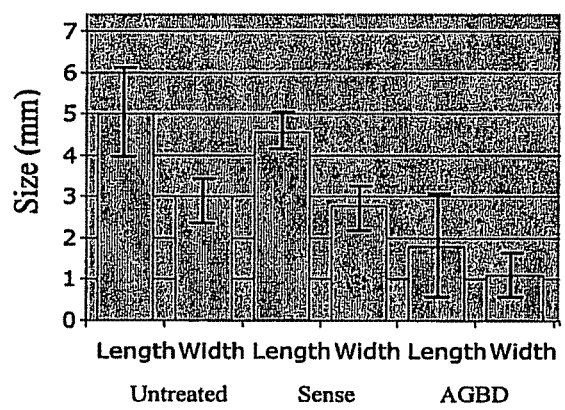

The efficacy of AS6 oligos in treating C6 glioma in a rat intracranial glioma model was then tested. For these experiments, the animals were divided into three groups: (1) intracranial glioma, untreated, (2) intracranial glioma, treated with sense anti-MMP-9 DNAzyme control oligos (SEQ ID NO:23), and (3) intracranial glioma, treated with AS6 therapeutic oligos (SEQ ID NO:22). Animals were inoculated with C6 glioma as described above in the experimental methods section, and the treated groups (both control or AS6) were given 20 fig of oligo resuspended in 10 μl of PBS on days 0, 3, 6, 9, and 12. Animals were sacrificed and analyzed on day 15. All animals in the untreated and DNAzyme control groups developed tumor of typical size and appearance at the time of sacrifice (FIG. 10 and data not shown). The average size of tumor in the untreated group was 5 mm×3 mm (length and width, respectively), and the average size of tumor in the control DNAzyme treated group was 4.6 mm×2.8 mm (length and width respectively) (FIG. 10A). However, in the AS6 treated group, although all animals developed glioma, the average size of the tumor was dramatically reduced (FIG. 10B). Indeed, average size of tumors in this group was 1.8 by 1.2 (length and width respectively) (FIG. 10). These data suggest that DNAzymes targeting MMP-9 have significant potential as anti-glioma agents.

Discussion of Examples 1-5

As discussed herein and elsewhere, over expression of MMP-9 has been observed in areas of pathology of cancers as well as inflammatory or autoimmune diseases such as arthritis and multiple sclerosis. Examples 1-5 provide the first data demonstrating the effect of DNAzymes targeted against MMP-9 in a cancer model. The Examples data clearly demonstrate that at least several of the anti-MMP-9 DNAzymes tested and developed effectively target MMP-9 and thereby reduce expression at both the mRNA and protein levels. Putative secondary structure prediction of human MMP-9 mRNA by mfold version 3.1 program by Zuker and Turner (1999) showed that the target site of AS6 (SEQ ID NO:6) was mainly on a putative single stranded region, whereas AS4 (SEQ ID NO: 4) was not and thus had limited accessibility to the mRNA. This may explain in part why the AS6 was superior to the AS4 DNAzyme in in vitro studies.

The functional effect of the AS6 DNAzyme in reducing COS-7-NG invasion through basement membrane in an in vitro assay of cell invasion was also demonstrated in these Examples.

As discussed herein, it has been reported that MMP-9 is associated with high-grade gliomas and may contribute significantly to their ability to migrate throughout the brain. The data provided by these Examples confirms these studies, in that MMP-9 was significantly up-regulated in the tumors of patients examined. MMP-9 expression in glioma was further confirmed in immunohistochemical studies of MMP-9 expression in rat gliomas allografted into rat brain to create an intracranial glioma model. In these Examples, it was found that the glioma and surrounding brain parenchyma up-regulated MMP-9 when compared to healthy adult rat brain or adult rat brain mock inoculated with PBS where MMP-9 could not be detected (FIG. 7).

Figure 9:
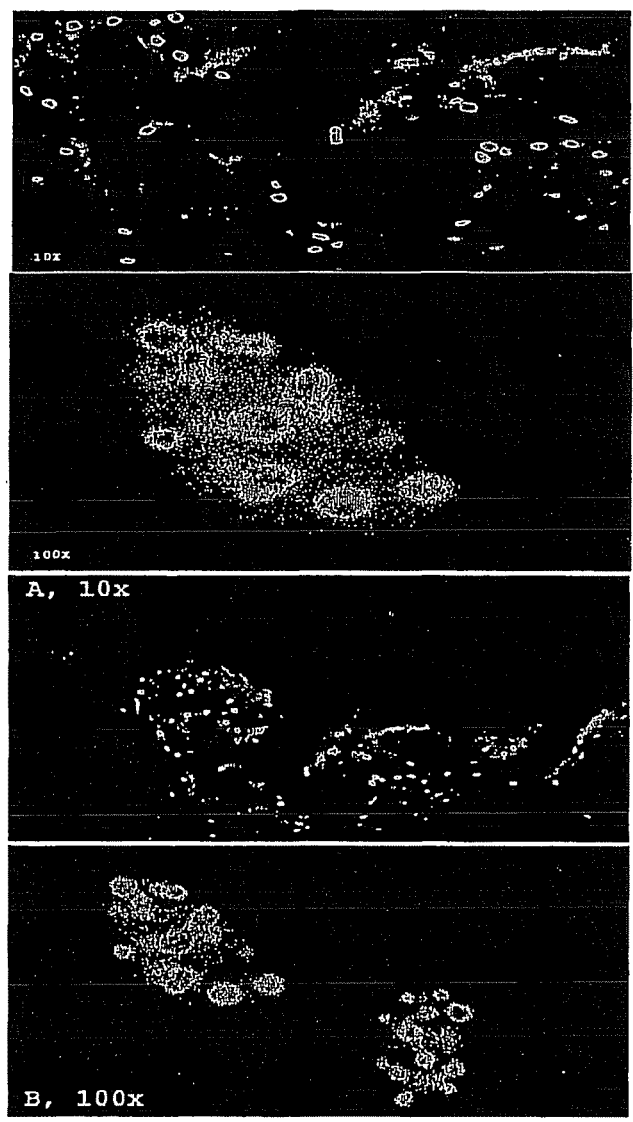
FIG. 9 is a photomicrograph showing uptake of fluorescently labeled oligos after being injected into brain. Antisense oligo (AS6) was injected into rat brain, and the rat was sacrificed after 3 hr. The fluorescent labeled (AS6) oligo was taken up by the cells around the injection site as shown by A, 10×. At a higher magnification (B, 100×), individual cells with intracellular oligo clusters were noted.

Using the rat intracranial glioma model the efficacy of anti-MMP-9 DNAzyme on intracranial glioma was tested. First, fluorescently labeled oligonucleotides were injected into the brain of healthy adult rats and found that the oligos diffused from the site of injection and could be found inside cells at both 3 and 24 hours (FIG. 9). These results are consistent with work by others showing that when DNAzymes were administered they were taken up by liver and kidney cells by phagocytosis, pinocytosis, and other mechanisms yet to be described. When treated with the anti-MMP-9 DNAzyme oligos, the tumors were greatly reduced in size (FIG. 10B). The control animals and animals treated with the sense DNAzymes had no significant reduction in tumor volume (FIG. 10B).

Prior to the presently disclosed subject matter, there were no known reports of studies that investigate DNAzymes targeted to any gene associated with gliomas. DNAzymes are advantageous when compared to drugs designed to inhibit MMPs because of their specificity and lack of side effects. Significant side effects associated with drugs that target MMPs include but are not limited to fatigue, anorexia, nausea, vomiting, asthenia, and inflammatory polyarthritis. In addition, most clinical trials to date with these drugs have failed to show any significant clinical benefit to patients with cancer.

Pharmacodynamic and pharmacokinetic studies in animals have demonstrated that nuclease resistant ribozymes are taken up efficiently into cells in vivo. However, because cellular fluids and tissues contain abundant ribonucleases, an all-RNA ribozyme is likely to be degraded too rapidly to function well in vivo. Efficient delivery of antisense RNA and ribozymes into cells is further complicated by the need for a carrier, usually a retroviral vector or a lipid-based compound. Delivering antisense and ribozymes in this manner is associated with many technical difficulties and added problems. High concentrations of virus and impurities in viral preparations can provoke an immediate inflammatory response after injection. Adenoviral vectors used continue to express native viral proteins and have been associated with inflammatory responses a few weeks after injection. Alternatively, degradation appears to be less of a concern with DNAzymes as suggested by previous observations that naked DNA oligonucleotides are taken up efficiently by liver, kidney, and lung after intravenous administration {Khachigian, 2000}. See also, Example 6 herein below showing stability of DNAzymes of the presently disclosed subject matter over five days. Further, carriers such as viral vectors and lipid-based compounds are not necessarily required in order to deliver the DNAzymes to target cells. As such, DNAzymes can provide a desirable approach for targeted disruption of gene expression and the data provided in the above Examples shows the successful application of DNAzyme technology to the disruption of MMP-9 expression both in vitro and in vivo.

In conclusion, the above Examples provide data showing design, selection, and testing of DNAzyme oligonucleotides that target human and rat MMP-9. The data demonstrates in vitro the ability of these molecules to decrease MMP-9 mRNA and protein express, as well as decrease invasive behavior of cells. The data further demonstrates in human and rat gliomas that MMP-9 is expressed by tumor cells in levels that exceed that of normal brain. Further, the data shows that the presence of glioma induces non-cancer cells surrounding the tumor to also up-regulate MMP-9 expression. These in vitro and in vivo data led to further development of the in vivo studies using a rat intracranial glioma model disclosed in these Examples. The ability of oligos directly injected into the brain to be taken up by brain cells was first tested. The efficacy of multiple dosing of oligos to treat intracranial glioma in rats was then tested, and a significant reduction of tumor size in all animals tested was found. The data presented in these Examples clearly show DNAzyme utility in vitro and in vivo in the treatment of brain cancers.

Example 6

Stability of DNAzymes

Figure 11:
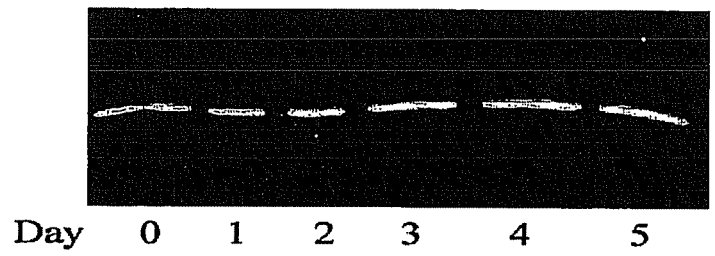
FIG. 11 is a photograph of a 6% polyacrylamide-urea gel showing that DNAzyme is stable over a five day test period at 37° C. DNAzyme was incubated in PBS at 37° C. Aliquots were removed at indicated time intervals and the amount of DNAzyme remaining as a function of time was determined by applying the aliquots to a 6% polyacrylamide-urea gel.

Stability of the DNAzymes of the presently disclosed subject matter in solution were examined by incubating 20 µg of DNAzyme oligonucleotides in PBS for 5 days at 37° C. Aliquots were removed at different time intervals and the amount of DNAzyme remaining as a function of time was determined by applying the oligonucleotides to a 6% polyacrylamide-urea gel. As demonstrated in FIG. 11, DNAzyme oligonucleotides were stable in PBS and no significant degradation at 37° C. was observed over the 5 days period.

Example 7

Safety and Efficacy of DNAzymes in Brain

To substantiate the safety and determine the maximum tolerated dose (MTD) and efficacy of DNAzymes delivered directly to brain tissue, the effects of exposing healthy brain tissue of live animals to different amounts of DNAzyme oligonucleotides was determined by real-time clinical observation and post-mortem by neurohistopathological analysis. Oligonucleotides were delivered into the anatomical areas that correspond to where glioma will be implanted in the intracranial glioma model (3 mm lateral to bregma along the coronal suture) using a mini osmotic pump system.

It has been suggested that multiple injections may injure the brain tissue causing inflammation, up-regulation of cytokines, chemokines, as well as MMPs. Therefore, to overcome these obstacles, an alternative delivery system to direct injection was used, i.e. the ALZET® mini osmotic pump system (DURECT Corporation, Cupertino, Calif., U.S.A.). These pumps can be filled with oligonucleotides in solution, and will deliver the oligonucleotides by an osmotic displacement mechanism. Mini-osmotic pumps have a distinct advantage over direct injection for delivery of therapeutic agents such as DNAzymes because they maintain a well-defined and consistent pattern of delivery and tissue exposure over a significant period of time. Molecular weight, physical conformation, and chemical properties do not affect the delivery rate of a given compound. This mechanism of delivery is similar to that available for delivery of agents to the brain in human patients (Kisker et al., 2001 and Shoichet and Winn, 2000). Direct intraparenchymal nervous system delivery of substances via the ALZET® pump has been used by many investigators and applied in several clinical conditions, even to tumors in regions of the brain that are considered to be inoperable. See, e.g. Carson et al., 2002. The methodology for using the ALZET® mini-osmotic pump system to deliver small molecules to adult rat brain is well described.

Figure 12:
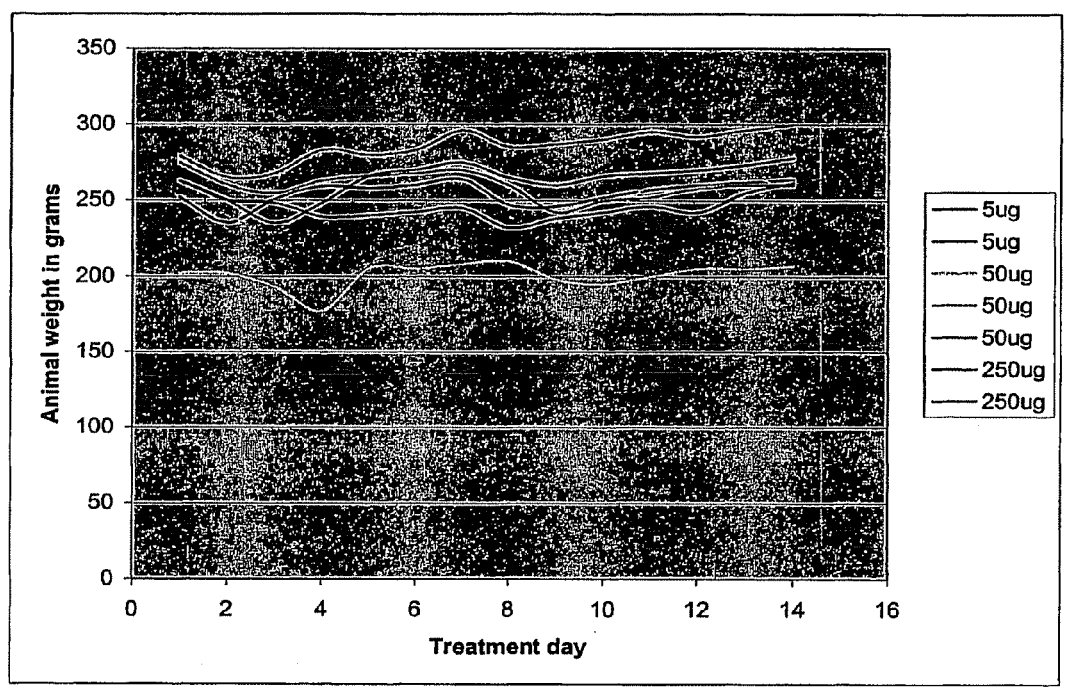
FIG. 12 is a graph showing safety and efficacy of DNAZyme treatment of normal brain.

Adult Sprague-Dawley rats (200-250 g in weight) were used for all studies. The ALZET® osmotic pumps (DURECT Corporation, Cupertino, Calif., U.S.A.) were assembled according to the manufacturer's protocols, loaded with different amounts of DNAzyme in PBS (5 µg-250 µg) and inserted into the backs of the animals. The DNAzymes were then infused into the brain at a rate of 1 µL/h over a 14 day treatment window. The animals were weighed daily and given modified Glasgow Coma Scale for rodents (neurological functioning score). The possible coma scale score ranges from 3 to 11 and is calculated as follows:
LOC
4: Moving spontaneously at any time prior to being handled.
3: Not moving, but moves spontaneously when picked up for 3 seconds by tail and put back down.
2: Does not move after being picked p, but moves with pain stimulus.
1: Does not move with pain stimulus.
Motor
3: Ambulates well
2: Ambulates but with some notable paresis (motion hemi/quadri/fore limb/bind limb involvement)
1: Can not ambulate due to plegia (motion hemi/quadri/fore limb/bind limb involvement)
Eyes
4: Open spontaneously
3: Open to stimulation
2: Open to pain
1: No response No animal lost weight or scored less than 11 at any time point during the treatment. See FIG. 12.

The animals were then sacrificed on day 15 by transcardiac perfusion of heparinized saline followed with 4% paraformaldehyde under deep anesthesia. The brain were removed, fixed in 4% paraformaldehyde for 2 hours at 4° C., and sectioned on a cryostat at 16 µm. The brain sections are examined for signs of DNAzyme toxicity. According to hematoxylin-eosin staining no basic neuropathological effect due to the DNAzyme treatment was observed.

Example 8

Anti-MMP-2 DNAzymes

Microarray analysis of human glioma samples suggests that MMP-2 also contributes to the invasiveness and/or pathogenesis of glioma. Thus, the lack of complete inhibition of C6 and/or SNB19 glioma cells invasion in vitro by AS6 (SEQ ID NO:6) may be due to contribution of MMP-2 in invasion. To address this issue several anti-MMP-2 DNAzymes were generated and their efficiency in down regulating MMP-2 expression and in reducing invasive behavior of C6, U87MG, and SNB19 cells in vitro was investigated.

Figure 13:
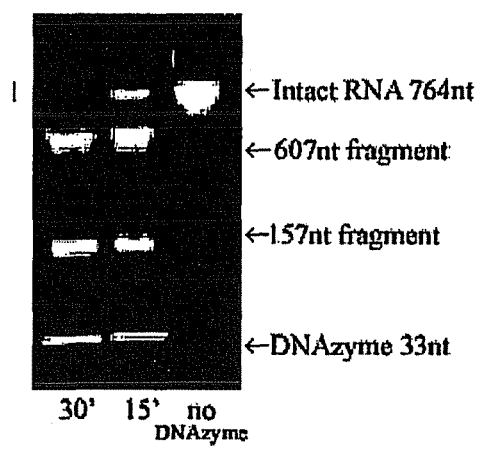
FIG. 13 is a photograph of a urea-polyacrylamide gel showing cleavage of MMP-2 RNA transcript by 72k01 DNAzyme. MMP-2 RNA (764 nt) was incubated alone or with 72k01 DNAzyme in a 2:1 ratio in 50 mM Tris, pH 7.5 and 10 mM MgCl$_2$ at 37° C. for 15 minutes or 30 minutes and applied to a 4% urea-polyacrylamide gel.
Figure 14:
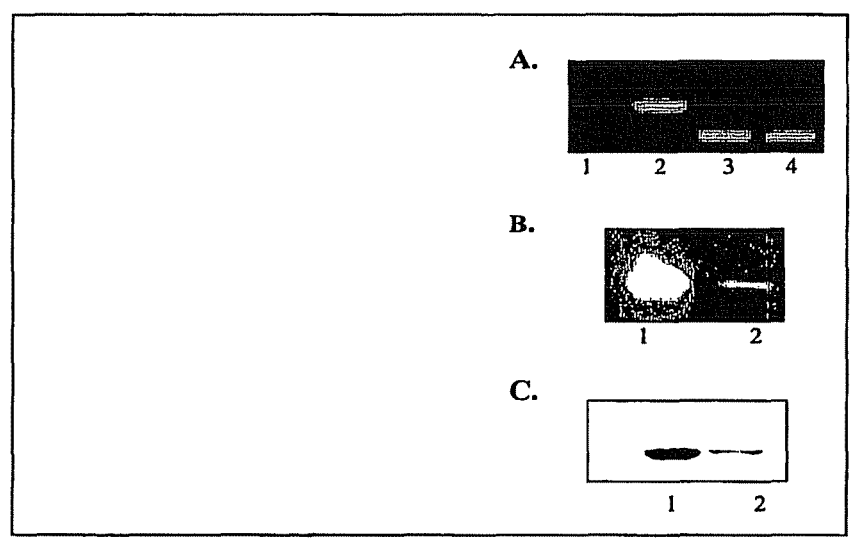
FIGS. 14A-14C show the effect of 72K01 on MMP-2 production in U87MG glioma in vitro.
Figure 15:
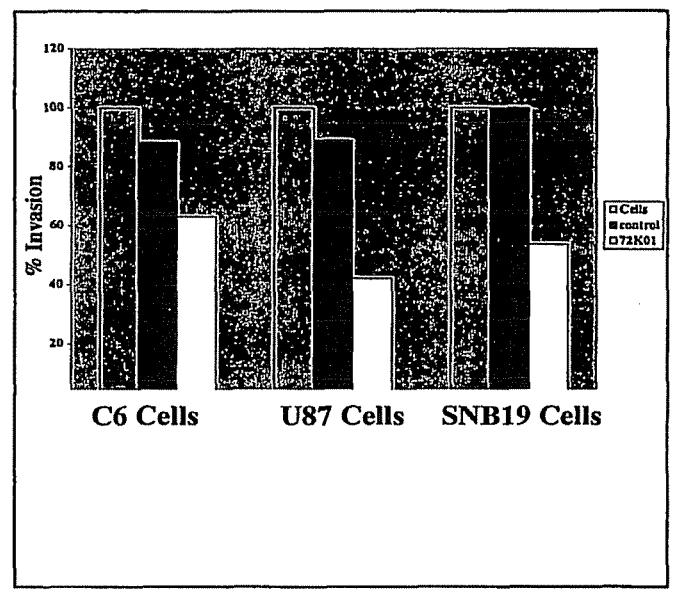
FIG. 15 is a graph showing the percentage ratio of C-6, U87, and SNB19 glioma cells that invaded the ECM layer after treatment with 72K01 anti-MMP-2 DNAzyme (72K01) or control DNAzyme (control) against that of cells treated with DOTAP alone (cells).

U87MG (ATCC #HTB-14) cell line is a high-grade, aggressive, malignant human glioma, derived from a malignant glioma in a 44-year-old Caucasian female. As shown in FIGS. 13-15, anti-MMP-2 DNAzyme (referred to herein as 72 K01; SEQ ID NO:12) was able to cleave MMP-2 mRNA in vitro, to decrease the production of MMP-2 mRNA and the protein in U87 glioma cells, and to reduce the invasiveness of rat C6 and human U87MG and SNB19 glioma cells in vitro. The 72K01, 5'-CCTTCAGCAGGCTAGCTACAAC-GAAAACAGGTT-3' (SEQ ID NO:12), encodes for the catalytic domain sequence of DNAzyme flanked by 9 bases (substrate binding domains) complimentary to the coding sequence of human MMP-2 gene. In the control DNAzyme, 5'-CTAGTCAGCGGCTAGCTACAACGATAAGCTGCT-3' (SEQ ID NO:28), the conserved catalytic domain sequence of DNAzyme is flanked by 9 random base sequence.

Similar to AS6 (SEQ ID NO:6) in the previous Examples, 72K01 oligonucleotide targeted against a specific region of the MMP-2 mRNA and a control DNAzyme (scrambled oligonucleotides) were tested for their ability to cleave the MMP-2 mRNA in vitro. The MMP-2 mRNA transcript was generated as described for that of MMP-9 (Material and Methods section of Examples 1-5). As shown in FIG. 13, 72K01 completely cleaved the MMP-2-RNA into a 607 and a 157 nt fragments in 30 min. The control DNAzyme at the same concentration did not have any effect on MMP-2-RNA.

To further assess the effect of 72K01 on MMP-2 production in vitro, human U87MG glioma cells that express MMP-2 but lack MMP-9 were transfected with either control or 72K01 as described above (Material and Methods section of Examples 1-5). Twenty four hours after transfection, the cells were harvested, total RNA was extracted and examined for the presence of MMP-2 mRNA by RT-PCR (FIG. 14A). The presence of MMP-2 enzyme activity and protein in the condition media were determined by gelatin gel zymography (FIG. 14B) and western blot analysis (FIG. 14C) using antibody against MMP-2. As demonstrated in FIG. 14, the 72 K01 DNAzyme significantly reduced the level of the MMP-2 mRNA (FIG. 14A, lane 1) and protein (FIG. 14B, C, lane 2) in U87MG cells.

Using an in vitro cell invasion assay the effect of 72K01 on the invasive behavior of rat C6, human U87MG, and human SNB19 Glioma cells was evaluated. The cells were transfected and added to the basement membrane model as previously described in the Examples above (Material and Methods section of Examples 1-5). After 24 hours incubation, the number of cells that migrated though the ECM was quantitated by colorimetric assay according to the manufacturer's protocol (CHEMICON, Temecula, Calif., U.S.A.). As shown in FIG. 15, the C6, U87MG, and SNB19 glioma cells treated with 72K01 were 37%, 68%, and 47% less invasive than the cells treated with the control DNAzyme, respectively. These data indicated that MMP-2 as well as MMP-9 significantly contribute to invasive behaviour of glioma cells and suggest that down-regulation of MMP-2 and/or MMP-9 expression in glioma by 72K01 and AS6 should substantially inhibit the invasive behaviour of glioma in vivo.

Example 9

Effect of Both MMP-2 and MMP-9 DNAzymes on Glioma Cell Invasive Behavior

Figure 16:
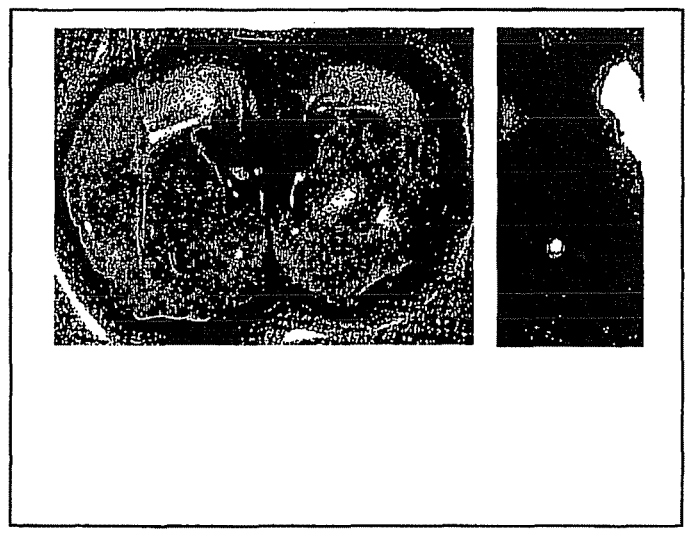
FIG. 16 is a photomicrograph showing targeting of Evan's blue dye to the SVZ of adult rat brain using stereotaxic coordinates relative to bregma. Low (left panel) power coronal section of brain tissue and higher (right panel) power showing ventricle with diffusion of dye (dark stain) outwards.

Microarray data (FIG. 7), in vitro studies, and in vivo intracranial rat glioma immunohistochemical studies prompted development of a therapeutic study for the treatment of the rat intracranial glioma model with AS6 (anti-MMP-9 DNAzyme) and 72K01 (anti-MMP-2 DNAzyme) together. First, to test the ability to target specific areas, a stereotaxic frame was use to inject Evan's blue dye into specific areas of the brain. For example, FIG. 16 shows an injection designed to target the SVZ, an area where it has been previously demonstrated that MMP-9 is significantly expressed in the presence of intracranial glioma.

Figure 17:
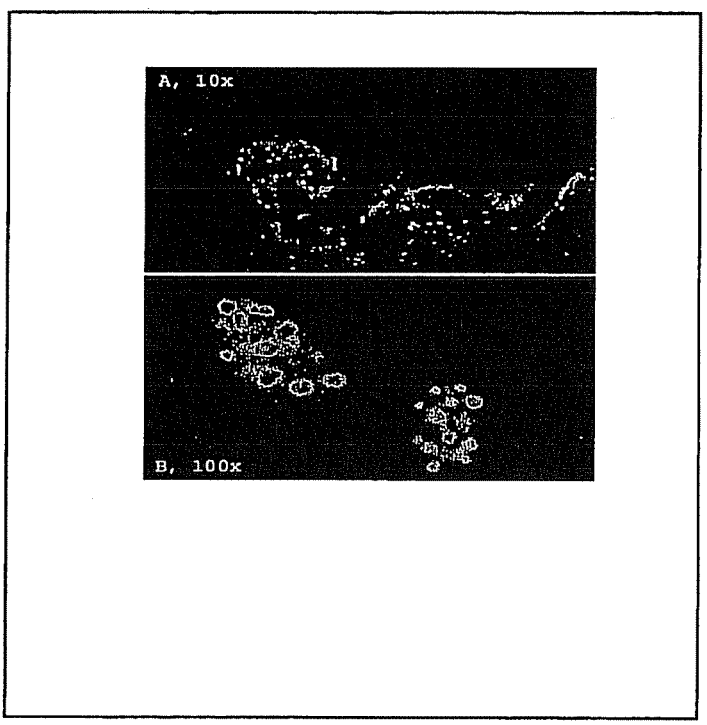
FIG. 17 is a photomicrograph showing uptake of fluorescently labeled oligos after being injected into brain. AS6 (anti-MMP-9 DNAyme) was injected into rat brain, and the rat was sacrificed after 3 hours. The fluorescent labeled oligonucleotides were taken up by the cells around the injection site as shown by A, 10×. At a higher magnification (B, 100×), individual cells with intracellular oligonucleotides clusters were noted.

It was found that most areas of interest could be marked with dye, thus paving the way to target these areas with DNAzyme oligonucleotides. To test the ability of DNAzyme oligonucleotides to be taken up by cells in vivo, oligonucleotides were labeled with green fluorescent tags and injected into the brain of rats and the animals sacrificed at 3 and 24 hours after injection. As shown in FIG. 17A, the cells around the injection site took up the fluorescent oligonucleotides 3 hours after injection of 20 μg of DNAzyme in a volume of 10 μl in PBS. A higher magnification view (100×) demonstrates individual cells that have taken up the fluorescent oligonucleotide (FIG. 17B). Interestingly, the higher power view revealed that in some cells the fluorescent oligonucleotides clustered. When the oligonucleotides were allowed to incubate for up to 24 hours the results were similar but the diffusion field was slightly larger. These results are consistent with previous observations demonstrating that when naked oligonucleotides were administered by IV injection, they were taken up by the liver and kidney cells either by phagocytosis, pinocytosis, or other mechanisms yet to be described. See Levin, 1999 and Butler et al., 1997.

Figure 18:
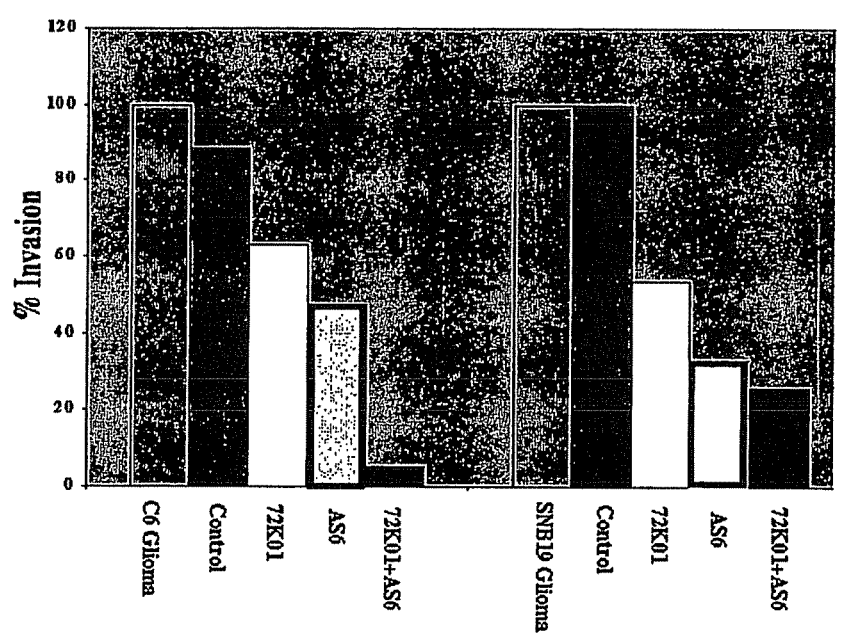
FIG. 18 is a graph showing the percentage ratio of C6 and SNB19 glioma cells that invaded the ECM layer after treatment with 72K01 (anti-MMP-2 DNAzyme), AS6 (anti-MMP-9 DNAzyme), 72K01/AS6 combination, or control DNAzyme against that of cells treated with DOTAP alone.

In conclusion, C6 and SNB19 glioma cells were transfected with both AS6 (anti-MMP-9) and 72K01 (anti-MMP-2) DNAzymes and the effect of double transfection on invasive behavior of these cell lines on matrigel matrix investigated as described above. As shown in FIG. 18, the combination of AS6 and 72K01 reduced the invasive behavior of both C6 and SNB19 in vitro by 95% and ~80%, respectively. This data clearly demonstrates that anti MMP-DNAzymes can efficiently and effectively be used to fight glioma either alone or in synergistic combinations.

REFERENCES

The reference listed below as well as all references cited in the specification are incorporated herein by reference to the extent that they supplement, explain, provide a background for or teach methodology, techniques and/or compositions employed herein.

Adelman J P, Hayflick J S, Vasser M & Seeburg P H (1983) In Vitro Deletional Mutagenesis for Bacterial Production of the 20,000-Dalton Form of Human Pituitary Growth Hormone. *DNA* 2:183-193.

Alam J & Cook J L (1990) Reporter genes: application to the study of mammalian gene transcription. *Anal Biochem* 188:245-254.

Altschul S F, Gish W, Miller W, Myers E W & Lipman D J (1990) Basic Local Alignment Search Tool. *J Mol Biol* 215:403-410.

Ausubel F (ed) (1995) *Short Protocols in Molecular Biology*, 3rd ed. Wiley, New York, N.Y., United States of America.

Ausubel F M, Brent R, Kingston R E, Moore D D, Seidman J G, Smith J A & Struhl K, eds. (1992) Current Protocols in Molecular Biology. Wiley, New York.

Bass B L (2001) RNA interference: The short answer. *Nature* 411:428-429.

Beaucage & Iyer (1993) The functionalization of oligonucleotides via phosphoramidite derivative. *Tetrahedron* 49:1925-1963.

Beigelman L, McSwiggen J A, Draper K G, Gonzalez C, Jensen K, Karpeisky A M, Modak A S, Matulic-Adamic J, DiRenzo A B, Haeberli P, et al. (1995) Chemical modification of hammerhead ribozymes. Catalytic activity and nuclease resistance. *J Biol Chem* 270:25702-25708.

Bellon L, Workman C T, Jarvis T C & Wincott F E (1997) Post-synthetically ligated ribozymes: an alternative approach to iterative solid-phase synthesis. *Bioconjugate Chem* 8:204-212.

Bernstein E, Caudy A A, Hammond S M & Hannon G J (2001) Role for a bidentate ribonuclease in the initiation step of RNA interference. *Nature* 409:363-366.

Brennan T, Biddison G, Frauendorf A, Schwarcz L, Keen B, Ecker D J, Davis P W, Tinder R & Swayze E E (1998) Two-dimensional parallel array technology as a new approach to automated combinatorial solid-phase organic synthesis. *Biotechnol Bioeng* 61:33-45.

Brickell P M (1992) The P60c-Src Family of Protein-Tyrosine Kinases: Structure, Regulation, and Function. *Crit. Rev Oncog* 3:401-446.

Brummelkamp T R, Bernards R & Agami R A (2002) System for stable expression of short interfering RNAs in mammalian cells. *Science* 296:550-553.

Burgin A B Jr, Gonzalez C, Matulic-Adamic J, Karpeisky A M, Usman N, McSwiggen J A & Beigelman L (1996) Chemically modified hammerhead ribozymes with improved catalytic rates. *Biochemistry* 35:14090-14097.

Burlina F, Favre A & Fourrey J L (1997) Chemical engineering of RNase resistant and catalytically active hammerhead ribozymes. *Bioorg Med Chem* 5:1999-2010.

Butler, M, Stecker, K, and Bennett, C F (1997) Cellular distribution of phosphorothioate oligodeoxynucleotides in normal rodent tissues. *Lab Invest* 77: 379-388.

Canadian Patent Application No. 2,359,180

Caruthers M H, Beaton G, Wu J V & Wiesler W (1992) Chemical synthesis of deoxyoligonucleotides and deoxyoligonucleotide analogs. *Methods Enzymol* 211:3-19.

Carson B S, Wu Q, Tyler B, Sukay L, Raychaudhuri R, DiMeco F, Clatterbuck R E, Olivi A, and Guarnieri M (2002) New approach to tumor therapy for inoperable areas of the brain: chronic intraparenchymal drug delivery. *J Neurooncol* 60:151-8.

Christoffersen and Marr (1995) *J Med Chem* 38: 2023-2037.

Cipolla D C, Gonda I, Shak S, Kovesdi I, Crystal R & Sweeney T D (2000) Coarse Spray Delivery to a Localized Region of the Pulmonary Airways for Gene Therapy. *Hum Gene Ther* 11:361-371.

Clifford S C & Maher E R (2001) Von Hippel-Lindau Disease: Clinical and Molecular Perspectives. *Adv Cancer Res* 82:85-105.

Cubitt A B, Heim R, Adams S R, Boyd A E, Gross L A & Tsien R Y (1995) Understanding, Improving and Using Green Fluorescent Proteins. *Trends Biochem Sci* 20:448-455.

Dachs G U & Tozer G M (2000) Hypoxia Modulated Gene Expression: Angiogenesis, Metastasis and Therapeutic Exploitation. *Eur J Cancer* 36:1649-1660.

Dai S, Huang M L, Hsu C Y & Chao K S (2003) Inhibition of hypoxia inducible factor 1alpha causes oxygen-independent cytotoxicity and induces p53 independent apoptosis in glioblastoma cells. *Int J Radiat Oncol Biol Phys* 55:1027-36.

De Mesmaeker A, Waldner A, Lebreton J, Fritsch V & Wolf R M (1994) Novel Backbone Replacements for Oligonucleotides, in *Carbohydrate Modifications in Antisense Research*, American Chemical Society, Washington, D.C., Symposium Series No. 580:24-39.

Earnshaw D J & Gait M J (1998) Modified oligoribonucleotides as site-specific probes of RNA structure and function. *Biopolymers* 48:39-55.

Elbashir S M, Harborth J, Lendeckel W, Yalcin A, Weber K & Tuschl T (2001a) Duplexes of 21-nucleotide RNAs mediate RNA interference in cultured mammalian cells. *Nature* 411: 494-498.

Elbashir S M, Lendeckel W & Tuschl T (2001b) RNA interference is mediated by 21- and 22-nucleotide RNAs. *Genes Dev* 15:188-200.

Elbashir S M, Martinez J, Patkaniowska A, Lendeckel W & Tuschl T (2001c) Functional anatomy of siRNAs for mediating efficient RNAi in *Drosophila melanogaster* embryo lysate. *EMBO J.* 20:6877-88.

European Patent No. 0 439 095

Fire A, Xu S, Montgomery M K, Kostas S A, Driver S E & Mello C C (1998) Chromatin silencing and the maintenance of a functional germline in *Caenorhabditis elegans*. *Nature* 391:806-811.

Fire A (1999) RNA-triggered gene silencing. *Trends Genet.* 15:358-363.

Freier S M, Kierzek R, Jaeger J A, Sugimoto N, Caruthers M H, Neilson T & Turner D H (1986) Improved Free-Energy Parameters for Predictions of RNA Duplex Stability. *Proc Natl Acad Sci USA* 83:9373-9377.

Glover D M & Hames B D (1995) DNA Cloning: A Practical Approach, 2nd ed. IRL Press at Oxford University Press, Oxford; New York.

Greenberg N M, DeMayo F J, Sheppard P C, Barrios R, Lebovitz R, Finegold M, Angelopoulou R, Dodd J G, Duckworth M L, Rosen J M et al. (1994) The Rat Probasin Gene Promoter Directs Hormonally and Developmentally Regulated Expression of a Heterologous Gene Specifically to the Prostate in Transgenic Mice. *Mol Endocrinol* 8:230-239.

Habib N A, Hodgson H J, Lemoine N & Pignatelli M (1999) A Phase I/Ii Study of Hepatic Artery Infusion with wtp53-CMV-Ad in Metastatic Malignant Liver Tumours. *Hum Gene Ther* 10:2019-2034.

Hammond S M, Bernstein E, Beach D & Hannon G J (2000) An RNA-directed nuclease mediates post-transcriptional gene silencing in *Drosophila* cells. *Nature* 404:293-296.

He T C, Zhou S, da Costa L T, Yu J, Kinzler K W & Vogelstein B A (1998) Simplified system for generating recombinant adenoviruses. *Proc Natl Acad Sci USA* 95:2509-2514.

Henikoff S & Henikoff J G (1992) Amino Acid Substitution Matrices from Protein Blocks. *Proc Natl Acad Sci USA* 89:10915-10919.

Hunziker J & Leumann C (1995) Nucleic Acid Analogues: Synthesis and Properties, in *Modern Synthetic Methods*, VCH, Basel, Switzerland 331-417.

Ivan M & Kaelin W G, Jr. (2001) The Von Hippel-Lindau Tumor Suppressor Protein. *Curr Opin Genet Dev* 11:27-34.

Joyce et al. (1989) *Nucleic Acids Research* 17: 711-712.

Karlin S & Altschul S F (1993) Applications and Statistics for Multiple High-Scoring Segments in Molecular Sequences. *Proc Natl Acad Sci USA* 90:5873-5877.

Karni R, Dor Y, Keshet E, Meyuhas O & Levitzki A (2002) Activated Pp60c-Src Leads to Elevated HIF-1 Alpha Expression under Normoxia. *J Biol Chem*: M206141200.

Karpeisky A, Gonzales C, Burgin A B & Beigelman, L (1998) Highly efficient synthesis of 2'-O-amino nucleosides and their incorporation in hammerhead ribozymes. *Tetrahedron Lett* 39:1131-1134.

Kisker O, Becker C M, Prox D, Fannon M, D'Amato R, Flynn E, Fogler W E, Sim B K, Allred E N, Pirie-Shepherd S R, and Folkman J (2001) Continuous administration of endostatin by intraperitoneally implanted osmotic pump improves the efficacy and potency of therapy in a mouse xenograft tumor model. *Cancer Res* 61:7669-74.

Kurihara T, Brough D E, Kovesdi I & Kufe D W (2000) Selectivity of a Replication competent Adenovirus for Human Breast Carcinoma Cells Expressing the MUC1 Antigen. *J Clin Invest* 106:763-771.

Lee S E, Jin R J, Lee S G, Yoon S J, Park M S, Heo D S & Choi H (2000) Development of a New Plasmid Vector with PSA-Promoter and Enhancer Expressing Tissue-Specificity in Prostate Carcinoma Cell Lines. *Anticancer Res* 20:417-422.

Levin, A A (1999) A review of the issues in the pharmacokinetics and toxicology of phosphorothioate antisense oligonucleotides. *Biochim Biophys Acta* 1489:69-84.

Limbach P A, Crain P F & McCloskey J A (1994) Summary: the modified nucleosides of RNA. *Nucleic Acids Res* 22:2183-.

Lindegaard J C, Overgaard J, Bentzen S M & Pedersen D (1996) Is There a Radiobiologic Basis for Improving the Treatment of Advanced Stage Cervical Cancer? *J Natl Cancer Inst Monogr* 21:105-112.

Loakes D (2001) Survey and summary: The applications of universal DNA base analogues. *Nucleic Acids Res* 29:2437-2447.

Maxwell P H, Pugh C W & Ratcliffe P J (2001) Activation of the HIF Pathway in Cancer. *Curr Opin Genet Dev* 11:293-299.

Miyagishi M & Taira K. (2002) U6 promoter-driven siRNAs with four uridine 3' overhangs efficiently suppress targeted gene expression in mammalian cells. *Nat Biotechnol* 20:497-500.

Murphy et al. (1989), *Proc. Natl. Acad. Sci. USA* 86: 9218-9222.

Needleman S B & Wunsch C D (1970) A General Method Applicable to the Search for Similarities in the Amino Acid Sequence of Two Proteins. *J Mol Biol* 48:443-453.

Nykanen A, Haley B & Zamore P D (2001) ATP requirements and small interfering RNA structure in the RNA interference pathway. *Cell* 107:309-321.

PCT International Publication No. WO 91/03162

PCT International Publication No. WO 92/07065

PCT International Publication No. WO 93/15187
PCT International Publication No. WO 93/23569
PCT International Publication No. WO 96/33280
PCT International Publication No. WO 97/26270
PCT International Publication No. WO 97/45550
PCT International Publication No. WO 97/47763
PCT International Publication No. WO 98/13526
PCT International Publication No. WO 98/54345
PCT International Publication No. WO 99/07409
PCT International Publication No. WO 99/32619
PCT International Publication No. WO 99/54459
PCT International Publication No. WO 00/01846
PCT International Publication No. WO 00/44895
PCT International Publication No. WO 00/44914
PCT International Publication No. WO 00/63364
PCT International Publication No. WO 01/04313
PCT International Publication No. WO 01/29058
PCT International Publication No. WO 01/36646
PCT International Publication No. WO 01/68836
PCT International Publication No. WO 01/75164
PCT International Publication No. WO 01/92513
PCT International Publication No. WO 02/044321
PCT International Publication No. WO 02/055692
PCT International Publication No. WO 02/055693
Pearson W R & Lipman D J (1988) Improved Tools for Biological Sequence Comparison. *Proc Natl Acad Sci USA* 85:2444-2448.
Perrault et al. (1990) *Nature* 344:565.
Pieken W A, Olsen D B, Benseler F, Aurup H & Eckstein F (1991) Kinetic characterization of ribonuclease-resistant 2'-modified hammerhead ribozymes. *Science* 253:314-317.
Rose M & Botstein D (1983) Construction and use of gene fusions to lacZ (beta-galactosidase) that are expressed in yeast. *Meth Enzymol* 101:167-180.
Rothmann T, Hengstermann A, Whitaker N J, Scheffner M & zur Hausen H (1998) Replication of Onyx-015, a Potential Anticancer Adenovirus, Is Independent of p53 Status in Tumor Cells. *J Virol* 72:9470-9478.
Sambrook J & Russell D W (2001) Molecular Cloning: A Laboratory Manual, 3rd ed. Cold Spring Harbor Laboratory Press, Cold Spring Harbor, N.Y.
Scaringe S A, Francklyn C & Usman N (1990) Chemical synthesis of biologically active oligoribonucleotides using beta-cyanoethyl protected ribonucleoside phosphoramidites. *Nucleic Acids Res* 18:5433-5441.
Scharfmann R, Axelrod J H & Verma I M (1991) Long-Term in Vivo Expression of Retrovirus-Mediated Gene Transfer in Mouse Fibroblast Implants. *Proc Natl Acad Sci USA* 88:4626-4630.
Semenza G L, Nejfelt M K, Chi S M & Antonarakis S E (1991) Hypoxia inducible Nuclear Factors Bind to an Enhancer Element Located 3' to the Human Erythropoietin Gene. *Proc Natl Acad Sci USA* 88:5680-5684.
Shabarova Z A, Merenkova I N, Oretskaya T S, Sokolova N I, Skripkin E A, Alexeyeva E V, Balakin A G & Bogdanov A A (1991) Chemical ligation of DNA: the first non-enzymatic assembly of a biologically active gene. *Nucleic Acids Res* 19:4247-4251.
Shoichet, M S, and Winn S R (2000) Cell delivery to the central nervous system. *Adv Drug Deliv Rev* 42:81-102.
Silhavy T J, Berman M L, Enquist L W & Cold Spring Harbor Laboratory. (1984) Experiments with Gene Fusions. Cold Spring Harbor Laboratory, Cold Spring Harbor, N.Y.
Sinkovics J G & Horvath J C (2000) Vaccination against Human Cancers (Review). *Int J Oncol* 16:81-96.
Smith T F & Waterman M (1981) Comparison of Biosequences. *Adv Appl Math* 2:482-489.
Sowter H M, Ratcliffe P J, Watson P, Greenberg A H & Harris A L. (2001) HIF-1-dependent regulation of hypoxic induction of the cell death factors BNIP3 and NIX in human tumors. *Cancer Res* 61:6669-6673.
Suit H (1996) Assessment of the Impact of Local Control on Clinical Outcome. *Front Radiat Ther Oncol* 29:17-23.
Tijssen P (1993) *Laboratory Techniques in Biochemistry and Molecular Biology-Hybridization with Nucleic Acid Probes*. Elsevier, New York, United States of America.
Turner D H, Sugimoto N, Jaeger J A, Longfellow C E, Freier S M & Kierzek R (1987) Improved parameters for prediction of RNA structure. *Cold Spring Harb Symp Quant Biol* LII:123-133.
Uhlman E & Peyman A (1990) Antisense oligonucleotides: a new therapeutic principle. *Chem Rev* 90:543-549.
Usman N, Beigelman L, Draper K, Gonzalez C, Jensen K, Karpeisky A, Modak A, Matulic-Adamic J, DiRenzo A, Haeberli P, Tracz D, Grimm S, Wincott F & McSwiggen J (1994) *Nucleic Acids Symp Ser* 31:163-164.
Usman & McSwiggen (1995) *Ann Rep Med Chem* 30: 285-294.
Usman N, Beigelman L & McSwiggen J A (1996) Hammerhead ribozyme engineering. *Curr Opin Struct Biol* 6:527-33.
Usman N & Cedergren R (1992) Exploiting the chemical synthesis of RNA. *Trends Biochem Sci* 17:334-339.
Usman N, Ogilvie K K, Jiang M Y & Cedergren R J (1987) Automated chemical synthesis of long oligoribonucleotides using 2'-O-silylated ribonucleoside 3'-O-phosphoramidites on a controlled-pore glass support-synthesis of a 43-nucleotide sequence similar to the 3'-half molecule of an *Escherichia coli* formylmethionine transfer-RNA *J Am Chem Soc* 109: 7845-7854.
U.S. Pat. No. 4,554,101
U.S. Pat. No. 5,334,711
U.S. Pat. No. 5,627,053
U.S. Pat. No. 5,672,695
U.S. Pat. No. 5,716,824
U.S. Pat. No. 5,807,718
U.S. Pat. No. 5,854,038
U.S. Pat. No. 5,858,784
U.S. Pat. No. 5,871,982
U.S. Pat. No. 5,998,203
U.S. Pat. No. 6,001,311
U.S. Pat. No. 6,013,638
U.S. Pat. No. 6,022,737
U.S. Pat. No. 6,057,156
U.S. Pat. No. 6,103,890
U.S. Pat. No. 6,127,173
U.S. Pat. No. 6,136,295
U.S. Pat. No. 6,248,878
U.S. Pat. No. 6,251,666
U.S. Pat. No. 6,300,074
U.S. Pat. No. 6,326,174
U.S. Pat. No. 6,361,941
U.S. Pat. No. 6,566,127
U.S. Pat. No. 6,586,238
U.S. Pat. No. 6,602,858
U.S. Pat. No. 6,617,438
U.S. Pat. No. 6,623,962
U.S. Pat. No. 6,686,463
Valter M M, Hugel A, Huang H J, Cavenee W K, Wiestler O D, Pietsch T & Wernert N (1999) Expression of the Ets-1 Transcription Factor in Human Astrocytomas Is Associated with Fms-Like Tyrosine Kinase-1 (Flt-1)/Vascular Endothelial Growth Factor Receptor-1 Synthesis and Neoangiogenesis. *Cancer Res* 59:5608-5614.

Verma S & Eckstein F (1998) Modified oligonucleotides: synthesis and strategy for users. *Annu Rev Biochem* 67:99-134.

Vose J M & Armitage J O (1995) Clinical Applications of Hematopoietic Growth Factors. *J Clin Oncol* 13:1023-1035.

Wianny F & Zernicka-Goetz M (1999) Specific interference with gene function by double-stranded RNA in early mouse development. *Nature Cell Biol* 2:70-75.

Williams R S, Thomas J A, Fina M, German Z & Benjamin I J (1993) Human Heat Shock Protein 70 (Hsp70) Protects Murine Cells from Injury During Metabolic Stress. *J Clin Invest* 92:503-508.

Wincott F, DiRenzo A, Shaffer C, Grimm S, Tracz D, Workman C, Sweedler D, Gonzalez C, Scaringe S & Usman N (1995) Synthesis, deprotection, analysis and purification of RNA and ribozymes. *Nucleic Acids Res* 23:2677-2684.

Wincott F E & Usman N (1997) A practical method for the production of RNA and ribozymes. *Methods Mol Bio* 74:59-68.

Yazawa K, Fisher W E & Brunicardi F C (2002) Current Progress in Suicide Gene Therapy for Cancer. *World J Surg* 26:783-789.

Yu D C, Chen Y, Seng M, Dilley J & Henderson D R (1999) The Addition of Adenovirus Type 5 Region E3 Enables Calydon Virus 787 to Eliminate Distant Prostate Tumor Xenografts. *Cancer Res* 59:4200-4203.

Yu J Y, DeRuiter S L & Turner D L (2002) RNA interference by expression of short-interfering RNAs and hairpin RNAs in mammalian cells. *Proc Natl Acad Sci USA* 99:6047-6052.

Zhang X, Li Y, Huang Q, Wang H, Yan B, Dewhirst M W & Li C Y (2003) Increased Resistance of Tumor Cells to Hyperthermia Mediated By Integrin-linked Kinase. *Clin Cancer Res* 9:1155-1160.

Zuker M. and Turner (1999) A Practical Guide In RNA Biochemistry and Biotechnology, NATO ASI Series, Mathews D H. J. Mol. Biol.

It will be understood that various details of the presently disclosed subject matter can be changed without departing from the scope of the presently disclosed subject matter. Furthermore, the foregoing description is for the purpose of illustration only, and not for the purpose of limitation.

---

What is claimed is:

1. A method of modulating cellular expression of at least one matrix metalloproteinase protein, the method comprising introducing into a cell at least one DNA oligonucleotide having binding specificity for a target region of a messenger ribonucleotide (mRNA) encoding a matrix metalloproteinase protein, wherein the at least one matrix metalloproteinase protein is MMP-2, MMP-9, or both MMP-2 and MMP-9, and wherein the DNA oliqonucleotide has a nucleotide sequence comprising the sequence of SEQ ID NO: 1, SEQ ID NO: 3 or SEQ ID NO: 22.

2. The method of claim 1, wherein modulating cellular expression of the matrix metalloproteinase protein comprises inhibiting expression of the matrix metalloproteinase protein.

3. The method of claim 1, wherein the DNA oligonucleotide is a DNAzyme.

4. The method of claim 3, wherein the DNAzyme comprises a catalytic domain flanked on each side by substrate binding domains each having binding specificity for a distinct nucleotide sequence of the target region.

5. The method of claim 4, wherein the DNA oligonucleotide comprises a modification that increases the stability of the DNA oligonucleotide.

6. The method of claim 5, wherein the modification comprises an inverted deoxythymidine at the 3' end of the DNA oligonucleotide.

* * * * *

```
SEQUENCE LISTING

<160> NUMBER OF SEQ ID NOS: 29

<210> SEQ ID NO 1
<211> LENGTH: 33
<212> TYPE: DNA
<213> ORGANISM: Artificial
<220> FEATURE:
<223> OTHER INFORMATION: Anti-human MMP-9 DNAzyme

<400> SEQUENCE: 1
aacaaactgg gctagctaca acgaatcctt ggt                                   33

<210> SEQ ID NO 2
<211> LENGTH: 33
<212> TYPE: DNA
<213> ORGANISM: Artificial
<220> FEATURE:
<223> OTHER INFORMATION: Anti-human MMP-9 DNAzyme

<400> SEQUENCE: 2
ttcttgtcgg gctagctaca acgatgtcaa agt                                   33

<210> SEQ ID NO 3
<211> LENGTH: 33
<212> TYPE: DNA
<213> ORGANISM: Artificial
<220> FEATURE:
<223> OTHER INFORMATION: Anti-human MMP-9 DNAzyme

<400> SEQUENCE: 3
agcccagcag gctagctaca acgacaggag cac                                   33

<210> SEQ ID NO 4
<211> LENGTH: 33
<212> TYPE: DNA
<213> ORGANISM: Artificial
<220> FEATURE:
<223> OTHER INFORMATION: Anti-human MMP-9 DNAzyme

<400> SEQUENCE: 4
aagggtggag gctagctaca acgatggcgc tgt                                   33
```

```
<210> SEQ ID NO 5
<211> LENGTH: 33
<212> TYPE: DNA
<213> ORGANISM: Artificial
<220> FEATURE:
<223> OTHER INFORMATION: Anti-human MMP-9 DNAzyme

<400> SEQUENCE: 5
atagcggtag gctagctaca acgaaggtat tcc                                33

<210> SEQ ID NO 6
<211> LENGTH: 33
<212> TYPE: DNA
<213> ORGANISM: Artificial
<220> FEATURE:
<223> OTHER INFORMATION: Anti-human MMP-9 DNAzyme

<400> SEQUENCE: 6
gtggtgccag gctagctaca acgattgagg tcg                                33

<210> SEQ ID NO 7
<211> LENGTH: 33
<212> TYPE: DNA
<213> ORGANISM: Artificial
<220> FEATURE:
<223> OTHER INFORMATION: Anti-human MMP-9 DNAzyme

<400> SEQUENCE: 7
gtggccgaag gctagctaca acgatcatgc gcc                                33

<210> SEQ ID NO 8
<211> LENGTH: 33
<212> TYPE: DNA
<213> ORGANISM: Artificial
<220> FEATURE:
<223> OTHER INFORMATION: Anti-human MMP-9 DNAzyme

<400> SEQUENCE: 8
ccccagagag gctagctaca acgattcgac tct                                33

<210> SEQ ID NO 9
<211> LENGTH: 33
<212> TYPE: DNA
<213> ORGANISM: Artificial
<220> FEATURE:
<223> OTHER INFORMATION: Anti-human MMP-9 DNAzyme

<400> SEQUENCE: 9
gcagcccagg gctagctaca acgaaccagg agc                                33

<210> SEQ ID NO 10
<211> LENGTH: 33
<212> TYPE: DNA
<213> ORGANISM: Artificial
<220> FEATURE:
<223> OTHER INFORMATION: Anti-human MMP-9 DNAzyme

<400> SEQUENCE: 10
agatttcgag gctagctaca acgatctcca cgc                                33

<210> SEQ ID NO 11
<211> LENGTH: 33
<212> TYPE: DNA
<213> ORGANISM: Artificial
<220> FEATURE:
<223> OTHER INFORMATION: Anti-human MMP-9 DNAzyme
```

```
<400> SEQUENCE: 11
agaggctcag gctagctaca acgaggtgag ggc                                33

<210> SEQ ID NO 12
<211> LENGTH: 33
<212> TYPE: DNA
<213> ORGANISM: Artificial
<220> FEATURE:
<223> OTHER INFORMATION: Anti-human MMP-2 DNAzyme

<400> SEQUENCE: 12
ccttcagcag gctagctaca acgaaaacag gtt                                33

<210> SEQ ID NO 13
<211> LENGTH: 33
<212> TYPE: DNA
<213> ORGANISM: Artificial
<220> FEATURE:
<223> OTHER INFORMATION: Negative control DNAzyme

<400> SEQUENCE: 13
accaaggatg gctagctaca acgacagttt gtt                                33

<210> SEQ ID NO 14
<211> LENGTH: 33
<212> TYPE: DNA
<213> ORGANISM: Artificial
<220> FEATURE:
<223> OTHER INFORMATION: Negative control DNAzyme

<400> SEQUENCE: 14
actttgacag gctagctaca acgacgacaa gaa                                33

<210> SEQ ID NO 15
<211> LENGTH: 33
<212> TYPE: DNA
<213> ORGANISM: Artificial
<220> FEATURE:
<223> OTHER INFORMATION: Negative control DNAzyme

<400> SEQUENCE: 15
gtgctcctgg gctagctaca acgatgctgg gct                                33

<210> SEQ ID NO 16
<211> LENGTH: 33
<212> TYPE: DNA
<213> ORGANISM: Artificial
<220> FEATURE:
<223> OTHER INFORMATION: Negative control DNAzyme

<400> SEQUENCE: 16
acagcgccag gctagctaca acgatccacc ctt                                33

<210> SEQ ID NO 17
<211> LENGTH: 33
<212> TYPE: DNA
<213> ORGANISM: Artificial
<220> FEATURE:
<223> OTHER INFORMATION: Negative control DNAzyme

<400> SEQUENCE: 17
ggaatacctg gctagctaca acgataccgc tat                                33

<210> SEQ ID NO 18
<211> LENGTH: 33
```

```
<212> TYPE: DNA
<213> ORGANISM: Artificial
<220> FEATURE:
<223> OTHER INFORMATION: Negative control DNAzyme

<400> SEQUENCE: 18
cgacctcaag gctagctaca acgatggcac cac                                    33

<210> SEQ ID NO 19
<211> LENGTH: 33
<212> TYPE: DNA
<213> ORGANISM: Artificial
<220> FEATURE:
<223> OTHER INFORMATION: Negatvie control DNAzyme

<400> SEQUENCE: 19
gccctcaccg gctagctaca acgatgagcc tct                                    33

<210> SEQ ID NO 20
<211> LENGTH: 33
<212> TYPE: DNA
<213> ORGANISM: Artificial
<220> FEATURE:
<223> OTHER INFORMATION: Negative control DNAzyme

<400> SEQUENCE: 20
ctagtcagcg gctagctaca acgataagct gct                                    33

<210> SEQ ID NO 21
<211> LENGTH: 33
<212> TYPE: DNA
<213> ORGANISM: Artificial
<220> FEATURE:
<223> OTHER INFORMATION: Negative control DNAzyme with non-functional
      catalytic domain

<400> SEQUENCE: 21
agcccagcaa gcaatgcacg atcgcaggag cac                                    33

<210> SEQ ID NO 22
<211> LENGTH: 33
<212> TYPE: DNA
<213> ORGANISM: Artificial
<220> FEATURE:
<223> OTHER INFORMATION: Anti-rat MMP-9 DNAzyme

<400> SEQUENCE: 22
atggtgccag gctagctaca acgattgagg tcg                                    33

<210> SEQ ID NO 23
<211> LENGTH: 33
<212> TYPE: DNA
<213> ORGANISM: Artificial
<220> FEATURE:
<223> OTHER INFORMATION: DNAzyme negative control

<400> SEQUENCE: 23
cgacctcaag gctagctaca acgatggcac cat                                    33

<210> SEQ ID NO 24
<211> LENGTH: 18
<212> TYPE: DNA
<213> ORGANISM: Artificial
<220> FEATURE:
<223> OTHER INFORMATION: Forward PCR primer for amplification of human
      MMP-9

<400> SEQUENCE: 24
```

```
gcaggaatgc ggctctgg                                                   18

<210> SEQ ID NO 25
<211> LENGTH: 17
<212> TYPE: DNA
<213> ORGANISM: Artificial
<220> FEATURE:
<223> OTHER INFORMATION: Reverse PCR primer for amplification of human
      MMP-9

<400> SEQUENCE: 25
cccgtcgaag ggatacc                                                    17

<210> SEQ ID NO 26
<211> LENGTH: 21
<212> TYPE: DNA
<213> ORGANISM: Artificial
<220> FEATURE:
<223> OTHER INFORMATION: Forward PCR primer for amplification of human
      B-actin

<400> SEQUENCE: 26
caagagatgg ccacggcggc t                                               21

<210> SEQ ID NO 27
<211> LENGTH: 21
<212> TYPE: DNA
<213> ORGANISM: Artificial
<220> FEATURE:
<223> OTHER INFORMATION: Reverse PCR primer for amplification of human
      B-actin

<400> SEQUENCE: 27
tccttctgca tcctgtcagc a                                               21

<210> SEQ ID NO 28
<211> LENGTH: 33
<212> TYPE: DNA
<213> ORGANISM: Artificial
<220> FEATURE:
<223> OTHER INFORMATION: Negative control DNAzyme

<400> SEQUENCE: 28
ctagtcagcg gctagctaca acgataagct gct                                  33

<210> SEQ ID NO 29
<211> LENGTH: 33
<212> TYPE: DNA
<213> ORGANISM: Artificial
<220> FEATURE:
<223> OTHER INFORMATION: Anti-Rat MMP-2 DNAzyme

<400> SEQUENCE: 29
ctttcacgag gctagctaca acgaaaagac gtt                                  33
```